(12) United States Patent
Aliper et al.

(10) Patent No.: US 11,260,078 B2
(45) Date of Patent: Mar. 1, 2022

(54) METHOD OF TREATING SENESCENCE WITH MULTI-STAGE LONGEVITY THERAPEUTICS

(71) Applicant: Insilico Medicine, Inc., Rockville, MD (US)

(72) Inventors: Aleksandr M. Aliper, Moscow (RU); Aleksandrs Zavoronkovs, Rockville, MD (US); Ivan Ozerov, Shchelkovo (RU); Marine E. Bozdaganyan, Balashikha (RU); Artem V. Artemov, Moscow (RU)

(73) Assignee: Insilico Medicine IP Limited, Hong Kong (HK)

( * ) Notice: Subject to any disclaimer, the term of this patent is extended or adjusted under 35 U.S.C. 154(b) by 710 days.

(21) Appl. No.: 16/044,784

(22) Filed: Jul. 25, 2018

(65) Prior Publication Data
US 2019/0030078 A1 Jan. 31, 2019

Related U.S. Application Data

(60) Provisional application No. 62/547,061, filed on Aug. 17, 2017, provisional application No. 62/536,658, filed on Jul. 25, 2017.

(51) Int. Cl.
| | | |
|---|---|---|
| *A61K 35/28* | (2015.01) | |
| *A61K 31/195* | (2006.01) | |
| *A61K 38/17* | (2006.01) | |
| *A61K 31/4709* | (2006.01) | |
| *A61K 31/519* | (2006.01) | |
| *A61K 31/506* | (2006.01) | |
| *A61K 31/4439* | (2006.01) | |
| *A61K 31/353* | (2006.01) | |
| *A61K 31/453* | (2006.01) | |
| *A61K 31/416* | (2006.01) | |
| *A61K 31/4412* | (2006.01) | |
| *A61K 31/192* | (2006.01) | |
| *A61K 31/436* | (2006.01) | |
| *A61K 31/12* | (2006.01) | |
| *A61K 45/06* | (2006.01) | |
| *A61K 31/4745* | (2006.01) | |
| *A61K 31/44* | (2006.01) | |
| *A61K 38/16* | (2006.01) | |
| *A61K 31/585* | (2006.01) | |
| *A61K 31/352* | (2006.01) | |
| *A61K 31/196* | (2006.01) | |
| *A61K 35/36* | (2015.01) | |
| *A61K 31/26* | (2006.01) | |
| *A61K 39/00* | (2006.01) | |

(52) U.S. Cl.
CPC .............. *A61K 35/28* (2013.01); *A61K 31/12* (2013.01); *A61K 31/192* (2013.01); *A61K 31/195* (2013.01); *A61K 31/196* (2013.01); *A61K 31/26* (2013.01); *A61K 31/352* (2013.01); *A61K 31/353* (2013.01); *A61K 31/416* (2013.01); *A61K 31/436* (2013.01); *A61K 31/44* (2013.01); *A61K 31/4412* (2013.01); *A61K 31/4439* (2013.01); *A61K 31/453* (2013.01); *A61K 31/4709* (2013.01); *A61K 31/4745* (2013.01); *A61K 31/506* (2013.01); *A61K 31/519* (2013.01); *A61K 31/585* (2013.01); *A61K 35/36* (2013.01); *A61K 38/16* (2013.01); *A61K 38/17* (2013.01); *A61K 45/06* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 8,592,646 | B2 | 11/2013 | Portereiko et al. |
| 9,141,756 | B1 | 9/2015 | Hillis et al. |
| 10,325,673 | B2 | 6/2019 | Aliper et al. |
| 10,665,326 | B2 | 5/2020 | Aliper et al. |
| 2019/0030078 | A1 | 1/2019 | Aliper et al. |
| 2019/0034581 | A1 | 1/2019 | Aliper et al. |
| 2019/0272890 | A1 | 9/2019 | Aliper et al. |
| 2020/0075127 | A1 | 3/2020 | Aliper et al. |

FOREIGN PATENT DOCUMENTS

| | | |
|---|---|---|
| CN | 108290059 A | 7/2018 |
| CN | 109415431 A | 3/2019 |

(Continued)

OTHER PUBLICATIONS

Davalli, Pierpaola, et al. "ROS, cell senescence, and novel molecular mechanisms in aging and age-related diseases." Oxidative medicine and cellular longevity 2016 (2016).*

(Continued)

*Primary Examiner* — G Steven Vanni
(74) *Attorney, Agent, or Firm* — Maschoff Brennan

(57) ABSTRACT

A method of treating senescence in a subject can include applying a senoremediation drug treatment protocol to the subject in order to rescue one or more first cells in the subject, wherein the senoremediation drug treatment protocol is derived from a computational transcriptome analysis of the tissue or organ of the subject. The method can include applying a senolytic drug treatment protocol to the subject in order to remove one or more second cells in the subject. The method can include introducing stem cells into a tissue and/or organ of the subject in order to rejuvenate one or more tissue cells in the tissue and/or one or more organ cells in the organ. The method can include carrying out a reinforcement step that includes one or more actions that prevent further senescence or degradation of the tissue or organ.

8 Claims, 13 Drawing Sheets

(56) References Cited

FOREIGN PATENT DOCUMENTS

| WO | 2014011735 A1 | 1/2014 | |
|---|---|---|---|
| WO | 2014091017 | 6/2014 | |
| WO | WO-2015136517 A1 * | 9/2015 | ......... G01N 33/5041 |
| WO | 2016151489 | 9/2016 | |
| WO | WO-2016185443 A1 * | 11/2016 | ............... A61P 9/12 |
| WO | 2020084536 | 4/2020 | |

OTHER PUBLICATIONS

International Search Report and Written Opinion PCT/IB2020/054644, dated Aug. 25, 2020.
International Search Report and Written Opinion PCT/IB2019/059087, dated Jan. 23, 2020.
Galkin et al. "Human Microbiome aging clocks based on deep learning and tandem of permutation feature importance and accumulated local effects." BIORXIV, Dec. 28, 2018 pp. 1-33.
Lan et al. "Selecting age-related functional characteristics in the human gun microbiome" Microbiome, vol. 1, Jan. 9, 2013, Article No. 2, pp. 1-12.
Pyrkov et al. "Extracting biological age from biomedical data via deep learning; too much of a good thing." Scientific Reports, vol. 8 Mar. 26, 2018, Article No. 5210, pp. 1-11.
Cole et al. "Predicting Age Using Neuroimaging: Innovative Brain Ageing Biomarkers." Trends in Neurosciences vol. 40 No. 12, Dec. 31, 2017 pp. 681-690.
International Search Report and Written Opinion PCT/IB2021/053430, dated Jun. 28, 2021.

* cited by examiner

| | | |
|---|---|---|
| PrestoBlue® (Invitrogen™, Switzerland) | Cell metabolic activity / viability | Both criteria |
| BCA Protein Assay (Pierce™, Switzerland) | Total protein content | - |
| BrdU incorporation (BioVision, Switzerland) | Proliferating cells | Senoremediation |
| Galacto-Star™ Assay (Invitrogen™) | β-Galactosidase activity | Open |
| Western Blot | p53Ser15p and total p53 | Open |
| MTT (Sigma-Aldrich®) | Cell viability / morphology | - |
| Coomassie Brilliant Blue | Protein staining (Cell morphology) | Senoremediation |
| DCFDA Assay (Sigma) | Oxidative Stress | - |
| CellEvent™ Caspase-3/7 (Invitrogen™) | Cell apoptosis | Senolysis |
| LIVE/DEAD™ Assay (Invitrogen™) | Cell necrosis / viability | - |

Fig. 3

METHOD OF TREATING SENESCENCE WITH MULTI-STAGE LONGEVITY THERAPEUTICS

CROSS-REFERENCE

This patent application claims priority to U.S. Provisional Application No. 62/536,658 filed Jul. 25, 2017, which provisional is incorporated herein by specific reference in its entirety.

This patent application claims priority to U.S. Provisional Application No. 62/547,061 filed Aug. 17 2017, which provisional is incorporated herein by specific reference in its entirety.

BACKGROUND

Until recently, treatments and therapies for senescence reversal (aging reversal) have been rare, largely because of the complexity of the underlying mechanisms of senescence and the lack of tools for understanding and treating senescence. One example of drug development for senescence protection (rather than senescence reversal) can be seen in US 2017/0073735. Recent bioinformatics developments such as deep neural networks have opened up the possibility of developing highly-personalized senescence reversal treatments, based on gene expression of senescent tissues versus non-senescent tissues, as will be disclosed in the present invention.

While aging may be a complex multifactorial process with no single cause or treatment, the issue whether aging can be classified as the disease is widely debated. Many strategies for extending organismal life spans have been proposed including replacing cells and organs, comprehensive strategies for repairing the accumulated damage, using hormetins to activate endogenous repair processes, modulating the aging processes through specific mutations, gene therapy and small molecule drugs. An animal's survival strongly depends on its ability to maintain homeostasis, achieved partly through intracellular and intercellular communication within and among different tissues.

Presently, none of the proposed strategies for senescence treatment provide a roadmap for rapid screening, validation and clinical deployment. No methods currently exist to predict the effects of currently available drugs on human longevity and health span in a timely manner.

Many biomarkers of aging have been proposed including telomere length, intracellular and extracellular aggregates, racemization of the amino acids and genetic instability. Gene expression and DNA methylation profiles change during aging also may be used as biomarkers of aging. Many studies analyzing transcriptomes of biopsies in a variety of diseases indicated that age and sex of the patient have significant effects on gene expression and that there are noticeable changes in gene expression with age in mice, resulting in development of mouse aging gene expression databases and in humans.

Combinations of protein-protein interaction and gene expression in both flies and humans demonstrate that aging is mainly associated with a small number of biological processes, which might preferentially attack key regulatory nodes that are important for network stability.

Work of the inventors, among others, with gene expression and epigenetics of various solid tumors provided clues that transcription profiles of cells mapped onto the signaling pathways may be used to screen for and rate the targeted drugs that regulate pathways directly and indirectly related to aging and longevity. Prior studies suggest that a combination of pathways, termed pathway cloud, instead of one element of the pathway or the whole pathway might be responsible for pathological changes in the cell.

The senescence response causes striking changes in cellular phenotype. Aging/senescence in humans causes striking changes in cellular phenotype. According to (Campisi and d'Adda di Fagagna 2007) the senescent phenotype is induced by multiple stimuli. Mitotically competent cells respond to various stressors by undergoing cellular senescence. These stressors include dysfunctional telomeres, non-telomeric DNA damage, excessive mitogenic signals including those produced by oncogenes (which also cause DNA damage), non-genotoxic stress such as perturbations to chromatin organization and, probably, stresses with an as-yet unknown etiology. These changes include an essentially permanent arrest of cell proliferation, development of resistance to apoptosis (the death of some cells that occurs as a normal and controlled part of an organism's growth or development) and an altered pattern of gene expression. Also, the expression or appearance of senescence-associated markers such as senescence-associated β-galactosidase, p16, senescence-associated DNA-damage foci (SDFs) and senescence-associated heterochromatin foci (SAHFs) are neither universal nor exclusive to the senescent state.

Cellular senescence is thought to contribute to age-related tissue and organ dysfunction and various chronic age-related diseases through various mechanisms. Senescence is characterized by a persistent proliferative arrest in which cells display a distinct pro-inflammatory senescent-associated secretory phenotype (SASP) (Krimpenfort and Berns 2017). Whereas SASP exerts a supportive paracrine function during early development and wound healing (Demaria et al. 2014), the continuous secretion of these SASP factors has detrimental effects on normal tissue homeostasis and is considered to significantly contribute to aging (DiLoreto and Murphy 2015).

In a cell-autonomous manner, senescence acts to deplete the various pools of cycling cells in an organism, including stem and progenitor cells. In this way, senescence interferes with tissue homeostasis and regeneration, and lays the groundwork for its cell-non-autonomous detrimental actions involving the SASP. There are at least five distinct paracrine mechanisms by which senescent cells are thought to promote tissue dysfunction, including perturbation of the stem cell niche (causing stem cell dysfunction), disruption of extracellular matrix, induction of aberrant cell differentiation (both creating abnormal tissue architecture), stimulation of sterile tissue inflammation, and induction of senescence in neighboring cells (paracrine senescence). An emerging yet untested concept is that post-mitotic, terminally differentiated cells that develop key properties of senescent cells might contribute to ageing and age-related disease through the same set of paracrine mechanisms (van Deursen 2014).

Several recent observations support the hypothesis that senescence is a highly-dynamic, multi-step process, during which the properties of senescent cells continuously evolve and diversify, much like tumorigenesis but without cell proliferation as a driver (De Cecco et al. 2013; Wang et al. 2011; Ivanov et al. 2013). This includes not only senescent cells but also take in account pre-senescent stage. This fact also means there is an opportunity to reverse the cell to normal non-senescent behavior.

At least two general concepts of age exist in the art. One, "chronological age" is simply the actual calendar time an organism or human has been alive. Another one, called "biological age" or "physiological age", which is a particular focus of the present invention, is related to the physiological health of the individual, and biomarkers thereof. Biological age is associated with how well organs and regulatory systems of the body are performing and at what extent the general homeostasis at all levels of the organism is being maintained, as such functions generally decline with time and age.

The measurement of any physiological process of an organism is typically done with a set of predefined biomarkers. A biomarker can be defined as a characteristic that is objectively measured and evaluated as an indicator of normal biological processes, pathogenic processes, or pharmacologic responses to a therapeutic intervention. Biomarkers are chosen by scientists in order to measure a very-well defined process within the body.

Given that in a multi-cellular organism that aging is a systemic process, which cannot be readily captured by single uni-dimensional or even several metrics, the development of an accurate and useful measure of biological age (which can be thought of as a biological clock), is subject to specific challenges. Again, such biomarkers must not only be an objective quantifiable and easily measurable characteristics of the biological aging process, but must also be able to take into account that aging is not a single specific process, but rather a suite of changes across multiple physiological systems.

In other words, no single biomarker can provide an accurate overall biological clock age of a multi-cellular organism, nor can the biological age of a single cell, tissue, or organ, even when composed of many biomarkers, provide an accurate overall biological age of an organism. And in fact, it is often useful to have several biological clocks assigned to an organism or human, that is, a different biological age can be assigned to different cells, tissues, or organs of that organism, as well as different clocks based on a different biomarker or different biomarker. Thus there may be one clock for the skin, one for the liver, one clock based on telomere length of a cell(s), tissue(s), or organ(s), and another based on a different biomarker.

In the past, several attempts have been made to develop adapted biomarkers for measuring biological aging. However, the biomarkers used so far focus on monitoring a restricted number of processes known for being directly involved in the onset and propagation of aging related damages through the body. Examples of such biomarkers are telomere length (Lehmann, 2013), intracellular and extracellular aggregates, racemization of the amino acids and genetic instability. Both gene expression (Wolters, 2013) and DNA methylation profiles (Horvath, 2012, Horvath, 2013, Mendelsohn, 2013) change during aging and may be used as biomarkers of aging as demonstrated previously with the epigenetic clock (Horvath, 2012, Horvath, 2013). Many studies analyzing transcriptomes of biopsies in a variety of diseases indicated that age and sex of the patient had significant effects on gene expression (Chowers, 2003) and that there are noticeable changes in gene expression with age in mice (Weindruch, 2002, Park, 2009), resulting in development of mouse aging gene expression databases (Zahn, 2007) and in humans (Blalock, 2003; Welle, 2003; Park, 2005; Hong, 2008; de Magalhães, J. P, 2009).

Work of the inventors, among others, with gene expression and epigenetics of various solid tumors provided clues that transcription profiles of cells mapped onto the signaling pathways may be used to screen for and rate the targeted drugs that regulate pathways directly and indirectly related to aging and longevity. Prior studies suggested that a combination of pathways, termed pathway cloud, instead of one element of the pathway or the whole pathway might be responsible for pathological changes in the cell.

There has always been a need to reverse senescence, but only recently are there the necessary tools, particularly, developments in informatics and machine learning, to develop and apply such senescence therapies and treatments. Further, even commonly-accepted biomarkers and metric of such biomarkers to assess aging have been lacking.

SUMMARY

In some embodiments, a method of treating senescence in a subject can include applying a senoremediation drug treatment protocol to the subject in order to rescue one or more first cells in the subject, wherein the senoremediation drug treatment protocol is derived from a computational transcriptome analysis of the tissue or organ of the subject. In some aspects, the method can include applying a senolytic drug treatment protocol to the subject in order to remove one or more second cells in the subject. In some aspects, the senolytic drug treatment protocol is derived from the computational transcriptome analysis of the tissue or organ of the subject. In some aspects, the method can include introducing stem cells into a tissue and/or organ of the subject in order to rejuvenate one or more tissue cells in the tissue and/or one or more organ cells in the organ. In some aspects, at least one of the following is derived from a computational transcriptome analysis of the tissue or organ of the subject: identification of the tissue for receiving the stem cells; or identification of the organ for receiving the stem cells. In some aspects, the method can include carrying out a reinforcement step that includes one or more actions that prevent further senescence or degradation of the tissue or organ. In some aspects, the method can include the one or more actions that prevent further senescence or degradation of the tissue or organ is derived from the computational transcriptome analysis of the tissue or organ of the subject. In some aspects, the method can include: applying a senolytic drug treatment protocol to the subject in order to remove one or more second cells in the subject. In some aspects, the method can include introducing stem cells into a tissue and/or organ of the subject in order to rejuvenate one or more tissue cells in the tissue and/or one or more organ cells in the organ. In some aspects, at least one of the following is derived from a computational transcriptome analysis of the tissue or organ of the subject: the senolytic drug treatment protocol; identification of the tissue for receiving the stem cells; or identification of the organ for receiving the stem cells. In some aspects, the method can include carrying out a reinforcement step that includes one or more actions that prevent further senescence or degradation of the tissue or organ. In some aspects, at least one of the following is derived from a computational transcriptome analysis of the tissue or organ of the subject: the senolytic drug treatment protocol; identification of the tissue for receiving the stem cells; identification of the organ for receiving the stem cells; or the one or more actions that prevent further senescence or degradation of the tissue or organ.

In one embodiment, a method of treating senescence in a subject can include: (a) applying a senoremediation drug treatment protocol to the subject in order to rescue one or more first cells in the subject; (b) applying a senolytic drug treatment protocol to the subject in order to remove one or more second cells in the subject; (c) introducing stem cells into a tissue and/or organ of the subject in order to rejuvenate one or more tissue cells in the tissue and/or one or more organ cells in the organ; and (d) carrying out a reinforcement step that includes one or more actions that prevent further senescence or degradation of the tissue or organ. In one aspect, at least one of the following is derived from a computational transcriptome analysis of the tissue or organ of the subject: the senoremediation drug treatment protocol; the senolytic drug treatment protocol; identification of the tissue for receiving the stem cells; identification of the organ for receiving the stem cells; and the one or more actions that prevent further senescence or degradation of the tissue or organ.

In some aspects, the first cells that are rescued are characterized as pre-senescent cells. In some aspects, the second cells that are removed are characterized as senescent cells. In some aspects, (a) (b) (c) or (d) are carried out in any order or any combination thereof carried out simultaneously. In some aspects, the method includes repeating at least one of (a) (b) (c) or (d) at least once. In some aspects, the stem cells are mesenchymal or epithelial stem cells or both. In some aspects, step (d) further comprises applying a reinforcement drug treatment protocol to the patient. In some aspects, the reinforcement drug treatment protocol includes at least one of: immunomodulation, cytoprotection, or stimulation of macrophages. In some aspects, the reinforcement drug treatment protocol includes at least one of: Insulin receptor substrate (Tyr608) peptide; 740 Y-P; Sapanisertib; Dactolisib; GSK2334470; MP7; Dasantinib; Quercitin; Flavopiridol; Linifanib; Argatroban; Sorafenib; Tucaresol; Methotrexate; Tacrolimus; Curcumin; Lavendustin A; Withaferin A; Sulphorapane. In some aspects, the computational transcriptome analysis produces a transcriptome signature that is used as input to a machine learning platform that outputs drug classifications for one of steps (a), (b), or (d). In some aspects, the computational transcriptome analysis produces a transcriptome signature that is compared to a baseline transcriptome signature that represents a less senescent version of the subject's tissue or organ. In some aspects, the computational transcriptome analysis produces a transcriptome signature that is compared to a baseline transcriptome signature that is constructed from more than one tissue or organ transcriptome signature of one or more different subjects.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 3 provides information for read-outs for senolytic and senoremediation compound validation.

Figure 1:
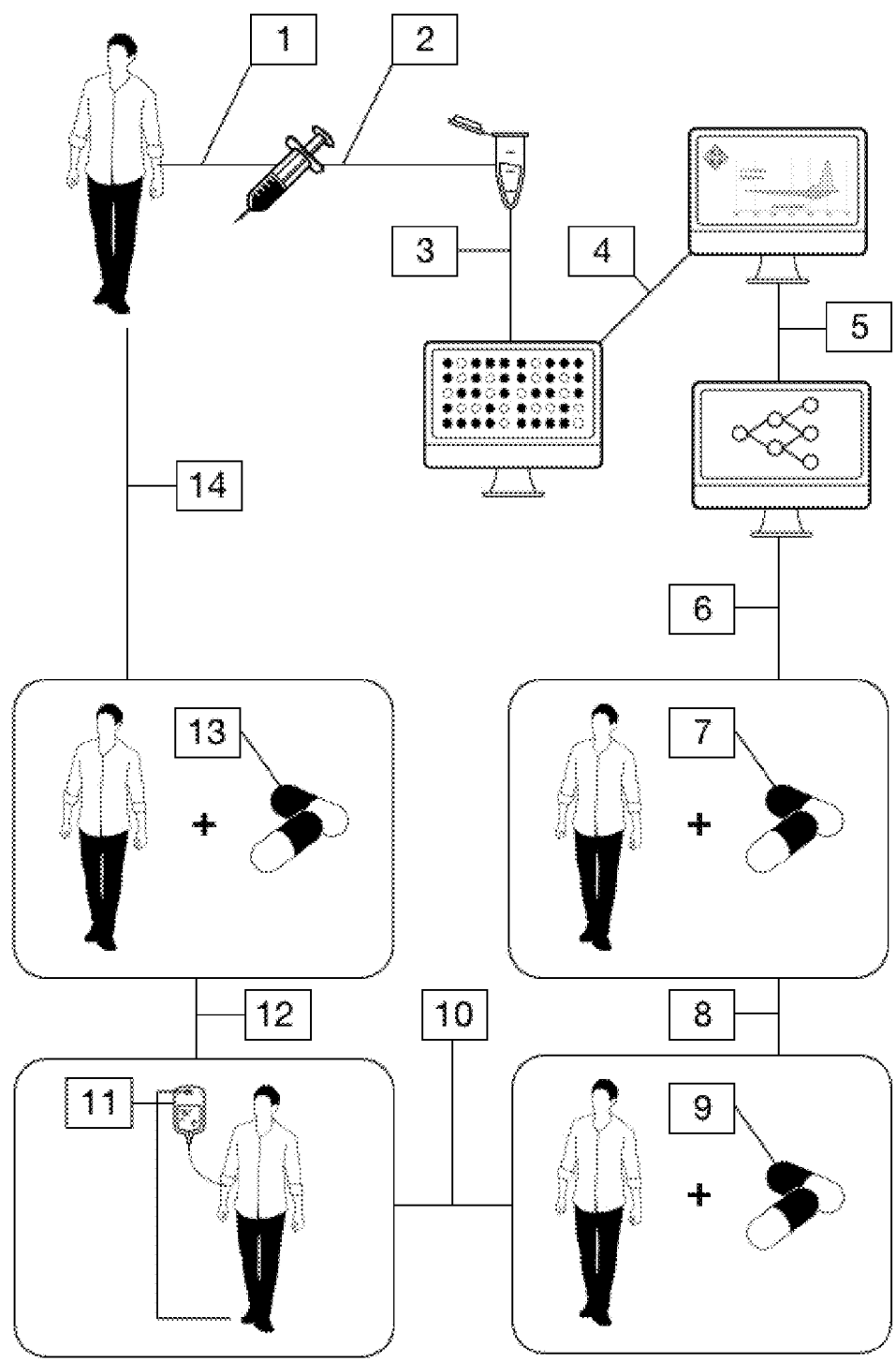
FIG. 1 shows an embodiment of a 5R strategy, which is applied to patients with pre-senescent, senescent or fibrotic conditions.

The elements in the figures are arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present invention generally relates to a multi-stage therapeutic for treating senescence (aging) of whole organisms (in particular, human individuals), as well as the organism's underlying cellular, tissue, and organ senescence. Methods and systems for applying such therapeutic treatment, as well as informatics and other tools for developing the therapeutic treatments, are disclosed. Since disease and senescence are often associated, the invention is also applicable to treating disease.

The present disclosure provides compositions and methods for 5R (Rescue, Remove, Replenish, Reinforce, Repeat) strategy selectively rescuing pre-senescent cells, removing senescent cells, replenishing and reinforcing by new healthy cells and repeating the procedure wherein the composition comprises a group of senolytics and their derivatives thereof. The strategy of 5R may delay aging and/or treat age-related disorders especially fibrotic and senofibrotic disorders primarily in lungs and liver.

This 5R method may delay aging and/or treat age-related disorders especially fibrotic and senofibrotic disorders primarily in lungs, liver and skin. The 5R strategy as described is applied to patients with pre-senescent, senescent, and fibrotic conditions, among others. Drugs to be used include senoremediators, antifibrotic agents, and senolytics. The 5R approach will result in induction of regeneration. Drug repurposing strategy can be part of the therapy development process once the therapy protocols have been designed.

FIG. 1 shows an embodiment of a 5R strategy, which is applied to patients with pre-senescent, senescent or fibrotic conditions. The following steps can be performed in any method described herein: 1. Single biopsy procedure; 2. Sample preparation; 3. Microarray, RNA-seq profiles; 4. iPANDA analysis; 5. Aging clock analysis; 6. Rescue stage procedure; 7. Senoremediator treatment; 8. Remove stage procedure; 9. Senolytics treatment; 10. Replenish stage procedure; 11. Therapy with stem cells; 12. Reinforce stage procedure; 13. Immunomodulator treatment; and 14. Repeat stage procedure. Any one of these steps may be performed alone or in combination of other steps as recited herein. In some instances, the methods can include obtaining data and processing the data to obtain a recommendation for a treatment protocol. The recommended treatment protocol can then be implemented on the patient in accordance with parameters of the treatment protocol. That is, without the computational generation of the treatment protocol, the aspects of the treatment protocol cannot be performed without the instructions to do so. As such, obtaining the instructions, such as the type of drug or specific drug or combination of drugs, can be vital for performing the treatment protocol.

In some instances, the treatment protocol can be obtained by steps 1, 2, 3, 4, and/or 5. Some of these steps may be omitted, such as steps 1, 2, and 3 when the sample is obtained already prepared. In some instances the data from 3 may be obtained and provided into a computing system for step 4 and/or 5. From the data of step 4 and/or 5, steps 6, 7, 8, 9, 10, 11, 12, and/or 13 can be performed as determined and in any order or in any combination and with any step being repeated in any order. In one example, the method can first perform 6 and then 8, or 8 and then 6. Steps 7 and/or 9 may be performed in any order with respect to each other. In an example, steps 8 and/or 9 can be performed prior to steps 10, 11, 12, or 13.

In some instances, there is a step 4a and/or step 5a, wherein a determined treatment protocol is provided by step 4 and/or step 5, respectively. The determined treatment protocol can include a list of one or more drugs or treatment actions for each treatment step subsequent to steps 4 and/or 5.

The invention includes methods, system, apparatus, computer program product, among others, to carry out the invention described herein.

In one embodiment, a method is provided for treating senescence in a patient tissue or organ, the method comprising: (a) carrying out a rescue step comprising applying a senoremediation drug treatment protocol to the patient; (b) carrying out a removal step comprising applying a senolytic drug treatment protocol to the patient; (c) carrying out a replenishment step comprising introducing stem cells in a particular tissue or organ; and (d) carrying out a reinforcement step comprising one or more preventative actions to prevent further senescence or degradation of the tissue or organ. These steps may be carried out in any order or repeated. The stem cells may be mesenchymal or epithelial stem cells or both. The method may further include applying a reinforcement drug treatment protocol to the patient, using, immunomodulation, cytoprotection, or stimulation of macrophages. In some aspects, wherein (a) (b) (c) or (d) are carried out in any order. In some aspects, the method includes repeating at least one of (a) (b) (c) or (d) at least once. In some aspects, the stem cells are mesenchymal or epithelial stem cells or both. In some aspects, (c) further comprises applying a reinforcement drug treatment protocol to the patient. In some aspects, (d) further comprising at least one of immunomodulation, cytoprotection, or stimulation of macrophages. In some aspects, a transcriptome signature representing tissue or organ senescence is used to develop at least one of the drugs used. In some aspects, the transcriptome signature is used as input to a machine learning platform that outputs drug classifications. In some aspects, the transcriptome signature is compared to a baseline transcriptome signature that represents a less senescent version of the patient's tissue or organ. In some aspects, the transcriptome signature is compared to a baseline transcriptome signature that is constructed from more than one tissue or organ transcriptome signature.

In some embodiments, a transcriptome signature representing tissue or organ senescence may be used to develop at least one of the drugs used, the drugs selected from a senoremediation drug, senolytic drug, antifibrotic drug, or preventative action drugs. The transcriptome signature may be a signaling pathway activation network analysis, which may be used as input into a computer, and processed to obtain the relevant data. Such computer processing of the signaling pathway can provide information regarding the transcriptome signature that can be obtained as output along with information for the senoremediation drug, senolytic drug, antifibrotic drug, or preventative action drugs. The transcriptome signature may be used in the following manner: as a signaling pathway activation network analysis, the transcriptome signature is used as input to a machine learning platform that outputs drug classifications. The transcriptome signature is compared in the computer to a baseline transcriptome signature that represents a less senescent version of the patient's tissue or organ, and the transcriptome signature is compared to a baseline transcriptome signature that is constructed from more than one tissue or organ transcriptome signature. The computer may process the data to determine a specific determined drug of at least one or more of the senoremediation drug, senolytic drug, antifibrotic drug, or preventative action drugs, and provide the determined drug as output. Then, the determined drug, one for each type, may be acquired and used in the treatments described herein.

The method for treating senescence in a patient tissue or organ may include applying an antifibrotic drug treatment protocol to the patient derived from a transcriptome signature of the patient, such as from the computer analysis thereof. The method may include wherein the antifibrotic drug treatment comprises at least one drug that destroys fibrotic cells. Alternatively, the method can include applying a pro-fibrotic drug treatment, wherein the pro-fibrotic drug treatment comprises at least one pro-fibrotic drug that restores fibrotic cells.

In one embodiment, a method described herein, such as treating senescence in a patient tissue or organ may include (a) carrying out a rescue step comprising applying a senoremediation drug treatment protocol to the patient; and (b) carrying out a removal step comprising applying a senolytic drug treatment protocol to the patient; wherein (a) and (b) may be done in any order, and at least one of the drug treatments is derived from a transcriptome analysis of the patient tissue or organ. The method may also include (c) carrying out a replenishment step comprising introducing stem cells in a particular tissue or organ; and (d) carrying out a reinforcement step comprising one or more methods to prevent further senescence or degradation of the tissue or organ.

In some aspects, the method can include repeating either (a) or (b) or both at least once. In some aspect, the method can include (a) or (b) being carried out in either order. In some aspects, the method can include (c) carrying out a replenishment step comprising introducing stem cells in a particular tissue or organ. In some aspects, the method can include repeating (c) at least once. In some aspects, the method can include (c) being carried out in any sequence with respect to (a) and (b). In some aspects, the stem cells are mesenchymal or epithelial stem cells or both. In some aspects, the method can include (c) further comprising using a reinforcement drug treatment protocol to the patient. In some aspects, the method can include repeating (c) at least once. In some aspects, the method can include (d) carrying out a reinforcement step comprising one or more methods to prevent further senescence or degradation of the tissue or organ. In some aspects, the method can include (d) being carried out in any sequence with respect to (a) (b) and (c). In some aspects, the method can include immunomodulation, cytoprotection, or stimulation of macrophages, or more than once. In some aspects, the method can include (a) or (b) or both comprising applying an antifibrotic drug treatment protocol to the patient derived from a transcriptome signature of the patient. In some aspects, the method can include the antifibrotic drug treatment having at least one drug that destroys fibrotic cells. In some aspects, antifibrotic drug treatment comprises at least one drug that restores fibrotic cells. In some aspects, the transcriptome signature is a signaling pathway activation network analysis. In some aspects, the transcriptome signature is used as input to a machine learning platform that outputs drug classifications. In some aspects, the transcriptome signature is compared to a baseline transcriptome signature that represents a less senescent version of the patient's tissue or organ. In some aspects, the transcriptome signature is compared to a baseline transcriptome signature that is constructed from more than one tissue or organ transcriptome signature. In some aspects, the transcriptome signature is used as input to a deep neural network that outputs drug classifications.

In some embodiments, a method of treating senescence in a patient tissue or organ can include: (a) carrying out a rescue step comprising applying a senoremediation drug treatment protocol to the patient; and wherein at least one of the drug treatments is derived from a transcriptome analysis of the patient tissue or organ. Here, step (a) can be performed alone. However, any of the other steps may also be performed as recited herein.

The steps may be carried out in any order or repeated. The stem cells may be mesenchymal or epithelial stem cells or both. The method may further include applying a reinforcement drug treatment protocol to the patient, using, immunomodulation, cytoprotection, or stimulation of macrophages.

A transcriptome signature representing tissue or organ senescence may be used to develop at least one of the drugs used. The transcriptome signature may be a signaling pathway activation network analysis, which is performed on a computer with models as described herein. The transcriptome signature may be used in the following manner: as a signaling pathway activation network analysis, the transcriptome signature is used as input to a machine learning platform that outputs drug classifications. The transcriptome signature is compared to a baseline transcriptome signature that represents a less senescent version of the patient's tissue or organ, and the transcriptome signature is compared to a baseline transcriptome signature that is constructed from more than one tissue or organ transcriptome signature.

The method may include applying an antifibrotic drug treatment protocol to the patient derived from a transcriptome signature of the patient. The method may include wherein the antifibrotic drug treatment comprises at least one drug that destroys fibrotic cells or a pro-fibrotic drug treatment comprises at least one drug that restores fibrotic cells.

The invention includes developing a personalized drug treatment, the method may include: (a) receiving a first transcriptome signature derived from a patient tissue or organ; (b) receiving a second first transcriptome signature derived from a baseline; (c) creating a difference matrix, such as in a computer with a model or neural network or machine learning, using the profile of (a) and the profile of (b); (d) receiving a cellular signature library; (e) receiving a drug therapeutic use library; (f) using the matrix of (c), the library of (d), and the library of (e) to provide input vectors to a machine learning platform, wherein the machine learning platform outputs classification vectors on one or more drugs, wherein the personalized drug treatment is comprised of the classification vectors.

The transcriptome signature may be based on a signature signaling pathway activation network analysis on a computer. One of the transcriptome signatures is based an in silico signaling pathway activation network decomposition. One of the profiles may comprise a Pearson correlation matrix. The personalized drug treatment may comprise a senescence treatment for the patient. The profile of (b)—the second first transcriptome signature derived from a baseline—may be derived from a non-senescent tissue or organ of the patient or another subject. The method may include the machine learning platform comprising one or more deep neural networks. The method may include the machine learning platform comprising at least two generative adversarial networks and may comprise an adversarial autoencoder architecture. The personalized drug treatment may be created by prescribing drugs identified by the classification vectors at their lowest effective dose.

The invention includes a method of computationally, with a computer, designing a treatment protocol for a patient comprising one or more drugs, the method comprising: (a) identifying a gene expression signature of the patient; (b) defining a patient score for signatures taken from one or more patient tissues or organs; (c) selecting drugs based upon (a) and/or (b); and (d) defining a lowest effective combination for each drug. The method may include the gene expression signature being based on a signature signaling pathway activation network analysis, wherein gene expression signatures is based on an in silico signaling pathway activation network decomposition, wherein the gene expression signature comprises a transcriptome Pearson correlation matrix. The method can then include one or more treatment steps with one or more treatment drugs or treatment steps of any of the treatment methods described herein.

The protocol may be a senescence treatment for the patient. The method may include wherein: the signature of (a)—gene expression signature of the patient is derived, using a computer with appropriate algorithms or models (e.g., neural network) from a non-senescent tissue or organ of the patient or another subject, wherein (b) and (c) are carried out on a machine learning platform, wherein the machine learning platform comprises at least two generative adversarial networks, wherein the machine learning platform comprises an adversarial autoencoder architecture, wherein the machine learning platform comprises one or more deep neural networks.

In some embodiments, a computer program product can include a non-transitory computer readable medium having a computer readable program code embodied therein, the product being executable by a processor to perform a method for estimating the fractional gluconeogenesis of a patient, the method comprising developing a personalized drug treatment, comprising: (a) receiving a first transcriptome signature derived from a patient tissue or organ; (b) receiving a second first transcriptome signature derived from a baseline; (c) creating a difference matrix using the profile of (a) and the profile of (b); (d) receiving a cellular signature library; (e) receiving a drug therapeutic use library; (f) using the matrix of (c), the library of (d) and/or (e), to provide input vectors to a machine learning platform, wherein the machine learning platform outputs classification vectors on one or more drugs, wherein the personalized drug treatment is comprised of the classification vectors.

In one aspect, at least one of the transcriptome signatures is based on a signature signaling pathway activation network analysis. In one aspect, at least one of the transcriptome signatures is based an in silico signaling pathway activation network decomposition. In one aspect, at least one of the profiles comprises a transcriptome Pearson correlation matrix. In one aspect, the personalized drug treatment comprises a senescence treatment for the patient. In one aspect, the profile of (b) is derived from a non-senescent tissue or organ of the patient or another subject. In one aspect, the machine learning platform comprises one or more deep neural networks. In one aspect, the machine learning platform comprises at least two generative adversarial networks. In one aspect, the machine learning platform comprises an adversarial autoencoder architecture. In one aspect, the personalized drug treatment is created by prescribing drugs identified by the classification vectors at their lowest effective dose.

The computer processing can include input and or processing of a complete or partial schematic overview of the biochemistry of senescence. Additional information can be obtained in the incorporated provisional application regarding the biological pathways that can be uses as input and processing for determining a treatment, such as specific drugs for the treatment. Accordingly, the biological pathways can be used in the methods described herein. Such biological pathways are described herein with some examples of computer processing thereof for implanting the design of treatment protocols as recited herein.

A variety of cell-intrinsic and -extrinsic stresses that can activate the cellular senescence program can be used as input for a simulation or other computer processing. The biological pathways that are known, such as in the literature, can be analyzed for specific biological steps that are performed. Modulation of the biological step either to increase the activity or decrease the activity results in a cascading series of events in response to the modulated activity. The modulations can be with drugs, substances, of other affirmative actions that effect a modulation of the biological pathway. This modulation can be measured for a defined biological step. The biological step and the change in response to the modulation activity can be used as inputs into computer models, and such computer models can be trained on the data. Now, with the increase in artificial intelligence and deep learning algorithms, such biological steps, the modulation activity, and the changed response can be used with such computer models for modeling biological pathways. This can allow for determining a modulation activity for one or more biological steps. Such modulations activities can be real and based on the simulations, such as being a real drug, substance, or medical action. The output of the computer models can be instructions or other information for causing the modulation activity in order to obtain a specific type of biological step modulation so that the end goal of a specifically modulated biological pathway can be obtained. Accordingly, the biological pathways described herein, or in the incorporated references and provisional applications, can be used as the biological pathways for the treatment protocols described herein.

In a specific example, the biological pathways can relate to senescence, and the modulation thereof.

The biological pathways related to senescence can be used for computer models. Stressors are known to cause biological pathway modulation that results in senescence. For example, some stressors engage various cellular signaling cascades and can ultimately activate p53, p16Ink4a, or both. Some stress types that activate p53 through DDR signaling can be analyzed and computed. This can include computationally processing the ROS to elicit the DDR by perturbing gene transcription and DNA replication, as well as by shortening telomeres. The computer can also compute biological pathways of activated p53 that induces p21, which induces a temporal cell-cycle arrest by inhibiting cyclin E-Cdk2, which can be processed. The computer can also analyze how p16Ink4a also inhibits cell-cycle progression by targeting cyclin D-Cdk4 and cyclin D-Cdk6 complexes. Both p21 and p16Ink4a act by preventing the inactivation of Rb, thus resulting in continued repression of E2F target genes required for S-phase onset. Upon severe stress as modeled and computationally processed, temporally arrested cells that transition into a senescent growth arrest through a mechanism that is currently incompletely understood can be determined. Cells exposed to mild damage that can be successfully repaired may resume normal cell-cycle progression. On the other hand, cells exposed to moderate stress that is chronic in nature or that leaves permanent damage may resume proliferation through reliance on stress support pathways, and such information may be included in the data processing. This phenomenon (termed assisted cycling) is enabled by p53-mediated activation of p21, which can be taken into account when computationally determine a treatment, such as a drug treatment. Thus, the p53-p21 pathway can either antagonize or synergize with p16Ink4a in senescence depending on the type and level of stress that is used in the computational processing. BRAF (V600E) is unusual in that it establishes senescence through a metabolic effector pathway. BRAF (V600E) activates PDH by inducing PDP2 and inhibiting PDK1 expression, promoting a shift from glycolysis to oxidative phosphorylation that creates senescence-inducing redox stress, which can be taken into account in the computational processing. Cells undergoing senescence induce an inflammatory transcriptome regardless of the senescence inducing stress, and such inflammatory transcriptome can be considered in determining the treatment. Also, senescence-promoting and senescence-preventing activities may be computed, and may be weighted relative to their importance. A senescence-reversing mechanism may be input or modeled or otherwise computed as part of the process.

A multi-step senescence model can also be input and computed. The model can be programmed to consider cellular senescence as a dynamic process driven by epigenetic and genetic changes. An initial step computes the progression from a transient to a stable cell-cycle arrest through analysis of a sustained activation of the p16Ink4a and/or p53-p21 pathways. The model can consider the resulting early senescent cells progress to full senescence by downregulating lamin B1, thereby triggering extensive chromatin remodeling underlying the production of a SASP. The model can consider certain components of the SASP that are highly conserved, whereas others may vary depending on cell type, nature of the senescence-inducing stressor, or cell-to-cell variability in chromatin remodeling. The computation can consider progression to deep or late senescence that may be driven by additional genetic and epigenetic changes, which can be computed, including chromatin budding, histone proteolysis and retrotransposition, driving further transcriptional change and SASP heterogeneity. The computation can consider the efficiency with which immune cells dispose of senescent cells, and which may be dependent on the composition of the SASP. The proinflammatory signature of the SASP can fade due to expression of particular microRNAs late into the senescence program, thereby perhaps allowing evasion of immuno-clearance, which can also be considered.

In some embodiments, a conceptual model can be computed in which senescent cells are subdivided into two main classes based on kinetics of senescence induction and functionality. The conceptual model can consider that acute senescence is induced through cell-extrinsic stimuli that target a specific population of cells in the tissue. Acute senescent cells self-organize their elimination through SASP components that attract various types of immune cells. The conceptual model can be programmed to consider that induction of chronic senescence occurs after periods of progressive cellular stress or macromolecular damage when tarry cycling transitions into a stable cell-cycle arrest. The conceptual model can consider that age-related immunodeficiency or production of less proinflammatory SASPs, immune cells may inefficiently eliminate chronic senescent cells, allowing continuation of multi-step senescence. For example, the conceptual model may consider that senescence induced during cancer therapy may initially be acute and later chronic in nature.

The computer models can be programed and receive senescence input data for computing how senescence promotes age-related tissue dysfunction. Senescence contributes to the overall decline in tissue regenerative potential that occurs with ageing. The computer models can be programed with the observation that progenitor cell populations in both skeletal muscle and fat tissue of BubR1 progeroid mice are highly prone to cellular senescence. Proteases chronically secreted by senescent cells may perturb tissue structure and organization by cleaving membrane-bound receptors, signaling ligands, extracellular matrix proteins or other components in the tissue microenvironment, which can affect the treatment protocols described herein. In addition, other SASP components, including IL-6 and IL-8, may stimulate tissue fibrosis in certain epithelial tissues by inducing EMT may be considered. Chronic tissue inflammation, which is characterized by infiltration of macrophages and lymphocytes, fibrosis and cell death, is associated with ageing and has a causal role in the development of various age-related diseases, which can be considered during identifying a treatment.

The matrix metalloproteinases and proinflammatory SASP components can be modeled and considered in determining a treatment because of their ability create a tissue microenvironment that promotes survival, proliferation and dissemination of neoplastic cells. The model can be processed so that SASP can be modeled for increasing age-related tissue deterioration through paracrine senescence, where senescent cells spread the senescence phenotype to healthy neighboring cells through secretion of IL-lb, TGFb and certain chemokine ligands. With gene expression analysis or pathway analysis it is possible to distinguish between pre-senescent and senescent cells signatures with the computations.

The models can be computed to consider that killing senescent cells can lead to rejuvenation of the tissue. For example, a modified FOXO4-p53 interfering peptide can be considered that causes p53 and induces targeted apoptosis of senescent cells (TASC), which neutralizes murine liver chemotoxicity from doxorubicin treatment. The TASC can be considered for restoring fitness, hair density, and renal function in fast and naturally aged mice.

The model can be processed so that delaying senescence or even promote death of accumulating apoptosis-resistant senescent cells can be a strategy to prevent age related diseases. Tocotrienols (T3s) and quercetin (Q) can be input for modeling as senolytics agents (e.g., small molecules that can selectively induce death of senescent cells). Both drugs are able to kill pre-senescent and senescent cells and can be used adjuvant therapy of cancer and preventive anti-aging strategies, and thereby can be used in the treatments herein.

The computational models can also consider fibrosis and senofibrosis conditions. The term fibrosis describes the development of fibrous connective tissue as a reparative response to injury or damage, which can be considered during computing for treatment protocols. Fibrosis may refer to the connective tissue deposition that occurs as part of normal healing or to the excess tissue deposition that occurs as a pathological process. The term senofibrosis describes the development of fibrous connective tissue under influence of senescent cells, which can be considered during computing for treatment protocols. Senescent activated cells lose their proliferative and collagen-producing capacity and have increased inflammatory property to produce inflammatory cytokines compared with replicating activated "normal" cells. The computational models can focus on two types of fibrosis and senofibrosis treatment: pulmonary (IPF) and liver.

The models can be processed to consider that fibrosis is a wound healing response that produces and deposits extracellular matrix (ECM) proteins including collagen fibers, causing tissue scarring. Liver usually regenerates after liver injury. However, when liver injury and inflammation are persistent and progressive, liver cannot regenerate normally and causes fibrosis. Hepatic stellate cells (HSCs) are the primary source of activated myofibroblasts that produce extracellular matrix in the liver. Progressive liver fibrosis results in cirrhosis where liver cells cannot function properly due to the formation of fibrous scar and regenerative nodules and the decreased blood supply to the liver. The model can perform such simulations. The model can consider three main reasons for liver fibrosis: alcoholic fatty diseases; non-alcoholic fatty diseases; and viral hepatitis. In each case different mechanisms lead to fibrotic tissue formation, which mechanisms can be processed to determine a suitable protocol.

The model can also consider that quiescent HSCs store Vitamin A-containing lipid droplets, and HSCs lose lipid droplets when they are activated. Transforming growth factor (TGF)-β and platelet-derived growth factor (PDGF) are two major cytokines that contribute to HSC activation and proliferation, resulting in activation into myofibroblasts. Many other cytokines, intracellular signaling, and transcription factors are involved in this process, and may be considered during computations.

The computational models can also consider activation and regression of hepatic stellate cells. Quiescent hepatic stellate cells (HSCs) store Vitamin A containing lipid droplets and lose Vitamin A when the cells are activated. Hepatic epithelial injury, such as death of hepatocytes and biliary epithelial cells, induces activation of HSCs directly or through cytokines released from immune cells including Kupffer cells, bone marrow-derived monocytes, Th17 cells, and innate lymphoid cells (ILC). Transforming growth factor-f (TGF-f), platelet-derived growth factor (PDGF), interleukin-1f (IL-1f), IL-17, and intestine-derived lipopolysaccharide (LPS) promote HSC activation. IL-33 promotes HSC activation through ILC2. Autophagy in HSCs is associated with HSC activation. The activated myofibroblast pool is mainly constituted by activated HSCs, but biliary injury induces differentiation of portal fibroblasts to activated myofibroblasts. However, there is no evidence of epithelial-mesenchymal transition for constituting the myofibroblast pool. After the cessation of causative liver injury, fibrosis starts regression, and activated HSCs induce apoptosis or revert into a quiescent state. Peroxisome proliferator-activated receptor 7 (PPAR7) expression in HSCs is associated with HSC reversal. Some activated HSCs become senescent, resulting in loss of profibrogenic property in which p53 plays a role. Moreover, angiogenesis contributes to both fibrosis development and regression. As such, each may be considered when computing a therapeutic protocol.

The main pathways that are involved in modulation of hepatic inflammation can be categorized as (1) Upregulated and (2) Downregulated. The main pathways that are involved in formation of cellular senescence in HSCs can be categorized as (1) Upregulated and (2) Downregulated. Both upregulation and downregulation of any biological pathway, such as those described herein, may be considered during the computation of therapeutic protocols.

The main pathways which are involved in formation of cellular senescence phenotype in primary human hepatocytes (PHH). Data for the analysis is taken from LINCs transcriptomic dataset and computed as described herein. Methanesulfonate is a DNA damage/senescence inducer, which may be used in obtaining data to train the models. Liver senescence and liver fibrosis signatures hold the common features on the pathway level (analysis is based on the gene expression data using iPANDA, as described further below.

The main pathways which are involved in formation of cellular senescence phenotype in primary human hepatocytes (PHH). Data for the analysis, and model computations for determining a therapeutic protocol can be taken from LINCs transcriptomic dataset. The following are Up-regulated: BRCA1 Pathway Homologous Recombination Repair; JNK Pathway Insulin Signaling; Caspase Cascade Pathway Activated Tissue Trans-glutaminase; JNK Pathway Gene Expression Apoptosis Inflammation Tumorigenesis Cell Migration via SMAD4, STAT4, HSF1, TP53, MAP2, DCX, ATF2, NFATC3, SPIRE1, MAP1B, TCF15, ELK1, BCL2, JUN, PXN, and NFATC2; Caspase Cascade Pathway DNA Fragmentation; TRAF Pathway Gene Expression via FOS and JUN; IF1Alpha Pathway Gene Expression via JUN and CREB3; TNF Signaling Pathway Apoptosis; PTEN Pathway Genomic Stability; VEGF Pathway Gene Expression and Cell Proliferation via MAPK7; ErbB Family Pathway Gene Expression via JUN, FOS, and ELK1; PTEN Pathway Ca2+ Signaling; PTEN Pathway DNA Repair; VEGF Pathway Prostaglandin Production; MAPK Family Pathway Gene Expression via ATF2, JUN, ELK1, NFKB2, and CREB3; HIF1Alpha Pathway; WNT Pathway; ATM Pathway Cell Survival; and MAPK Family Pathway Translation. The following are Down-regulated: Ras Pathway Increased T-cell Adhesion; HGF Pathway Cell Adhesion and Cell Migration; IGF1R Signaling Pathway Cell Migration; ILK Signaling Pathway Cell Migration Retraction; ILK Signaling Pathway Cell Cycle Proliferation; ILK Signaling Pathway G2 Phase Arrest; ILK Signaling Pathway Cytoskeletal Adhesion Complexes; ILK Signaling Pathway Loss of Occludin Barrier Dysfunction; ATM Pathway Cell Cycle Checkpoint Control; Akt Signaling Pathway AR mediated apoptosis; Akt Signaling Pathway Apoptosis; Akt Signaling Pathway Cell Cycle Progression; and Akt Signaling Pathway Elevation of Glucose Import. The role of senescence of HSCs in liver fibrosis may be computed, and experimental data using cell-specific genetic modifications to HSCs from experimental models of liver fibrosis in vivo can be used in the computation of treatment protocols.

There is no treatment for liver fibrosis still. The only way to avoid it is to prevent massive inflammation by rescuing or killing pre-senescent and senescent cells accordingly. Liver senescence and liver fibrosis signatures hold the common features on the pathway level (analysis is based on the gene expression data using iPANDA package). The common significant pathways involved into modulation liver fibrosis (and cirrhosis) are that can be considered in the computation models include the following upregulated and down regulated pathways. Those upregulated include: ILK Signaling Pathway Opsonization; ILK Signaling Pathway Cell Adhesion; ILK Signaling Pathway Wound Healing; Akt Signaling Pathway AR mediated apoptosis; TRAF Pathway; IL-10 Pathway Stability Determination; EGF Pathway Rab5 Regulation Pathway; TRAF Pathway Gene Expression via FOS and JUN; ILK Signaling Pathway Tumor Angiogenesis; Akt Signaling Pathway NF-kB dependent transcription; HIF1Alpha Pathway Gene Expression via JUN and CREB3; Chemokine Pathway; STAT3 Pathway Growth Arrest and Differentiation; TRAF Pathway Apoptosis; Erythropoietin Pathway GPI Hidrolysis and Ca2+ influx; IL-10 Pathway; IL-10 Pathway Inflammatory Cytokine Genes Expression via STAT3; ILK Signaling Pathway MMP2 MMP9 Gene Expression Tissue Invasion via FOS; ErbB Family Pathway Gene Expression via JUN, FOS, and ELK1; Akt Signaling Pathway Regulation of Na+ Transport; PAK Pathway Paxillin Disassembly; ILK Signaling Pathway Cytoskeletal Adhesion Complexes; cAMP Pathway Glycogen Synthesis; and ILK Signaling Pathway Cell Migration Retraction. Those downregulated include: STAT3 Pathway Anti-Apoptosis; Akt Signaling Pathway Cell Cycle Progression; Circadian Pathway; Growth Hormone Signaling Pathway Protein Synthesis; and PTEN Pathway Migration.

The common significant pathways involved in formation of cellular senescence and liver fibrosis that can be computed include those that are upregulated and downregulated. Those upregulated include: ErbB Family Pathway Gene Expression via JUN, FOS, and ELK1; HIF1Alpha Pathway Gene Expression via JUN and CREB3; and TRAF Pathway Gene Expression via FOS and JUN. Those downregulated include Akt Signaling Pathway Cell Cycle Progression. The common significant pathways involved into modulation of IPF include those upregulated or downregulated. Those upregulated include: Cellular Apoptosis Pathway; KEGG Choline metabolism in cancer Main Pathway; KEGG Prostate cancer Main Pathway; NCI CXCR4 mediated signaling events Main Pathway; NCI Syndecan 4 mediated signaling events Main Pathway; NCI TRAIL signaling Main Pathway; NCI Validated transcriptional targets of deltaNp63 isoforms Main Pathway; NCI Validated transcriptional targets of deltaNp63 isoforms Pathway (Pathway degradation of TP63); PTEN Pathway Adhesion or Migration; PTEN Pathway Angiogenesis and Tumorigenesis; PTEN Pathway Ca2+ Signaling; reactome Collagen biosynthesis and modifying enzymes Main Pathway; and reactome SMAD2, SMAD3, and SMAD4, heterotrimer regulates transcription Main Pathway. Those downregulated include: Growth Hormone Signaling Pathway Gene Expression via SRF, ELK1, STATSB, CEBPD, STAT1, STAT3; and reactome Tie2 Signaling Main Pathway.

The common significant pathways involved in formation of cellular senescence in lung tissue can include those upregulated and downregulated. Those upregulated include: Growth Hormone Signaling Pathway Gene Expression via SRF, ELK1, STATSB, CEBPD, STAT1, STAT3; KEGG Choline metabolism in cancer Main Pathway; KEGG Prostate cancer Main Pathway; NCI CXCR4 mediated signaling events Main Pathway; NCI TRAIL signaling Main Pathway; PTEN Pathway Adhesion or Migration; PTEN Pathway Angiogenesis and Tumorigenesis; PTEN Pathway Ca2+ Signaling; reactome Collagen biosynthesis and modifying enzymes Main Pathway; reactome SMAD2, SMAD3, SMAD4 heterotrimer regulates transcription Main Pathway; and reactome Tie2 Signaling Main Pathway. Those downregulated include: Cellular Apoptosis Pathway; NCI Syndecan 4 mediated signaling events Main Pathway; NCI Validated transcriptional targets of deltaNp63 isoforms Main; Pathway; NCI Validated transcriptional targets of deltaNp63 isoforms Pathway (Pathway degradation of TP63).

Cellular senescence can contribute to accelerating organ aging, and, among the pulmonary diseases that can be related to pulmonary senescence, chronic obstructive pulmonary disease/emphysema (COPD) and idiopathic pulmonary fibrosis (IPF), are the most common and lethal. COPD and IPF are severe multifactorial pulmonary disorders characterized by distinct clinical and pathologic features ("Global Strategy for the Diagnosis, Management, and Prevention of Chronic Obstructive Pulmonary Disease: GOLD Executive Summary Updated 2003" 2004; Noble et al. 2011). The date regarding clinical and pathological features can be used in the computational models that are processed for determining the therapeutic protocols.

In all known types of cellular senescence, including replicative cellular senescence, stress-induced senescence, and oncogene-induced senescence, a permanent state of cell cycle arrest occurs that is mediated by the expression of p16INK4a and p21WAF1, 2 cell cycle inhibitors that are also well-recognized markers, to investigate this mechanism in vivo (Kim and Sharpless 2006; Campisi 2005; Mallette and Ferbeyre 2007; Ohtani et al. 2004; Takeuchi et al. 2010). Altered expression of p16INK4a, p21WAF1, and b-galactosidase (a widely used histochemical marker of cellular senescence) have been demonstrated in IPF (Minagawa et al. 2010; Kuwano et al. 1996; Lomas et al. 2012). These markers are expressed strongly at sites of alveolar damage and hyperplasia, as well as in fibroblast foci localized in the discrete clusters of bronchiolar basal cells coexpressing the laminin-5-g2 chain (LAM5g2) and heat shock protein 27 (Hsp27) (Chilosi et al. 2006). According to review (Chilosi et al. 2013) several factors lead to senescence in lungs, they are different for two types: idiopathic pulmonary fibrosis and chronic obstructive pulmonary disease/emphysema pathogenesis. This information may also be used in the computational models for determining therapeutic protocols.

Methods for development of senescence drug treatments, that is, the selection of drugs, dosages, and cycles, are described herein. In this section, we give an overview of the drug treatments, themselves, that is, application of the personalized treatments once they have been designed, in a preferred embodiment, to the patient. In that patient, a tissue or organ is identified to which the senescent treatment will be applied.

In a preferred embodiment, one phase of the treatment involves senoremediation, that is, a drug protocol of senoremediators, which are drugs that restore or increase the amount of presenescent cells (cells that are typical or a young, healthy tissue or organ). Another phase of the treatment involves senolytic treatment, that is, a drug protocol that involves restoring or that involves elimination or destruction of senescent cells in the tissue or organ of interest.

In another preferred embodiment, there is also an antifibrotic phase, that is, a drug protocol that addressing fibrotic cells in the tissue or organ of interest. Antifibrotic may involve restoring senescent cells to a pre-senescent, non-fibrotic state, elimination or destruction of fibrotic cells, or both.

Since such drug treatment protocols are highly specific, and based upon the classification vectors of the analyses described herein, they may take many forms. Methods in the art, such as Seim et. al., "Gene expression signatures of human cell and tissue longevity", npj Aging and Mechanisms of Disease, 2, 16014 (2016), addresses transcriptome changes/differences associated with senescence that are used to classify drug protocols.

To examine gene expression strategies that support the lifespan of different cell types within the human body, one can obtain available RNA-seq data sets and interrogated transcriptomes of various somatic cell types and tissues with reported cellular turnover, along with an estimate of lifespan, ranging from 2 days (monocytes) to effectively a lifetime (neurons). Across different cell lineages, one can obtain a gene expression signature of human cell and tissue turnover. In particular, turnover showed a negative correlation with the energetically costly cell cycle and factors supporting genome stability, concomitant risk factors for aging-associated pathologies.

Comparative transcriptome studies of long-lived and short-lived mammals, and analyses that examined the longevity trait across a large group of mammals (tissue-by-tissue surveys, focusing on brain, liver and kidney), have revealed candidate longevity-associated processes. Publicly available transcriptome data sets (for example, RNA-seq) generated by consortia, such as the Human Protein Atlas (HPA) can be used. They offer an opportunity to understand how gene expression programs are related to cellular turnover, as a proxy for cellular lifespan. Gene expression patterns are typically analyzed, in a preferred embodiment, using Principal Component Analysis (PCA), as a first step.

The present invention involves examining aging transcriptome in which the transcribed genes in old to young people are compared to define a set first of genes which are more strongly expressed (activated) in old people relative to young people and a second set of genes (repressed) which are less strongly expressed in old people relative to young people. A preferred embodiment is herein described.

A rating approach can be used to rank the senescence treating properties of treatments first involves collecting the transcriptome datasets from young and old patients and normalizing the data for each cell and tissue type, evaluating the pathway activation strength (PAS) for each individual pathway and constructing the pathway cloud and screen for drugs or combinations that minimize the signaling pathway cloud disturbance by acting on one or multiple elements of the pathway cloud. Drugs and combinations may be rated by their ability to return the signaling pathway activation pattern closer to that of the younger tissue samples. The predictions may be then tested both in vitro and in vivo on human cells and on model organisms such as rodents, nematodes and flies to validate the screening and rating algorithms.

In a preferred embodiment of the senescence treatment, a method for ranking drugs, the method including; a. collecting young subject transcriptome data and old subject transcriptome data for one species to evaluate pathway activation strength (PAS) and down-regulation strength for a plurality of biological pathways; b. mapping the plurality of biological pathways for the activation strength and down-regulation strength from old subject samples relative to young subject samples to form a pathway cloud map; and c. providing a rating for each of a plurality of drugs in accordance with a drug rating for minimizing signaling pathway cloud disturbance (SPCD) in the pathway cloud map of the one species to provide a ranking of the drugs.

Pathway Activation and Pathway Activation Network Decomposition Analysis (iPANDA), is a preferred method of network analysis for the methods described herein.

Development of senescence treatments (in particular drug combinations and protocols) as contemplated by the authors, are particularly compatible with the signaling pathway activation network analysis as described, for example, in U.S. 62/401,789 (Ozerov, filed September 2016, now US 2018-0125865) and Ozerov et. al., "In silico Pathway Activation Network Decomposition Analysis (iPANDA) as a method for biomarker development", Nature Communications, 7: 13427, 2016, and both incorporated by specific reference in their entity. Such methods include large-scale transcriptomic data analysis that involves insilico Pathway Activation Network Decomposition Analysis (iPANDA). The capabilities of this method apply to multiple data sets containing data on obtained, for example, from Gene Expression Omnibus (GEO). Data sets in GEO are accessed by identifier, or accession number, such as GSE5350.

Additionally, according to an embodiment of the present invention, the pathway cloud map shows at least one upregulated/activated pathway and at least one down-regulated pathway of the old subject relative to the young subject. Furthermore, according to an embodiment of the present invention, the pathway cloud map is based on a plurality of young subjects and a plurality of old subjects. Importantly, according to an embodiment of the present invention, the method is performed for an individual to determine an optimized ranking of drugs for the individual.

Further, according to an embodiment of the present invention, the samples or biopsies are bodily samples selected from one or more of a blood sample, a urine sample, a biopsy, a hair sample, a nail sample, a breathe sample, a saliva sample, or a skin sample.

Yet further, according to an embodiment of the present invention, the pathway activation strength is calculated by dividing the expression levels for a gene n in the old subject samples by the gene expression levels of the young subject samples.

Additionally, according to an embodiment of the present invention, the pathway activation strength is calculated in accordance with $$SO = \frac{\prod_{i=1}^{N} [AGEL]_i}{\prod_{j=1}^{N} [RGEL]_j}$$

The [RGEL]i is an activator gene expression level and [RGEL]j is a repressor gene expression level) are expression level of activators gene i and j, respectively.

Yet further, according to an embodiment of the present invention, to drugs or combinations that minimize the signaling pathway cloud disturbance (SPCD).

Additionally, according to an embodiment of the present invention, the SPCD is a ratio of [AGEL]i, which is the activator gene #i expression level, to [RGEL]j, which is the repressor gene #j expression level, and wherein this is calculated for activator and repressor proteins in the pathway.

Cellular Network Analysis and iPANDA

There are well known method in the art (see, for example, U.S. Pat. No. 8,623,592) for treating patients with methods for predicting responses of cells to treatment with therapeutic agents. These methods involve measuring, in a sample of the cells, levels of one or more components of a cellular network and then computing a Network Activation State (NAS) or a Network Inhibition State (NIS) for the cells using a computational model of the cellular network. The response of the cells to treatment is then predicted based on the NAS or NIS value that has been computed. The present invention also comprises predictive methods for cellular responsiveness in which computation of a NAS or NIS value for the cells (e.g., senescent cells) is combined with use of a statistical classification algorithm. A preferred method of iPANDA implementation is now described. The method of transcriptomic data analysis, typically includes receiving cell transcriptomic data of a control group (C) and cell transcriptomic data (S) of group under study for a gene, calculating a fold change ratio (fc) for the gene, repeating steps a and b for a plurality of genes, grouping co-expressed genes into modules, estimating gene importance factors based on a network topology, mapped from a plurality of the modules, in order to obtain an in silico Pathway Activation Network Decomposition Analysis (iPANDA) value, the iPANDA value having a Pearson coefficient greater than a Pearson coefficient associated with another platform for manipulating the control cell transcriptomic data and the cell transcriptomic data of group under study for the plurality of genes. Steps may also include determining a biological an in silico Pathway Activation Network Decomposition Analysis (iPANDA) associated with at least one of the above the module, providing a classifier for treatment response prediction of a drug to a disease, wherein the disease is selected from a senescence and another disease or disorder, applying at least one statistical filtering test and a statistical threshold test to the fc values, obtaining proliferative bodily samples and healthy bodily samples from patients, applying the drug to the patients, determining responder and non-responder patients to the drug. The method also often includes comparing gene expression in at least one of selected signaling pathways and metabolic pathways, often associated with a drug.

One of the most relevant challenges in transcriptomic data analysis is the inherent complexity of gene network interactions, which remains a significant obstacle in building comprehensive predictive models. Moreover, high diversity of experimental platforms and inconsistency of the data coming from the various types of equipment—may also lead to the incorrect interpretation of the underlying biological processes. Although a number of data normalization approaches have been proposed over the recent years it remains difficult to achieve robust results over a group of independent data sets even when they are obtained from the same profiling platform. This may be explained by a range of biological factors, such as wide heterogeneity among individuals on the population basis, variance in the cell cycle stage of the cells used or a set of technical factors, such as sample preparation or batch variations in reagents.

A preferred embodiment of the present invention is compatible with the large-scale transcriptomic data analysis called in silico Pathway Activation Network Decomposition Analysis (iPANDA) as described herein. iPANDA is an effective tool for biologically relevant dimension reduction in transcriptomic data.

Overview of a Preferred iPANDA Embodiment

Fold changes between the gene expression levels in the samples under investigation and an average expression level of samples within the normal set is used as input data for the iPANDA algorithm. Since some genes may have a stronger effect on the pathway activation than others, the gene importance factor has been introduced. Several approaches of gene importance hierarchy calculation have been proposed during the last few decades. The vast majority of these approaches aim to enrich pathway-based models with specific gene markers most relevant for a given study. While some of them use detailed kinetic models of several particular metabolic networks to derive importance factors, in others, gene importance is derived from the statistical analysis of the gene expression data obtained for disease cases and healthy samples.

The iPANDA approach integrates different analytical concepts described above into a single network model as it simultaneously exploits statistical and topological weights for gene importance estimation. The smooth threshold based on the P values from a t-test performed on groups of two contrasting tissue samples is applied to the gene expression values. The smooth threshold is defined as a continuous function of P value ranging from 0 to 1. The statistical weights for genes are also derived during this procedure. The topological weights for genes are obtained during the pathway map decomposition. The topological weight of each gene is proportional to the number of independent paths through the pathway gene network represented as a directed graph.

It is well known that multiple genes exhibit considerable correlations in their expression levels. Most algorithms for pathway analysis treat gene expression levels as independent variables, which, despite the common belief, is not suitable when the topology based coefficients are applied. Indeed, due to exchangeability, there is no dependence of pathway activation values on how the topology weights are distributed over a set of coexpressed genes with correlated expression levels, and hence correlated fold changes. Thus, the computation of topological coefficients for a set of coexpressed genes is inefficient, unless a group of coexpressed genes is being considered as a single unit. To circumvent this challenge, gene modules reflecting the coexpression of genes are introduced in the iPANDA algorithm. The wide database of gene coexpression in human samples, COEXPRESdb, and the database of the downstream genes controlled by various transcriptional factors are utilized for grouping genes into modules. In this way, the topological coefficients are estimated for each gene module as a whole rather than for individual genes inside the module The contribution of gene units (including gene modules and individual genes) to pathway activation is computed as a product of their fold changes in logarithmic scale, topological and statistical weights. Then the contributions are multiplied by a discrete coefficient which equals to −1 or +1 in the case of pathway activation or suppression by the particular unit, respectively. Finally, the activation scores, which we refer to as iPANDA values, are obtained as a linear combination of the scores calculated for gene units that contribute to the pathway activation/suppression. Therefore, the iPANDA values represent the signed scores showing the intensity and direction of pathway activation.

Pathway Quality Metrics and iPANDA

Although currently there are several publicly available pipelines for benchmarking the transcriptomic data analysis algorithms, our aim is to generalize the approaches for pathway-based algorithm testing and reveal the common features of reliable pathway-based expression data analysis. We term these features "pathway analysis quality hallmarks". Efficient methods for pathway-based transcriptomic data analysis should be capable to perform a significant noise reduction in the input data and aggregate output data as a small number of highly informative features (pathway markers).

Scalability (the ability to process pathways with small or large numbers of genes similarly) is another critical aspect that should be considered when designing a reliable pathway analysis approach, since pathway activation values for pathways of different sizes should be equally credible. The list of pathway markers identified should be relevant to the specific phenotype or medical condition, and robust over multiple data sets related to the process or biological state under investigation. The calculation time should be reasonable to allow high-throughput screening of large transcriptomic data sets. To address the iPANDA algorithm in respect to these hallmarks and to fully assess its true potential and limitations, we have directly compared the results obtained by iPANDA using the tissue and Microarray Analysis Quality Control (MAQC)-I data sets with five other widely used third-party viable alternatives (GSEA8, SPIA9, Pathway Level Analysis of Gene Expression (PLAGE)26, single sample Gene Set Enrichment Analysis (ssGSEA) and Denoising Algorithm based on Relevant network Topology (DART)).

iPANDA as a Tool for Noise Reduction in Transcriptomic Data

One of the major issues that should be addressed when developing a novel transcriptomic data analysis algorithm is the ability of the proposed method to reduce noise while retaining the biologically relevant information of the results. Since pathway-based analysis algorithms are considered dimension reduction techniques, the pathway activation scores should represent collective variables describing only biologically significant changes in the gene expression profile.

In order to estimate the ability of the iPANDA algorithm to perform noise reduction while preserving biologically relevant features, we performed an analysis of the well-known MAQC data set (GEO identifier GSE5350). It contains data for the same cell samples processed using various transcriptome profiling platforms. A satisfactory pathway or network analysis algorithm should reduce the noise level and demonstrate a higher degree of similarity between the samples in comparison to the similarity calculated using gene set data.

To estimate gene level similarity only fold changes for differentially expressed genes (t-test P value<0.05) were utilized. Pearson correlation is chosen as a metric to measure the similarity between samples. Sample-wise correlation coefficients were obtained for the same samples profiled on Affymetrix and Agilent platforms. Similar procedure is performed using pathway activation values (iPANDA values).

Notably, the similarity calculated using pathway activation values generated by the iPANDA algorithm significantly exceeds the one calculated using fold changes for the differentially expressed genes (mean sample-wise correlation is over 0.88 and 0.79, respectively). To further validate our algorithm, we directly compared its noise reduction efficacy with that of other routinely used methods for transcriptome-based pathway analysis, such as SPIA, GSEA, ssGSEA, PLAGE and DART.

The mean sample-wise correlation between platforms is 0.88 for iPANDA compared with 0.53 for GSEA, 0.84 for SPIA, 0.69 for ssGSEA, 0.67 for PLAGE and 0.41 for DART. Furthermore, the sample-wise correlation distribution obtained using iPANDA values is narrowed to a range of 0.79 to 0.94, compared with −0.08-0.80, 0.60-0.92, 0.61-0.74, 0.45-0.75 and −0.11-0.60 for GSEA, SPIA, ssGSEA, PLAGE and DART, respectively.

In a preferred embodiment, iPANDA does generally assign more weights to genes that tend to be reliably coexpressed using information from COEXPRESSdb database. The information from COEXPRESSdb is utilized solely for grouping genes into modules, and hence cannot introduce any favorable bias towards iPANDA in this assessment. Even when the feature for grouping genes into modules is 'switched off', meaning that all genes are considered individually and no information from COEXPRESSdb is being utilized, iPANDA scores show higher sample-wise similarity between data obtained using various profiling platforms compared with the similarity calculated on the gene level.

Biomarker Identification and Relevance and iPANDA

As a next step we address the iPANDA ability to identify potential biomarkers (or pathway markers) of the phenotype under investigation. One of the commonly used methods to assess the capability of transcriptomic pathway markers to distinguish between two groups of samples (for example, resistance and sensitivity to treatment) is to measure their receiver operating characteristics area under curve (AUC) values. The capacity to generate a high number of biomarkers with high AUC values is a major requirement for any prospective transcriptomic data analysis algorithm to be used in prediction models.

iPANDA Produces Highly Robust Set of Biomarkers

One of the most important shortcomings of modern pathway analysis approaches is their inability to produce consistent results for different data sets obtained independently for the same biological case. Here we show that iPANDA algorithm applied to the tissue data overcomes this flaw and produces highly consistent set of pathway markers across the data sets used in the study. The iPANDA algorithm is an advantageous method for biologically relevant pathway marker development compared with the other pathway-based approaches.

The common marker pathway (CMP) index is applied to drug treatment response data for in order to estimate the robustness of the biomarker lists. Pathway marker lists obtained for four independent data sets were analyzed. The calculation of pathway activation scores is performed using the iPANDA algorithm and its versions with disabled gene grouping and/or topological weights. The 'off' state of topology coefficients means that they are equal to 1 for all genes during the calculation. Also, the 'off' state for the gene grouping means that all the genes are treated as individual genes. The application of the gene modules without topology-based coefficients reduces the robustness of the algorithm as well as the overall number of common pathway markers between data sets. Turning on the topology-based coefficients just slightly increases the robustness of the algorithm. Whereas using topology and gene modules simultaneously dramatically improves this parameter for both tissue types. This result implies that the combined implementation of the gene modules along with the topology-based coefficients serves as an effective way of noise reduction in gene expression data and allows one to obtain stable pathway activation scores for a set of independent data.

PANDA biomarkers as classifiers for prediction models. High AUC values for the pathway markers shown in suggest that iPANDA scores may be efficiently used as classifiers for biological condition prediction challenges.

In order to classify the samples as responders or non-responders, the random forest models were developed using iPANDA scores obtained for training sets of samples for each end point. Subsequently, performance of these models is measured using validation sets. Matthew's Correlation Coefficients (MCC), specificity and sensitivity metrics were applied to evaluate performance of the models. MCC metrics were chosen for the ease to calculate and due to their informativeness even when the distribution of the two classes is highly skewed. The similar random forest models were built using pathway activation (enrichment) scores obtained by other pathway analysis algorithms, including SPIA, GSEA, DART, ssGSEA and PLAGE. Moreover, to fully assess the performance of iPANDA-based paclitaxel sensitivity prediction models, we have trained the similar random forest models on four different gene expression subsets: expression levels of all genes (log GE), fold change for all genes between the training set and corresponding normals (log FC), expression levels of most differentially expressed genes (t-test P<0.05) (log DGE), and fold change in expression levels of most differentially expressed genes (t-test P<0.05) between the training and corresponding normal breast tissue data sets (log DFC). Logarithmic scale is used for training the gene level models. All pathway-level and gene-level data is Z-score normalized separately for each GEO data set used.

Application of the pathway activation measurement implemented in iPANDA leads to significant noise reduction in the input data and hence enhances the ability to produce highly consistent sets of biologically relevant biomarkers acquired on multiple transcriptomic data sets. Another advantage of the approach presented is the high speed of the computation. The gene grouping and topological weights are the most demanding parts of the algorithm from the perspective of computational resources. Luckily, these steps can be precalculated only once before the actual calculations using transcriptomic data. The calculation time for a single sample processing equals B1.4 s on the Intel® Core i3-3217U 1.8 GHz CPU (compared with 10 min for SPIA, 4 min for DART, about 10 s for ssGSEA, GSEA and PLAGE). Thus, iPANDA can be an efficient tool for high-throughput biomarker screening of large transcriptomic data sets.

The use of merely microarray data for pathway activation analysis has well-known limitations, as it cannot address individual variations in the gene sequence and consequently in the activity of its product. For example, a gene can have a mutation that reduces activity of its product but elevates its expression level through a negative feedback loop. Thus, the elevated expression of the gene does not necessarily corresponds with the increase in the activity of its product.

Although the iPANDA algorithm is initially designed for microarray data analysis, it can also be easily applied to the data derived from genome-wide association studies (GWAS). In order to do so, GWAS data can be converted to a form amenable for the iPANDA algorithm. Single-point mutations are assigned to the genes based on their proximity to the reading frames. Then each single-point mutation is given a weight derived from a GWAS data statistical analysis 40. Simultaneous use of the GWAS data along with microarray data may improve the predictions made by the iPANDA method.

One of the rapidly emerging areas in biomedical data analysis is deep learning. Recently several successful studies on microarray data analysis using various deep learning approaches on gene-level data have surfaced. Using pathway activation scores may be an efficient way to reduce dimensionality of transcriptomic data for drug discovery applications while maintaining biological relevant features. From an experimental point of view, gene regulatory networks are controlled via activation or inhibition of a specific set of signaling pathways. Thus, using the iPANDA signaling pathway activation scores as input for deep learning methods could bring results closer to experimental settings and make them more interpretable to bench biologists. One of the most difficult steps of multilayer perceptron training is the dimension reduction and feature selection procedures, which aim to generate the appropriate input for further learning. Signaling pathway activation scoring using iPANDA will likely help reduce the dimensionality of expression data without losing biological relevance and may be used as an input to deep learning methods especially for drug discovery applications. Using iPANDA values as an input data is particularly useful for obtaining reproducible results when analyzing transcriptomic data from multiple sources.

The gene expression data from different data sets is preprocessed using GCRMA algorithm 45 and summarized using updated chip definition files from Brainarray repository (Version 18) for each data set independently.

Taken together, iPANDA demonstrates better performance for the noise reduction test in comparison to other pathway analysis approaches, suggesting its credibility as a powerful tool for noise reduction in transcriptomic data analysis. iPANDA ha strong ability to identify potential biomarkers (or pathway markers) of the phenotype under investigation. One of the commonly used methods to assess the capability of transcriptomic pathway markers to distinguish between two groups of samples (for example, resistance and sensitivity to treatment) is to measure their receiver operating characteristics area under curve (AUC) values. The capacity to generate a high number of biomarkers with high AUC values is a major requirement for any prospective transcriptomic data analysis algorithm to be used in prediction models.

There are several widely used collections of signaling pathways including Kyoto Encyclopedia of Genes and Genomes (KEGG), QIAGEN and NCI Pathway Interaction Database. In this study, the collection of signaling pathways most strongly associated with various types of malignant transformation in human cells were used, obtained from the SABiosciences collection (sabiosciences dot com/pathway-central dot php). Using a senescence-specific pathway database can be used to ensure the presence of multiple pathway markers for the particular condition under investigation. Each pathway contains an explicitly defined topology represented as a directed graph. Each node corresponds to a gene or a set of genes while edges describe biochemical interactions between genes in nodes and/or their products. All interactions are classified as activation or inhibition of downstream nodes. The pathway size ranges from about twenty to over six hundred genes in a single pathway.

The iPANDA approach for large-scale transcriptomic data analysis accounts for the gene grouping into modules based on the precalculated gene coexpression data. Each gene module represents a set of genes which experience significant coordination in their expression levels and/or are regulated by the same expression factors. Therefore the actual function for the calculation of the pathway p activation according to the proposed iPANDA algorithm consists of two terms. While the first one corresponds to the contribution of the individual genes, which are not members of any module, the second one takes into account the contribution of the gene modules. Therefore the final function for obtaining a iPANDA value for the activation of pathway p, which consists of the individual genes i and gene modules j, has the following analytical form:

$$iPANDA_p = \sum_i G_{ip} + \sum_j M_{jp}$$

The contribution of the individual genes (Gip) and the gene modules (Mjp) is 15 computed as follows:

$$G_{ip} = w_i^S \cdot w_{ip}^T \cdot A_{ip} \cdot lg(fc_i)$$

$$M_{jp} = \max(w_i^S) \cdot \frac{1}{N} \sum_i^N (w_{ip}^T \cdot A_{ip} \cdot lg(fc_i))$$

Here fci is the fold change of the expression level for the gene i in the sample 20 under study to the normal level (average in a control group). As the expression levels are assumed to be logarithmically normally distributed and in order to convert the product over fold change values to sum, logarithmic fold changes are utilized in the final equation. Activation sign Aip is a discrete coefficient showing the direction in which the particular gene affects the pathway given. It equals +1 if the product of the 25 gene i has a positive contribution to the pathway activation and −1 if it has a negative contribution. The factors wiS and wipT are the statistical and topological weights of the $$iPANDA_p = \sum_i G_{ip} + \sum_j M_{ip}$$

$$G_{ip} = w_i^S \cdot w_{ip}^T \cdot A_{ip} \cdot lg(fc_i)$$

$$M_{jp} = \max(w_i^S) \cdot \frac{1}{N} \sum_i^N (w_{ip}^T \cdot A_{ip} \cdot lg(fc_i))$$

with gene i ranging from 0 to 1. The derivation procedure for these factors is described in detail in the subsequent sections. Since lg(fci) and Aip values can be positive or negative, the iPANDA values for the pathways can also have different signs. Thus positive or negative iPANDA values correspond to pathway activation or inhibition respectively.

Obtaining Gene Importance Factors

In order to estimate the topological weight (wipT), all possible walks through the gene network are calculated on the directed graph associated with the pathway map. The nodes of the graph represent genes or gene modules, while the edges correspond to biochemical interactions. The nodes which have zero incoming edges are chosen as the starting points of the walks and those which have zero outgoing edges are chosen as the final points. Loops are forbidden during walks computation. The number of walks Nip through the pathway p which include gene i is calculated for each gene. Then wipT is obtained as the ratio of Nip to the maximum value of Njp over all genes in the pathway:

$$w_{ip}^T = \frac{N_{ip}}{\max(N_{jp})}$$

The statistical weight depends on the p-values which are calculated from group t-test for case and normal sets of samples for each gene. The method called p-20 value thresholding is commonly used to filter out spurious genes which demonstrate no significant differences between sets. However, a major issue with the use of sharp threshold functions is that it can introduce an instability in filtered genes and as a consequence in pathway activation scores between the data sets. Additionally, the pathway activation values become sensitive to an arbitrary choice of the cutoff value. In order to address this issue, using a smooth threshold function is suggested. In the present study, the cosine function on logarithmic scale is utilized:

$$w_i^S = \begin{cases} 0, \\ \left(\cos\left(\pi \frac{\log p - \log p_{min}}{\log p_{max} - \log p_{min}}\right) + 1\right)/2, \\ 1, \end{cases}$$

$0, p > p_{max}, p \leq p_{min}; 2, p_{min} < p \leq p_{max}$ where pmin and pmax are the high and low threshold values. In this study p-value thresholds equal to 10-7 and 10-1 respectively. For the threshold values given over 58% of all genes pass high threshold and about 12% also pass low threshold for the data under investigation. Hence over 45% of the genes in the data set receive intermediate wiS values. Therefore more stable results for pathway activation scores between data sets can be achieved using this approach.

Grouping Genes into Modules

To obtain the gene modules, two independent sources of data were utilized: 10 human database of coexpressed genes COEXPRESdb 18 and the database of the downstream genes controlled by human sequence-specific transcription factors 19. The latter is simply intersected with the genes from the pathway database used, while correlation data from COEXPRESdb is clustered using Euclidean distance matrix.

Distances were obtained according to the following equation:

$$r_{ij} = 1 - \text{corr}_{ij}$$

where $\text{corr}_{ij}$ is correlation between expression levels of genes i and j. DBScan and hierarchical clustering with an average linkage criteria were utilized to identify clusters. Only clusters with an average internal pairwise correlation higher than 0.3 were considered. Clusters obtained from the transcription factors database and coexpression database were recursively merged to remove duplicates. A pair of clusters is combined into one during the merging procedure if the intersection level between clusters had been higher than 0.7. As a result, a set of 169 gene modules which includes a total of 1021 unique genes is constructed.

Statistical Credibility of the iPANDA Values

The p-values for the iPANDA pathway activation scores are obtained using weighted Fisher's combined probability test.

Algorithm Robustness Estimation

In order to quantitatively estimate the robustness of the algorithm between data sets, the Common Marker Pathway (CMP) index is introduced. The CMP 15 index is a function of the number of pathways considered as markers that are common between data sets. It also depends on the quality of the treatment response prediction when these pathways are used as classifiers. The CMP index is defined as follows:

$$CMP = \frac{1}{n}\sum_{j=1}^{n}\sum_{i} \ln(N_i) \times (AUC_{ij} - AUC_R)$$

where n is the number of data sets under study, Ni is the number of genes in the pathway i and AUCij is the value of the ROC area under curve which shows the quality of the separation between responders and non-responders to treatment when pathway i is used as classifier for the j-th data set. AUCR is the AUC value for a random classifier and equals to 0.5. A pathway is considered as a marker if its AUC value is higher than 0.8. The ln(Ni) term is included to increase the contribution of the larger pathways because they have a smaller probability to randomly get a high AUC value. The higher values of the CMP index correspond to the most robust prediction of pathway markers across the data sets under investigation, while zero value of CMP index corresponds to the empty intersection of the pathway marker lists obtained for the different data sets.

Clustering of Data Samples

In order to apply iPANDA to the Paclitaxel treatment response prediction over a several independent data sets, the pathway activation values were normalized to the Z-scores independently for each data set. The expected values used for the Z-scoring procedure were adjusted to the number of responders and non-responders in the data set under study. The pairwise distance matrix between samples utilized for further clustering is obtained using the $$D_{ij} = \sqrt{\frac{1}{N} \cdot \sum_{p}^{N} (iPANDA_{ip} - iPANDA_{jp})^2}$$

Here Dij is the distance between samples i and j, N is the number of the pathway markers used for the distance calculation. iPANDAip and iPANDAip are the normalized iPANDA values for the pathway p for the samples i and j respectively. Normalization of iPANDA values to the Z-scores implies that all the considered pathway markers have an equal contribution to the distance obtained. All distances were converted into similarities (1−Dij) before the clustering procedure. Hierarchical clustering using Ward linkage is performed on the distance matrix to divide the samples into groups.

Transcriptome (Gene Expression) Difference

In a preferred embodiment, two iPANDA transcriptome signatures, one from a senescent patient tissue or organ to be treated (or similar proxy profile) and another representing a target, no senescent tissue or organ, are compared to observe transcriptome (gene expression) differences. Principal component analysis is typically applied. Gene expression trees, difference matrices matrix may also be use, as is known in the art, for example using techniques know in the art. In a preferred embodiment, a difference matrix provides the vector inputs for a machine learning architecture as described below.

In a preferred embodiment, gene expression patterns are subjected to Principal Component Analysis (PCA). In an embodiment wherein many different tissue samples are taken, rather than just two, several clusters are formed, suggesting related biological functions for these clusters. For example, the gastrointestinal tissues, esophagus, rectum and colon all grouped together, and hematopoietic tissues (bone marrow and spleen) and monocytes also clustered. Because transcriptomes of functionally related cell types often exhibit substantial hierarchical structure a neighbor-joining gene expression tree can be generated based on mean gene expression levels. Similar to the PCA results, bone marrow and spleen clustered with monocytes, while skeletal muscle and heart muscle grouped together and were distinct from smooth muscle. Thus, for any given cell type, e.g., a neuron, epigenetic marks reflect both the prior (e.g., state in the germ layer and derived cell lineages) and present regulatory landscapes.

Differential Gene Expression of Cells and Tissues

In heart and skeletal muscle, 455 out of 12,044 genes are differentially expressed (phylogenetic analysis of variance (ANOVA) P value≤0.01) compared with other cells and tissues. Approximately 44% of these genes were associated with the tricarboxylic acid (TCA) cycle and respiration, in agreement with the metabolic organization and energy sources of these tissues.

Neurons, which are critical for cognitive and motor functions, have cell lifespans that likely exceed the lifespan of the organism. Comparing neurons to shorter-lived cells and tissues is conceptually similar to comparing gene expression of long-lived mammals to related short-lived species, e.g., examining African mole rats against other rodents. 15 Accordingly, neurons should possess a gene expression signature associated with low turnover/long lifespan, in addition to the patterns indicative of neuronal function. Out of 12,044 genes 1,438 were differentially expressed in neurons (P≤0.01) and gene set enrichment analysis showed enrichment for functions associated with lysosomes, proteasomes, ribosomal proteins and apoptosis. Neurons presented with reduced expression of 27 ribosomal proteins and multiple 20S proteasome subunit genes, consistent with distinct protein metabolism required to fine-tune self-renewal and synaptic plasticity. This group of genes was not correlated with cell and tissue turnover, suggesting that this expression pattern is unique to long-lived neurons. Reduced protein metabolism, which may be induced by dietary restriction and other interventions, is known to associate with extended lifespan in a number of model organisms. Furthermore, expression of the tumor suppressor p53 (TP53) was significantly reduced (P≤0.001) in neurons, where it was expressed at a level gene expression pattern of cell and tissue turnover.

Inputs to Machine Learning Platform and iPANDA

In a preferred embodiment, a general design of the computational procedures that outputs drug classification of the invention are in four sequential steps: 1) transcriptomic similarity search, 2) protein target based search, 3) structural similarity based search, 4) transcriptomic signature screening and 5) deep neural network based search.

Regarding (1) In silico Pathway Activation Network Decomposition Analysis (iPANDA), can be applied to transcriptomic tissue-specific aging datasets obtained from Gene Expression Omnibus (GEO) with total number of samples not less than 250 for each tissue. Tissue-specific cellular senescence pathway marker sets are identified. Only pathways considerably perturbed in senescent cells (pathways with iPANDA-generated p-values less than 0.05 are considered as pathway markers). iPANDA scores are precalculated for Broad Institute LINCS Project data and were utilized for calculating transcriptomic compound similarity. Euclidian or other similarity between vectors of iPANDA scores for senolytics and other compounds of interest are calculated using data on cell lines for corresponding tissue. Only previously identified tissue-specific pathway markers were used for similarity calculation.

Regarding 2) Using LINCS Project data on knockdown cell lines the same procedure are performed to identify key target genes involved in the action of previously identified senolytic compounds D (Dasantinib), N (Navitoclax) and Q (Quercetin). The list of target genes is enriched by proteins likely to interact with these compounds using STITCH human drug-target interaction database. Pharmacophore-based search and publicly available docking algorithms are applied to identify the compounds which specifically bind the identified targets with highest affinity.

3) Structural similarity search is performed for three compounds already known to have senolytic properties (D,N,Q). Using publicly available molecular docking algorithms the importance weights for chemical groups were defined. This information is utilized for QSAR-based structure generation and filtering. Compounds from pubchem database can also be screened during the similar procedure in order to find structural analogues of D, N and Q.

4) To investigate potential effects of natural compounds without known molecular targets GEO and LINCS Project gene expression data are used. In both databases, datasets can be examined, consisting of transcriptomes of cell lines before and after treatment with multiple different chemical compounds. For aging datasets scoring exactly the same GEO datasets GSE66236, GSE69391, GSE18876, GSE21779, GSE38718, GSE59980, GSE52699, GSE48662 are used. It can be assumed that an anti-aging compound would affect an aged transcriptome to turn it into "younger" state. Mechanistically, this reflected a fact that if a certain regulatory pathway is increased (or decreased) with aging, its end targets would increase (or decrease) expression with aging. By searching for compounds which decrease (or increase) the expression of those end targets, the drugs which target these aging-associated pathways (some of its master regulators) could be discovered.

First, differentially expressed genes associated with aging are found, as well as differentially expressed genes after drug treatment. For microarray-based transcriptome data, a limma test of differential gene expression is used. Each set of differentially expressed genes is ordered accordingly to the following measure which takes into account both magnitude and statistical significance of the effect: FC max(0, −log(pvalue)), where PC is fold-change of gene expression between groups and pvalue represents the result of limma test.

A statistically motivated score estimating anti-aging abilities of a compound is designed. A significantly up- or down-regulated gene were defined as the ones with FDR<0.01 (after multiple-testing correction). A Fisher exact test is performed which measured the association of two characteristics of each gene: being significantly downregulated after the drug treatment and being significantly upregulated during aging. Vice versa, the same test is performed for significantly upregulated genes after the drug treatment versus significantly downregulated genes during aging. The best of p-values of those two tests are taken as a score for the given drug against aging. A multiple testing correction of the obtained p-values for the amount of compound under study can be performed. The same methodology is applied for screening natural compounds within LINCS transcriptomic database that are similar to the effects of other drugs, such as metformin.

5) The deep neural network based classifier of compound pharmacological class can be trained on many compounds. Training data included structural data (QSAR, SMILES), transcriptomic response LINCS Project data on gene-level and pathway level (iPANDA) and drug-target interaction network from STITCH database. The specific class of prospective senolytic compounds is declared during training. This class included compounds identified on the steps 1, 2, 3 of the study.

Established classifier accuracy is recorded after the class-balancing of the test 10 set. A list of senolytic compounds after scanning the database of 300000+ compounds is obtained for further analysis. Top ranking compounds are obtained on each of the steps and intersection is found for each tissue independently. As a result compounds are identified as having the best senolytic properties for the tissue. A set of structural analogues according to the procedure in step 3 is obtained, which possess similar molecular properties, and likely senolytic properties.

6) Finding structural analogs of desired molecules. An aim also is to find structural analogs of molecule of interest for protein-ligand interaction. This approach is highly efficient for increasing the specificity of binding with targets (proteins).

At the first step we provide an analysis of possible targets for the drug compounds. This can be done in two ways: 1) using specific programs for searching in databases for different interactions of molecules of interest with proteins/genes (e.g. STITCH); 2) article analysis of an experimental data. In the case of a molecule chosen the second way as it helps to select the best variants of experimentally approved protein-ligand interactions. From literature analysis n targets are chosen according to parameters: 1) specific binding of target with drug(s); 2) the lowest IC50; 3) the presence of the structure in protein data bank.

After that for all of the structures we applied docking for all possible active sites and additional pockets of binding. The best positions of drugs in target were chosen and after an additional docking is done with the usage of algorithm of flexible chains.

Then all the structures of the target were analyzed according to algorithm: 1) amount of hydrogen bonds 2) hydrophobic/hydrophilic interactions 3) number n-n interactions. This information were used further to understand the key principles by which molecule can bind into the specific site of the target. According to such analysis one can find the rules for a molecule to be modified in for better binding properties with specific target. With the usage of the software the analogs are found according to the rule for the molecule. After that toxicology in silico test are provided with choosing non-toxic analogs. These new non-toxic analogs were again docked into the binding site of the target for interactions analysis and those which showed the best score results are selected as most promising and perspective ones. Other structural analogs and conformers can be extracted from the Pubchem Database.

In a preferred embodiment, a deep neural network, similar to that described in, for example, Aliper et. al., "Deep learning applications for predicting pharmacological properties of drugs and drug repurposing using transcriptomic data", Mol Pharm, 2016 Jul. 5; 13(7): 2524-2530, and Mamoshina et. al., "Applications of Deep Learning in Biomedicine", Mol Pharm, 2016 Mar. 13 (5), is used, in combination with a cellular signature database such as the LINCS database and a drug therapeutic use database such as MeSH, as inputs to the DNN in order to output drug classifications to develop a therapeutic protocol, in this case to categorize and choose drugs for a senescence or other treatment protocol. LINCS is the US Library of Network-Based Cellular Signatures Program aims to create a network-based understanding of biology by cataloging changes in gene expression and other cellular processes that occur when cells are exposed to a variety of perturbing agents. MeSH is (Medical Subject Headings) is the US National Library of Medicine controlled vocabulary thesaurus used for indexing articles for PubMed, the free search engine of references and abstracts on life sciences and biomedical topics also from the US National Library of Medicine.

An AAE works by matching the aggregated posterior to the prior ensures that generating from any part of prior space results in meaningful samples. As a result, the decoder of the adversarial autoencoder learns a deep generative model that maps the imposed prior to the data distribution. An AAE can be used in applications such as semi-supervised classification, disentangling style and content of images, unsupervised clustering, dimensionality reduction and data visualization. AAEs are used, for example, in generative modeling and semi-supervised classification tasks. Thus an AAE turns an autoencoder into a generative model. The AAE is often trained with dual objectives—a traditional reconstruction error criterion, and an adversarial training criterion that matches the aggregated posterior distribution of the latent representation of the autoencoder to an arbitrary prior distribution.

In a preferred embodiment derived from (4) Kadurin, the method uses a 7-layer AAE architecture with the latent middle layer serving as a discriminator. As an input and output the AAE uses a vector of binary fingerprints and concentration of the molecule. In the latent layer we also introduced a neuron responsible for growth inhibition percentage, which when negative indicates the reduction in the number of tumor cells after the treatment. To train the AAE one uses a cell line assay data for compounds profiled in a cell line. The output of the AAE can then be used to screen drug compounds, such as the 72 million compounds in PubChem, and then select candidate molecules with potential anti-senescent or properties.

The latest class of non-parametric approaches for deep generative models is known as generative adversarial network (GAN). In this new framework, initially proposed by Goodfellow, generative models are estimated via an adversarial process. In practice, two models are simultaneously trained: a generative model G that captures the data distribution, and a discriminative model D that estimates the probability that a sample came from the training data rather than G. The training procedure for G is to maximize the probability of D making an error. Thus, this framework does not correspond to the standard optimization problem as it is based on a value function that one model seeks to maximize and the other seeks to minimize. The process terminates at a saddle point that is a minimum with respect to one model's strategy and a maximum with respect to the other model's strategy. Because GANs do not require an explicit representation of the likelihood, neither approximate inference nor Markov chains are necessary. Consequently, GANs provide an attractive alternative to maximum likelihood techniques.

Generative capabilities of deep adversarial network techniques open the doors to new perspectives as it could contribute to overcome several limitations of current data driven computational methods. For example, we can apply GANs on transcriptomics data for the generation of new samples for a desired phenotypic groups and in chemoinformatics for the prediction of the physical, chemical, or biological properties and structures of molecules. Quantitative structure-activity relationships (QSAR) and quantitative structure-property relationships (QSPR) are still considered as the modern standard for predicting properties of novel molecules. To that end, many ML-based approaches have been developed to tackle such problems, but recent results show that the DL-based methods match or outperform other state-of-the-art methods and demonstrate better predictive performance, parsimony and interpretability and web-based predictors are available on some cases. Furthermore, new methods based on convolutional neural networks are able to perform predictions by directly using graphs of arbitrary size and shape as inputs rather than fixed feature vectors and one can expect to see the development of more flexible deep generative architectures that can be applied directly to other structured data such as sequences, trees, graphs, and 3D structures. Thus, the deep adversarial network techniques could be used to improve accuracy, generative capabilities and predictive power and address several issues including computational cost, limited computation at each layer and limited information propagation across the graph.

Target prediction and mapping of bioactive small compounds and molecules by analyzing binding affinities and chemical properties is another area of research that makes extensive use of data-driven computational methods in order to optimize the use of data available in existing repositories. Despite promising results and the availability of web-platforms to computationally identify new targets for uncharacterized molecules or secondary targets for known molecules such as SwissTargetPrediction, in general, the available methods remain too inaccurate for systematic binding predictions and physical experiments remain the state of the art for binding determination. In this field, DL-based methods, such as the recently released methods AtomNet based on deep convolutional neural networks have allowed to circumvent several limitations and outperform more traditional computational methods including RFs, SVMs for QSAR and ligand-based virtual screening. One can expect that the development of DL-methods making use of the GAN framework will also lead to significant improvement with respect to prediction accuracy and power.

In a preferred embodiment, the adversarial network and the autoencoder are trained jointly with SGD in two phases—the reconstruction phase and the regularization phase—executed on each mini-batch. In the reconstruction phase, the autoencoder updates the encoder and the decoder to minimize the reconstruction error of the inputs. In the regularization phase, the adversarial network first updates its discriminative network to tell apart the true samples (generated using the prior) from the generated samples (the hidden codes computed by the autoencoder). The adversarial network then updates its generator (which is also the encoder of the autoencoder) to confuse the discriminative network. Once the training procedure is done, the decoder of the autoencoder will define a generative model that maps the imposed prior of $p(z)$ to the data distribution.

In a preferred embodiment, the input layer is divided into a fingerprint part and a concentration input neuron. In a preferred embodiment, an AAE is trained to encode and reconstruct not only molecular fingerprints, but also experimental concentrations. The Encoder consists of two consequent layers L1 and L2 with 128 and 64 neurons, respectively. The decoder consists of the two layers L'1 and L'2, comprising 64 and 128 neurons respectively. The latent layer consists of 5 neurons, one of which is the GI and the four others are discriminated with normal distribution. Since we train an encoder net to predict 'efficiency' against 'senescence' in a single neuron of latent layer, we divide the latent vector in two parts—'GI' and 'representation'. So we added a regression term to the encoder cost function. Furthermore, we restrict our encoder to map the same fingerprint to the same latent vector independently from input concentration by additional 'manifold' cost. Here we compute mean and variance of the concentrations through all dataset and then use them to sample concentrations for 'manifold' step. On each step we sample fingerprint from the training set and batch of concentration from normal distribution with given mean and variance. The training net with 'manifold' loss is performed by maximization of cosine similarity between 'representations' of similar fingerprints with different concentrations All these changes resulted in a 5-step train iteration instead of a 3-step in AAE basic model: (a) Discriminator trained to distinguish between given latent distribution and encoded 'representation', (b) Encoder trained to confuse Discriminator with generated 'representations', (c) Encoder and Decoder trained jointly as Autoencoder; (d) Encoder trained to fit 'score' part of latent vector; (e) Encoder trained with 'manifold' cost.

The two first steps (a,b) are trained as usual adversarial networks. The Autoencoder cost function is computed as a sum of logloss of fingerprint part and mean squared error (MSE) of concentration parts and MSE is also used as a regression cost function. Example code for a preferred AAE is available at github dot com/spoilt333/onco-aae.

Experimental/Simulations/Models

1. Single Biopsy (or Existing Individual Profile).

Single biopsy test of liver or lung is taken from the patient according to standard procedures in medical center as described in in the nhlbi.hih.gov website. For a lung biopsy, few samples of lung tissue from several places in lungs will be taken. The samples are examined under a microscope, transcriptome and gene expression profiles are also analyzed. This procedure can help rule out other conditions, such as sarcoidosis, cancer, or infection. Lung biopsy also can show how far disease has advanced.

There are several procedures to get lung tissue samples.

Video-assisted thoracoscopy. This is the most common procedure used to get lung tissue samples. An endoscope is inserted with an attached light and camera into chest through small cuts between ribs. The endoscope provides a video image of the lungs and allows to collect tissue samples. This procedure must be done in a hospital.

Bronchoscopy. For a bronchoscopy, a thin, flexible tube through is passed in nose or mouth, down a throat, and into airways. At the tube's tip are a light and mini-camera. They allow to see windpipe and airways. Then a forceps is inserted through the tube to collect tissue samples.

Bronchoalveolar lavage. During bronchoscopy, a small amount of salt water (saline) is injected through the tube into lungs. This fluid washes the lungs and helps bring up cells from the area around the air sacs. These cells are examined under a microscope.

Thoracotomy. For this procedure, a few small pieces of lung tissue are removed through a cut in the chest wall between ribs. Thoracotomy is done in a hospital.

For a liver biopsy, few samples of liver tissue from several places in liver will be taken. The samples are examined under a microscope, transcriptome and gene expression profiles are also analyzed.

There are several procedures to get live tissue samples.

Percutaneous Liver Biopsy. The health care provider either taps on the abdomen to locate the liver or uses one of the following imaging techniques: ultrasound or computerized tomography (CT) and will take samples with the needle.

Transvenous Liver Biopsy. When a person's blood clots slowly or the person has ascites—a buildup of fluid in the abdomen—the health care provider may perform a transvenous liver biopsy. A health care provider applies local anesthetic to one side of the neck and makes a small incision there, injects contrast medium into the sheath and take an x ray. After this insert and remove the biopsy needle several times if multiple samples are needed.

Laparoscopic Liver Biopsy. Health care providers use this type of biopsy to obtain a tissue sample from a specific area or from multiple areas of the liver, or when the risk of spreading cancer or infection exists. A health care provider may take a liver tissue sample during laparoscopic surgery performed for other reasons, including liver surgery.

2. Pathway Signature Measurement

Transcriptomic Data:

From the GEO database (ncbi.nlm.nih dot gov/geo/) data sets containing gene expression data related to IPF patients and normal healthy lung tissue used as a reference were downloaded (21 data sets). IPF and normal data from different data sets was preprocessed using GCRMA algorithm and summarized using updated chip definition files from Brainarray repository for each data set independently.

Differential genes were calculated using limma and deseq2 algorithms for groups of comparison: IPF (IPF vs reference healthy lung tissue); Senescence (old vs reference young healthy lung tissue); Smoking (current smoker vs reference non-smoker); Age status data was available for 2 data sets and smoking status data was available for 1 data set.

Differential expression genes data was used as an input for iPANDA algorithm in order to measure the pathway signature of each comparison group.

Pathway Database Overview:

There are several widely used collections of signaling pathways including Kyoto Encyclopedia of Genes and Genomes, QIAGEN and NCI Pathway Interaction Database. In this study, we use the collection of signaling pathways most strongly associated with various types of malignant transformation in human cells obtained from the SABiosciences collection (sabiosciences dot com/pathwaycentral dot php).

3. Compare Signature Profiles.

Signature profile for each comparison group can be constructed based on iPANDA (FIG. 2) p-values cut-off (p-value<=0.05) and common overlap among different data sets: intersection cut-off threshold equal to 15 was used for IPF data, 2 for senescence data and 1 for smoking data.

Figure 2:
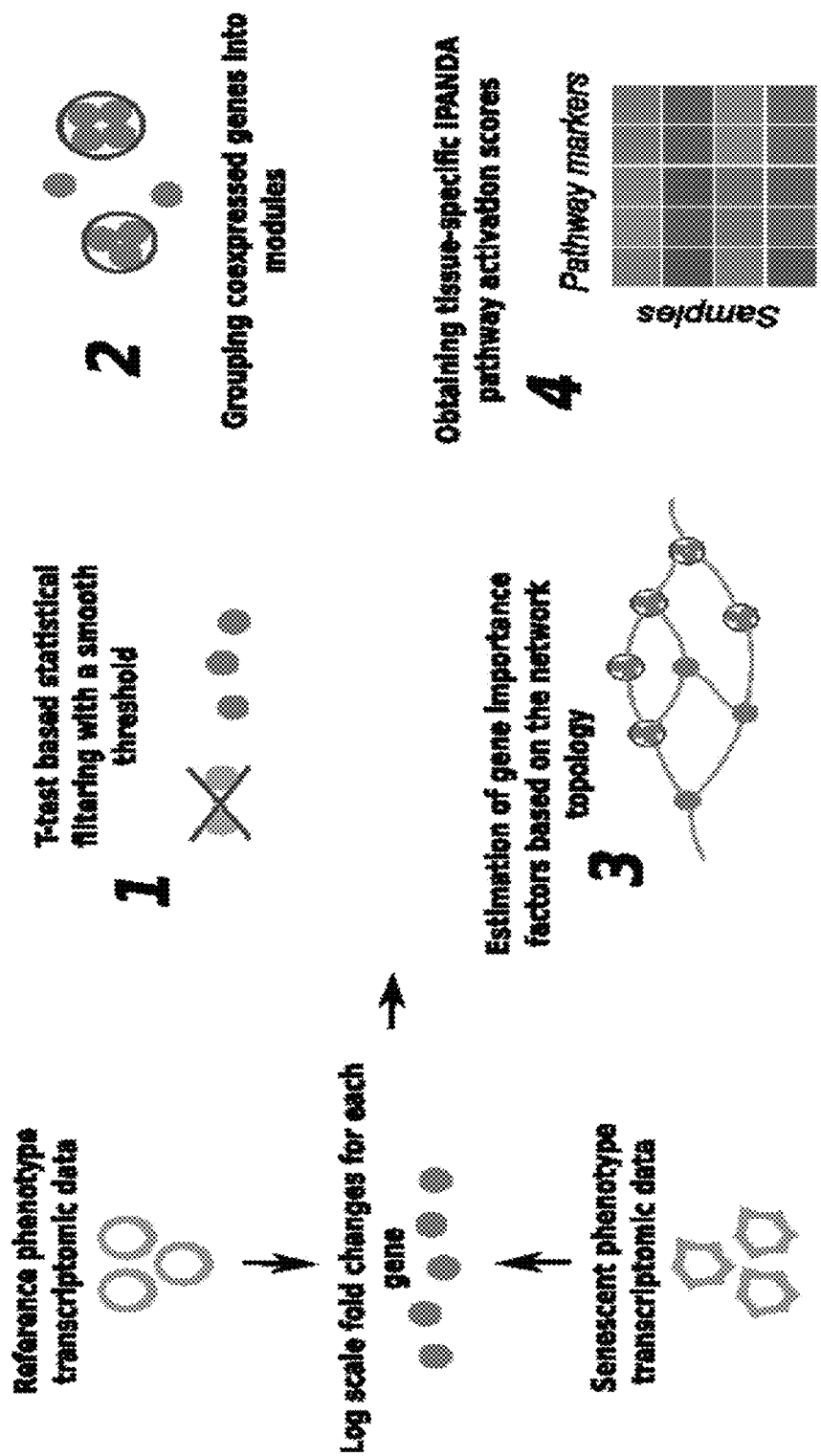
FIG. 2 shows the general scheme of an iPANDA calculation pipeline.

FIG. 2 shows the general scheme of an iPANDA calculation pipeline. Fold changes between the gene-expression levels in the samples under investigation, and an average expression level of samples within the normal set serves as input data for the iPANDA algorithm. The major steps of iPANDA algorithm include estimation of statistical weights (1), co-expression-based grouping of genes into modules (2), estimation of topological weights (3) and calculation of iPANDA pathway activation scores (4).

4. Personalize the Treatment.

DNNs can be used as a tool to predict active compounds and generate a compounds with a desired efficacy. The application of DNN-based models can be used for personalization of compounds for individual patients and evaluation of the treatment efficacy and safety.

Machine learning approaches provide the tools of the analysis of biomedical data without prior assumption on the functional relations of this data. And Deep Neural Network (DNN) based approaches, such as multi-layered feed forward neural networks, are able to fit the complex and sparse biomedical data and learn highly non-linear dependencies of the raw data without the modification of features of interest. And deep learning is a state of the art method for many task from machine vision to language translation. But despite the fact, that biomedicine entered the era of "big data", biomedical datasets are usually limited by sample sizes. And feature selection and dimensionality reduction of the feature space usually increase the predictive power of the DNNs applied in the biomedical domain (Aliper, Plis, et al. 2016).

A system can be provided that utilizes quantitative models with a deep architecture that is able to stratify compounds by their efficacy for the individual patient based his or her personal profile. In part, the personal profile can include the biological pathways analyzed with the quantitative models. The following data could be used as input feature to the system: gene expression profiles and signaling pathway profiles, blood tests (Putin et al. 2016), protein expression profiles, clinical history as well as a deep representation of the electronic health record (Miotto et al. 2016).

A system can be provided that utilizes the quantitative models with a deep architecture that is able to evaluate the efficacy of the proposed treatment through the quantitative assessment of the health status of the patient, such a biological age, life expectancy, the probability of survival. The following data could be used as input feature to the system: gene expression profiles and signaling pathway profiles, blood tests, protein expression profiles, clinical history as well as a deep representation of the electronic health record.

A system can be provided that utilizes the quantitative models with a deep architecture that is able to predict potential side effect of the treatment. The following data could be used as input feature to the system: gene expression profiles and signaling pathway profiles, blood tests, protein expression profiles, clinical history as well as a deep representation of the electronic health record.

A system can be provided based on generative model with deep architecture (Kadurin et al. 2017) that is able to generate molecules with a desired properties, such as high efficacy, low toxicity, high bioavailability and the like. Generated molecules can be evaluated by the DNN based systems through the efficacy and safety prediction.

Incubate Compound: Test in Laboratory for Effectiveness and Identification, Design Therapy.

Treatment:

According to (Raghu et al. 2015) ATS/ERS/JRS/ALAT Clinical Practice Guideline there are just a few agents recommended for IPF treatment: Nintedanib, a tyrosine kinase inhibitor with multiple targets, Conditional recommendation for use; Pirfenidone, inhibits TGF-β stimulated collagen production and reduces the production of fibrogenic mediators such as TGF-β, reduce production of inflammatory mediators such as TNF-α and IL-1β in both cultured cells and isolated human peripheral blood mononuclear cells, Conditional recommendation for use; Macitentan, bosentan, Dual endothelin receptor antagonists, Conditional recommendation against use; and Sildenafil, phosphodiesterase-5 inhibitor, Conditional recommendation against use.

Some of the treatments are guided not to be used: Anticoagulation (warfarin); Combination prednisone+azathioprine+N-acetylcysteine; or Selective endothelin receptor antagonist (ambrisentan).

The removal of the causative agent is the most effective intervention in the treatment of liver fibrosis. This strategy has been shown effective in most etiologies of chronic liver diseases. For patients with cirrhosis and clinical complications, liver transplantation is currently the only curative approach. Transplantation improves both survival and quality of life. However, in patients with HCV-induced cirrhosis, viral infection recurs after transplantation, aggressive chronic hepatitis develops, and progression to cirrhosis is common.

According to (Cohen-Naftaly and Friedman 2011) there are several points of attack in developing antifibrotic agents that are described in detail in the following sections: Eliminate the cause(s) of injury and their mediators; Reduce inflammation and the immune response; Target specific signaling: receptor-ligand interaction, intracellular signaling; Reduce fibrogenesis, inhibit matrix synthesis; and Resolve fibrosis by increasing scar matrix degradation, stimulating apoptosis of stellate cells, and BM or cell transplantation.

In each case the treatment is individual and obtained for every patient according to the etiology of the disease and patient condition (fibrotic stage). More information about the strategies can be found at the aasld.org website.

The present invention can provide a strategy for treatment, which is not only targeting the fibrotic conditions, but also pre-fibrotic and related/causing (e.g., cell senescence). Such approach allows a medical practitioner to increase chances for survival and decrease the speed of degradation processes or reverse of the organ.

Accordingly, a 5R strategy as described herein can be applied to patients with pre-senescent, senescent and fibrotic conditions. 5R strategy includes: Rescue; Remove; Replenish; reinforce; and Repeat, which are described as follows.

Stage 1. Rescue.

The first step of 5R strategy is rescuing pre-senescent cells in a particular tissue (including liver and lungs). Pre-senescent phenotype is considered potentially reversible. In order to rescue the cells demonstrating pre-senescent phenotype the specific set of possible interventions shall be applied. These interventions include the treatment with the one senoremediator compound or a combination of the senoremediator compounds from the list herein. Senoremediator compounds should be administered orally, by injection, sublingually, buccally, rectally, vaginally, cutaneously, transdermally, ocularly, oticly or nasally or any other way.

Stage 2. Remove.

This step is performed to eliminate the cells that already entered the irreversible senescent state. Senescent cells lose their function and possess a constant danger to the surrounding cells as described above. Elimination of such cells may prevent surrounding cells to enter the senescent phenotype by positive loop and restore the normal tissue functioning. In order to eliminate the cells demonstrating senescent phenotype the specific set of possible interventions shall be applied. These interventions include the treatment with the one senolytic compound or a combination of the senolytic compounds from the list below. Senolytic compounds should be administered orally, by injection, sublingually, buccally, rectally, vaginally, cutaneously, transdermally, ocularly, oticly or nasally or any other way.

Stage 3. Replenish.

The second step leads to the general rejuvenation of the cells in the population, but on the other hand, to the reduction in the total cell count. This allows for the further replenish step to be used for repopulation of the tissue with functional cells. Therefore the pool of stem/progenitor cells in a particular tissue (including mesenchymal and epithelial stem cells in lungs, liver) should be activated in order to replenish the tissue. The possible interventions needed to achieve that goal include the treatment with the one specific compound or a combination of the compounds from the list below. Importantly the compounds should stimulate the proliferation of the stem cells, but on the other hand prevent the unwanted effects related to the possible uncontrolled proliferation and subsequent malignant transformation. The compounds should be administered orally, by injection, sublingually, buccally, rectally, vaginally, cutaneously, transdermally, ocularly, oticly or nasally or other method.

Stage 4. Reinforce.

This step is used to prevent the further potential degradation of the tissue (or organ). It may include the treatment with the one specific compound or a combination of the compounds from the list below. These compounds should demonstrate one of the following activities: immunomodulation in order to prevent possible malignant transformation and the accumulation of the senescent cells, cytoprotection in order to retain the functional state of the tissue, stimulation of the macrophages in order to achieve the specific state of senophagy (ability to specifically engulf and digest senescent cells). The compounds should be administered orally, by injection, sublingually, buccally, rectally, vaginally, cutaneously, transdermally, ocularly, oticly or nasally or other method.

Stage 5. Repeat.

The whole multi-stage longevity therapeutics pipeline (stages l-4) can be applied recurrently. The period between the therapies is defined individually on the tissue (organ)-specific basis and may vary from 1 month to 10 years.

In an embodiment, the first four steps Rescue; Remove; Replenish; Reinforce can be used as a multi-stage longevity therapeutics pipeline and can be applied more than once, and on an ongoing basis. The period between the therapies is defined individually on a tissue, organ, and patient specific basis and may vary from 1 month to 10 years between treatments, or may essentially be continually ongoing, for some or all of the steps.

EXAMPLES

The invention includes methods, system, drugs, apparatus, computer program product, among others, to carry out the following. It includes a method of treating senescence in a patient tissue or organ.

Example 1

Assay Development and Validation for Testing Senolytic and Senoremediator Compounds in Skin and Lung The assay for senolytic and senoremediator compounds was developed based on the present invention. A set of compounds for testing was selected using tissue-specific signatures of cellular senescence obtained with the iPANDA algorithm. The compounds with previously measured transcriptional response profiles in one or more cell lines were scored (prioritized). Only significantly perturbed pathways from skin and lung cellular senescence signatures were used for scoring. For establishing a list of senolytic compound candidates the compounds similar to established senolytics (e.g., Navitoclax, Dasatinib) were selected. For establishing a list of senoremediator compound candidates the compounds demonstrating the reversed effect on the pathways under consideration comparing to the senescence signatures in skin and lung were selected.

The assay development included the following steps: a) Selection of an appropriate senescence model for further compound validation; b) Selection of appropriate read-outs for compound testing; c) selecting compounds showing significant response in senolytics assay; and d) selecting compounds showing significant response in senoremediation assay.

Step a) can include selection of an appropriate senescence model for further compound validation, such as: Replicative senescence. Somatic cells proliferate until they reach an irreversible growth arrest. Senescence occurs by simple subculturing of primary cells; Oxidative stress induced senescence. Cells undergo a transient stage of senescence by chemical (e.g. $H_2O_2$); Irradiation-induced senescence. Cells undergo a transient stage of senescence by irradiation (e.g. UVA, UVB, IR); Drug-induced senescence. Low nanomolar concentration-treatments with mitomycin-C (MMC), a DNA inter- and intra-crosslinking agent; and Paracrine senescence. Use conditioned medium from the drug-induced (MMC) senescence induction technique.

Primary human dermal fibroblasts and human lung fibroblasts (WI-38) were selected as a model cell lines for the assay. Senescent cells differ from their proliferative counterparts (e.g. morphology, β-galactosidase activity, oxidative stress, proliferation activity). The tests showed that MMC treated cells and cells cultured in conditioned medium from the MMC-treated cells senescence applied can be used as a model of senescence for senolytic/senoremediation assay based on the set of readouts tested.

Step b) can include selection of appropriate read-outs for compound testing. The following read-outs were tested in MMC treated cells using Navitoclax as senolytic positive control and nicotinamide mononucleotide (NMN) as senoremediation positive control (FIG. 3). FIG. 3 provides information for read-outs for senolytic and senoremediation compound validation.

Step 3 c) can include selecting compounds that have shown significant response in senolytics assay, such as: Withaferin A, Argatroban, Flavopiridol, and Linifanib.

Step d) can include selecting compounds that have shown significant response in senoremediation assay, such as: Withaferin A, Lavendustin, and Sulforaphane.

The following is a description of the assay and validation process:

1. Cell Culture and MMC-Induced Senescence.

Human dermal fibroblasts (HDFs, CellnTec) were maintained in DMEM/F-12 Ham (Sigma) supplemented with 10% FCS (Sigma) and 1% P/S (Sigma). Cells were thawed and used at low passages (P3-P8).

Figure 5:
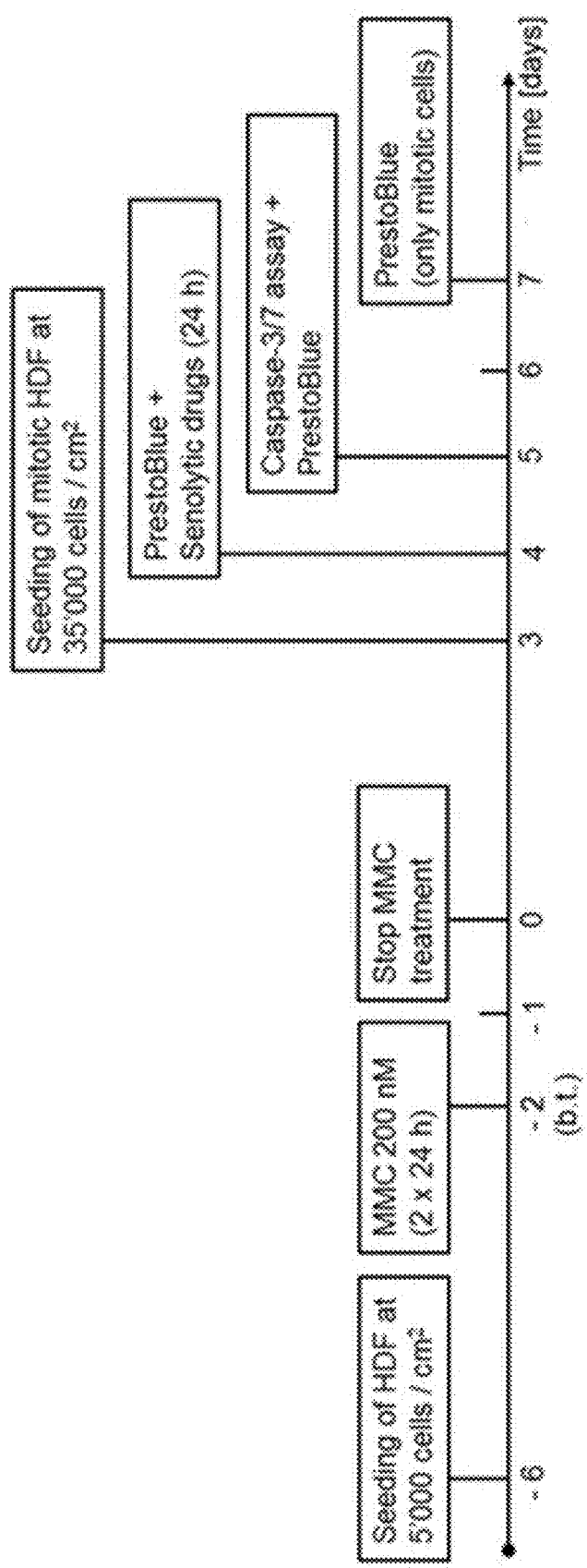
FIG. 5 shows the timeline of senolytic drugs validation.

On day −9, 1 Mio cells were thawed and allowed to adhere and grow. Then on day −6 (FIG. 5) cells were seeded at a concentration of 5,000 cells/$cm^2$ into two 96-well plates (1x caspase assay, 1x PrestoBlue). Remaining cells were further cultivated (mitotic cells control) and seeded the day before treatment (day 3) at a concentration of 35,000 cells/$cm^2$ into 96-well plates. FIG. 5 shows the timeline of senolytic drugs validation.

Mitomycin-C (MMC, Sigma) was dissolved in water (pH 7.02, sterile filtered) and then further diluted in culture medium to a final concentration of 200 nM. On day −2 plated cells were treated with MMC for two consecutive days, replacing the medium after 24 h with fresh MMC-containing medium. After 48 h (day 0) MMC treatment was stopped by washing with PBS and addition of fresh culture medium.

2. PrestoBlue Assay and Caspase-3/7 Assay.

On day 4 a total of four 96-well plates were ready for senolytic drug testing (2× MMC-treated cells and 2× mitotic cells, each 1× PrestoBlue and 1× caspase-3/7 assay). Senolytic drugs were first tested at five concentrations (10, 56, 316, 1778 and 10000 nM, n=3) and were re-evaluated at an optimized concentration range if drugs showed interesting properties.

Metabolic activity of cells was evaluated before, directly after and two days after the senolytic drug treatment. PrestoBlue (Invitrogen) was diluted in culture medium and fluorescence intensity was determined at Ex./Em. 550/590 nm after 45 min.

After senolytic drug treatment cells were washed with HMS+5 FCS (wash solution), followed by CellEvent Caspase-3/7 (Invitrogen) staining (6 µM) at 37° C. for 1 h. The staining solution was removed and cell were fixed in formalin at room temperature for 15 min. Cellular DNA was stained with DAPI (1 µg/mL) for 10 min in the dark. Then cells were washed with wash solution and topped with a thin layer of wash solution in order to keep them at 4° C. overnight.

Images were taken on an inverted epifluorescence microscope (Zeiss) equipped with DAPI and FITC filter cubes. At a magnification of 10×, 3 images/well were taken (total of 9 images/drug and concentration). Acquired images were analyzed using ImageJ with the "Analyze particles" feature.

3. Exemplary Result for the Compound (INSSEN17)

Figure 6A:
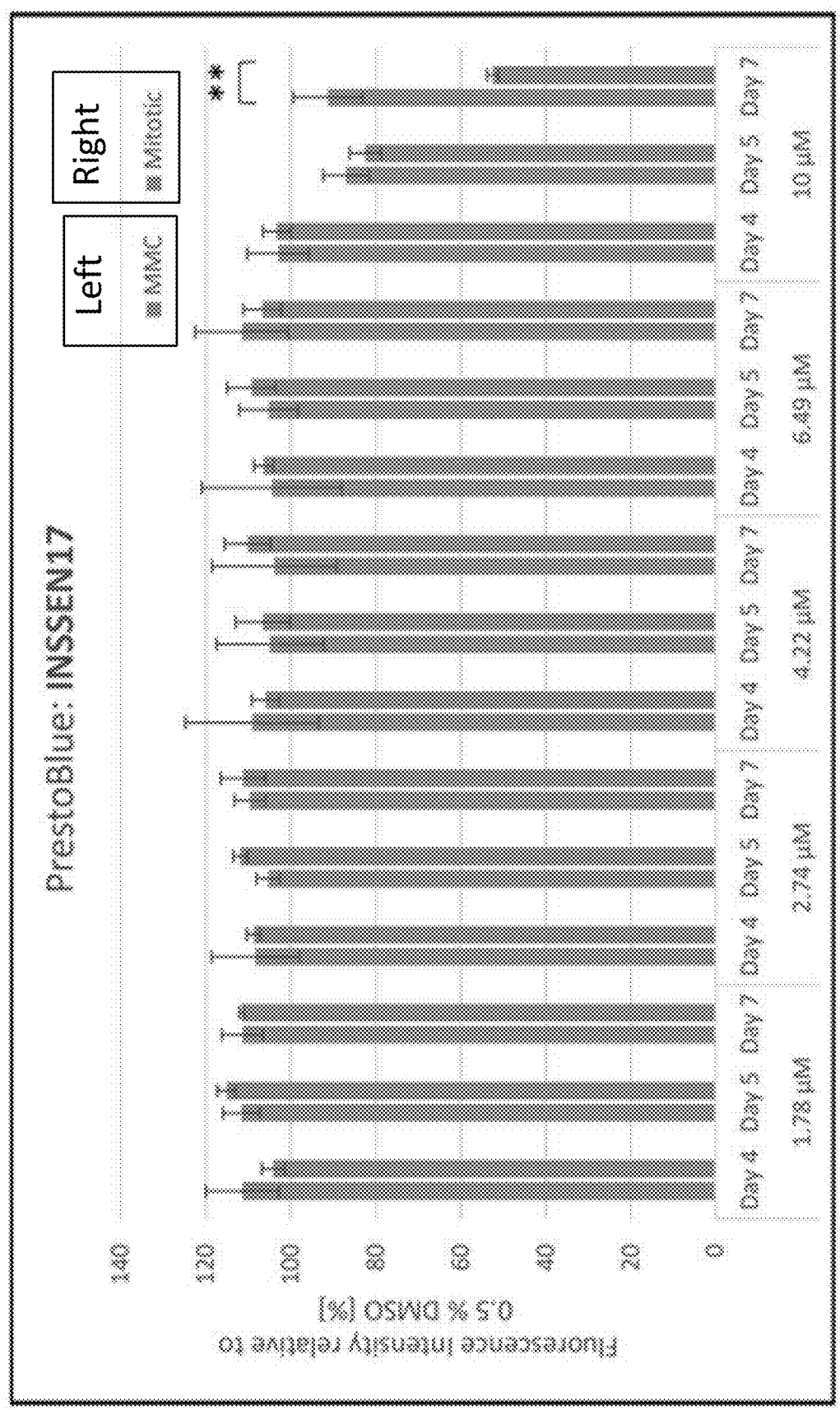
FIG. 6A shows the PrestoBlue results of INSSEN17 treated cells for all five tested concentration ranges prior (day 4) after (day 5) and two days after the treatment (day 7).

FIG. 6A shows the PrestoBlue results of INSSEN17 treated cells for all five tested concentration ranges prior (day 4) after (day 5) and two days after the treatment (day 7). INSSEN17 did not affect the metabolic activity of either, MMC-treated (blue bars) and mitotic cells (orange bars), up to a concentration of 6.49 µM. Slight cytotoxic effects started to appear at 10 µM which dropped the metabolic activity of MMC-treated and mitotic cells to 80-90% after the treatment. While MMC-treated cells stagnated in metabolic activity on day 7, mitotic cells dropped by another 30% in comparison to the DMSO controls. FIG. 6A shows the PrestoBlue results of INSSEN17. Statistic: Student's t-test (two-sided, unpaired, unequal variances): $p \leq 0.01$, *$p \leq 0.001$. Error bars are 95% confidence intervals of the mean.

Figure 6B:
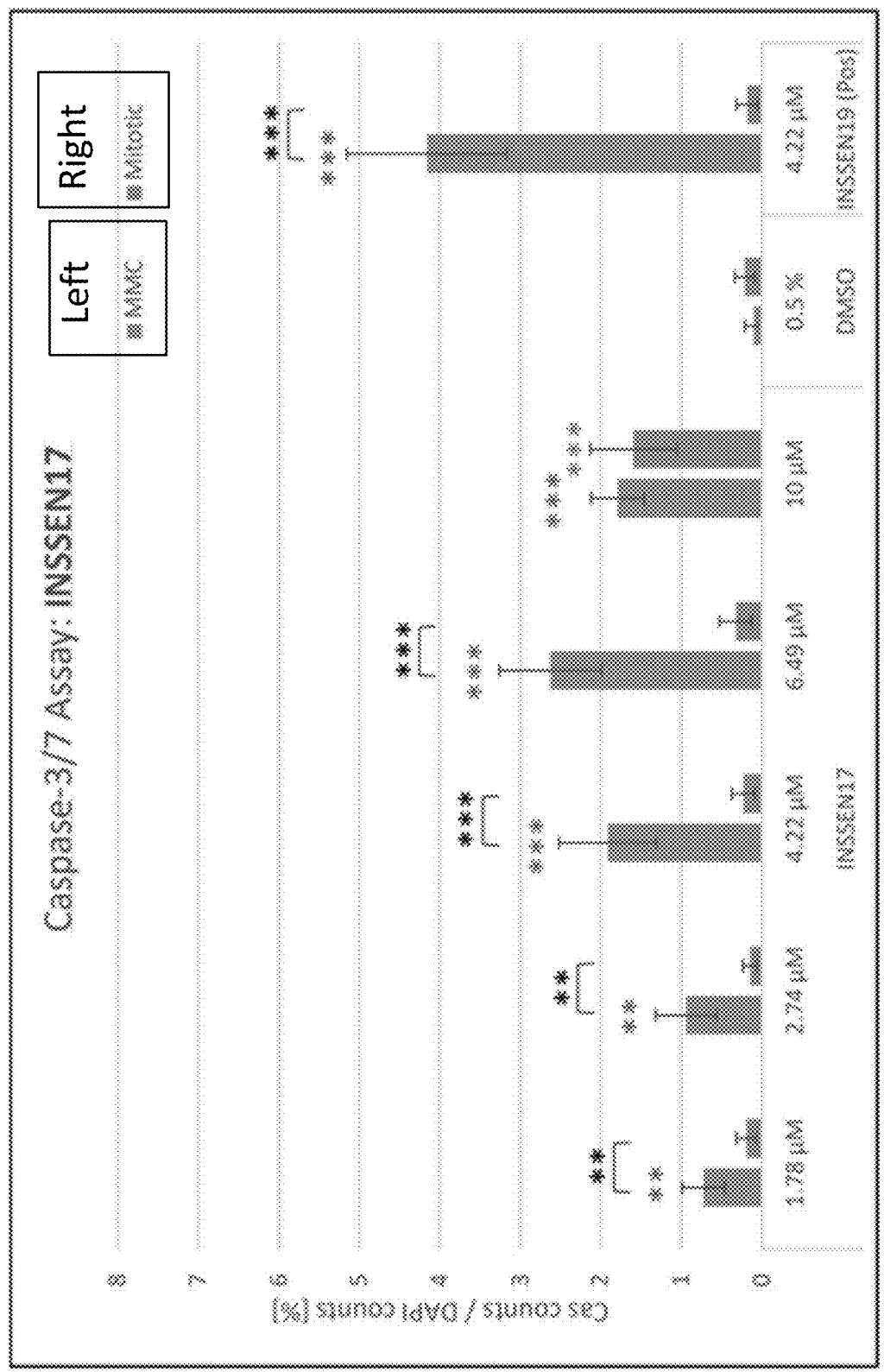
FIG. 6B shows a favorable concentration-dependent increase in caspase-positive MMC-treated cells up to a concentration of 6.49 µM while significantly differing from the mitotic cells.

Caspase-3/7 assay (FIG. 6B) showed a favorable concentration-dependent increase in caspase-positive MMC-treated cells up to a concentration of 6.49 µM while significantly differing from the mitotic cells. At the same time mitotic cells did not differ from the mitotic DMSO control. The increase in caspase-positive MMC-treated cells could not be supported by the PrestoBlue assay.

INSSEN17 exhibited a moderate to good senolytic activity in comparison to the Navitoclax positive control (2.5% vs. 4% caspase-positive cells). Even though PrestoBlue assay did not support this message, it suggested that there are no toxic effects concerning the overall metabolic activity of the cells up to a concentration of 6.49 µM.

Looking at the current results, INSSEN17 comes close to the positive control and should definitely be considered as a possible senolytic drug for further evaluations.

Example 2

Analysis with iPanda of Single Biopsy (or Existing Individual Profile) of the Tissues Four pathways are disregulated in opposite directions among IPF and senescence groups: two pathways related to hormone signaling (via SRF, ELK1, STAT5B, STAT1, STAT3 and CEBPD) and Tie2 signaling are upregulated in senescence data and downregulated in IPF data; four pathways (Cellular Apoptosis Pathway, NCI Validated transcriptional targets of deltaNp63 isoforms (Main Pathway, pathway degradation of TP63)) are downregulated in senescence data compared to IPF. Syndecan-4 mediated signaling tend to be upregulated in IPF data compared to senescence data. CXCR4 signaling, PTEN signaling (adhesion or migration, Ca2+ signaling, angiogenesis and tumorigenesis branches), SMAD2-SMAD3-SMAD4 transcriptional regulation signaling and collagen biosynthesis and choline metabolism seem to be upregulated in both groups of comparison. Four pathways related to syndecan-1 mediated cell adhesion, invasion and migration signaling seem to be the similarly upregulated in both IPF and smoking groups while 5 signaling pathways related to a particular branch of hormone signaling (via SRF, ELK1, STAT5B, STAT1, STAT3 and CEBPD), sphingolipid metabolism, Spry regulation of FGF signaling, type-1 hemidesmosome assembly seem to be disregulated in opposite directions between two groups.

Figure 4:
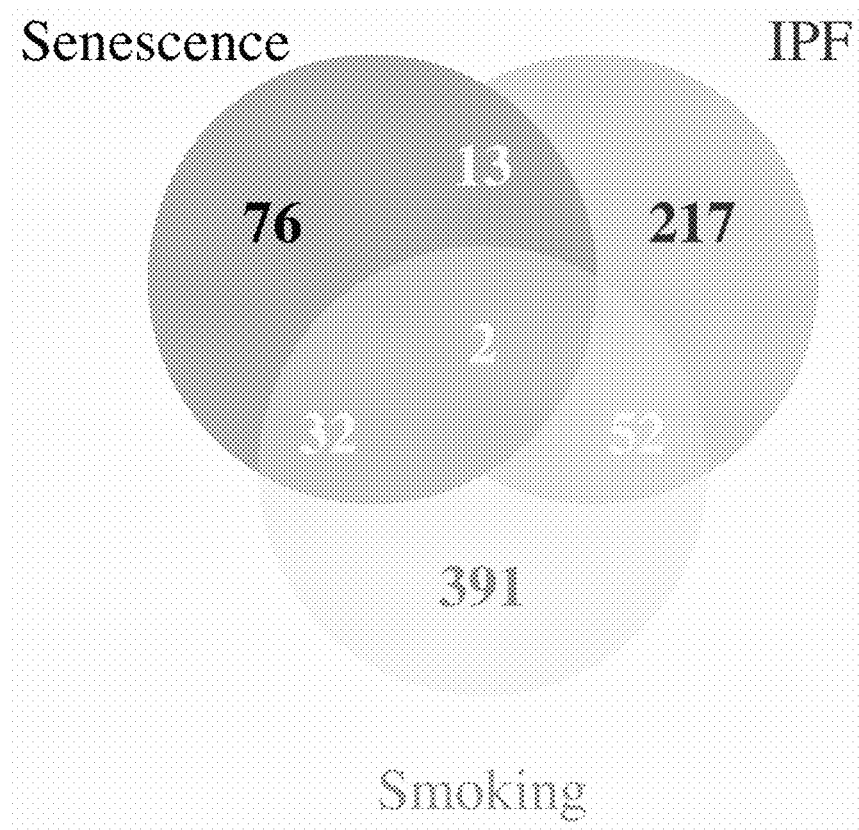
FIG. 4 shows a Venn diagram of iPANDA signature pathways for each group of comparison.

IPF and smoking comparison overlap data is presented as shown in FIG. 4. Four pathways related to syndecan-1 mediated cell adhesion, invasion and migration signaling seem to be the similarly upregulated in both IPF and smoking groups while 5 signaling pathways related to a particular branch of hormone signaling (via SRF, ELK1, STATSB, STAT1, STAT3 and CEBPD), sphingolipid metabolism, Spry regulation of FGF signaling, type-1 hemidesmosome assembly seem to be disregulated in opposite directions between two groups.

Senescence and smoking comparison overlap data is presented as shown in FIG. 4. Data has nine one-way directed signaling pathways among senescence and smoking groups: seven pathways are upregulated and two pathways are downregulated. 21 signaling pathways are disregulated in opposite directions among senescence and smoking groups: 11 pathways are downregulated in senescence data while are upregulated in smoking group; 10 pathways are upregulated in senescence data while are downregulated in smoking data. Four signaling pathways seem to have indefinite status among two groups. FIG. 4. represents Venn diagram of iPANDA signature pathways for each group of comparison. FIG. 4 shows a Venn diagram of iPANDA signature pathways for each group of comparison. Two common pathways seem to be relevant for three groups of comparisons. Growth hormone signaling pathway (via SRF, ELK1, STATSB, STAT1, STAT3 and CEBPD) is upregulated in smoking and senescence data compared to downregulation in IPF data. Another pathway is Tie2 signaling: downregulated in both IPF and smoking groups and upregulated in senescence data.

The aging clock algorithm can be used to compute a personalized treatment protocol. Biological clocks are compatible with and useful for providing guidance to aging and senescent assessment and remediation. Thus, they are compatible with and useful with the current invention. Such biological aging assessment is typically a first step in aging/longevity treatment and remediation. The figures in the provisional illustrate some exampled biological aging clocks of that are useful with the current invention. In addition, while discussion of the machine learning and deep learning methods below is discussed in the context of biological aging assessment, many of the methodologies are similar to and are adapted in this invention for development of the senescent therapies, drug and otherwise, disclosed.

Figure 7:
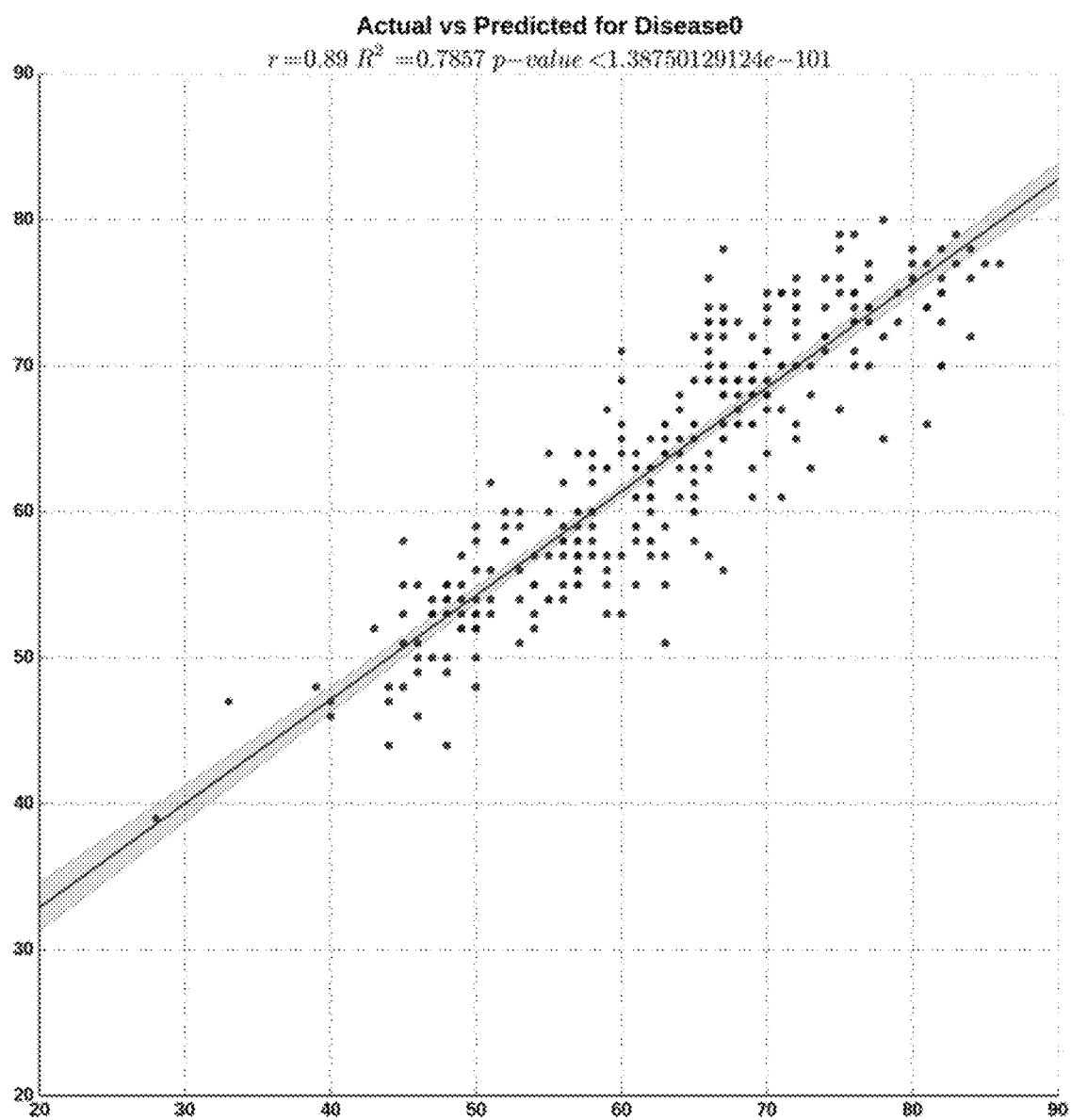
FIG. 7 illustrates a transcriptomic clock method for biological aging assessment, compatible with the current invention.

FIG. 7 illustrates a transcriptomic clock method for biological aging assessment, compatible with the current invention. The correlation between actual chronological age (x-axis) with predicted age (y-axis) for healthy individuals using the validation set. The red line represents the linear regression decision boundary line. Values for r, R2 and p-value are provided at the top of the figure. Note that the term Disease0 in this and other figures simply means healthy/control subjects were used for such biological aging assessment.

Figure 8:
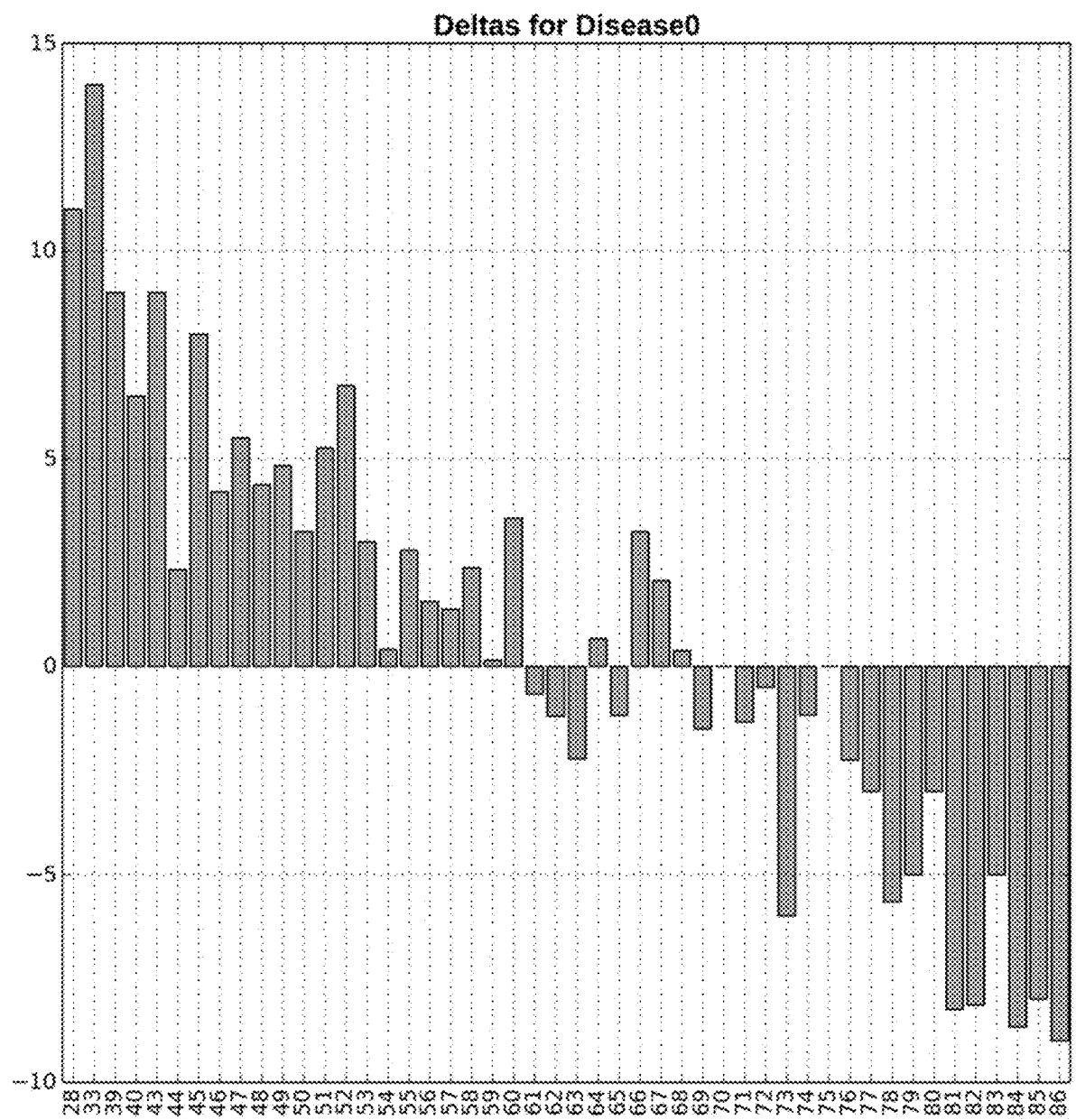
FIG. 8 illustrates the delta (difference between assigned (predicted) biological age and actual chronological age) bar plots grouped by age ranges for healthy people based on an exemplary validation set as described.

FIG. 8 illustrates the delta (difference between assigned (predicted) biological age and actual chronological age) bar plots grouped by age ranges for healthy people based on an exemplary validation set as described. The delta here is defined as the difference between assigned biological age and real age. Thus, for example, a positive value means that a particular organism or person has been assigned a higher age than actual chronological age.

Figure 9:
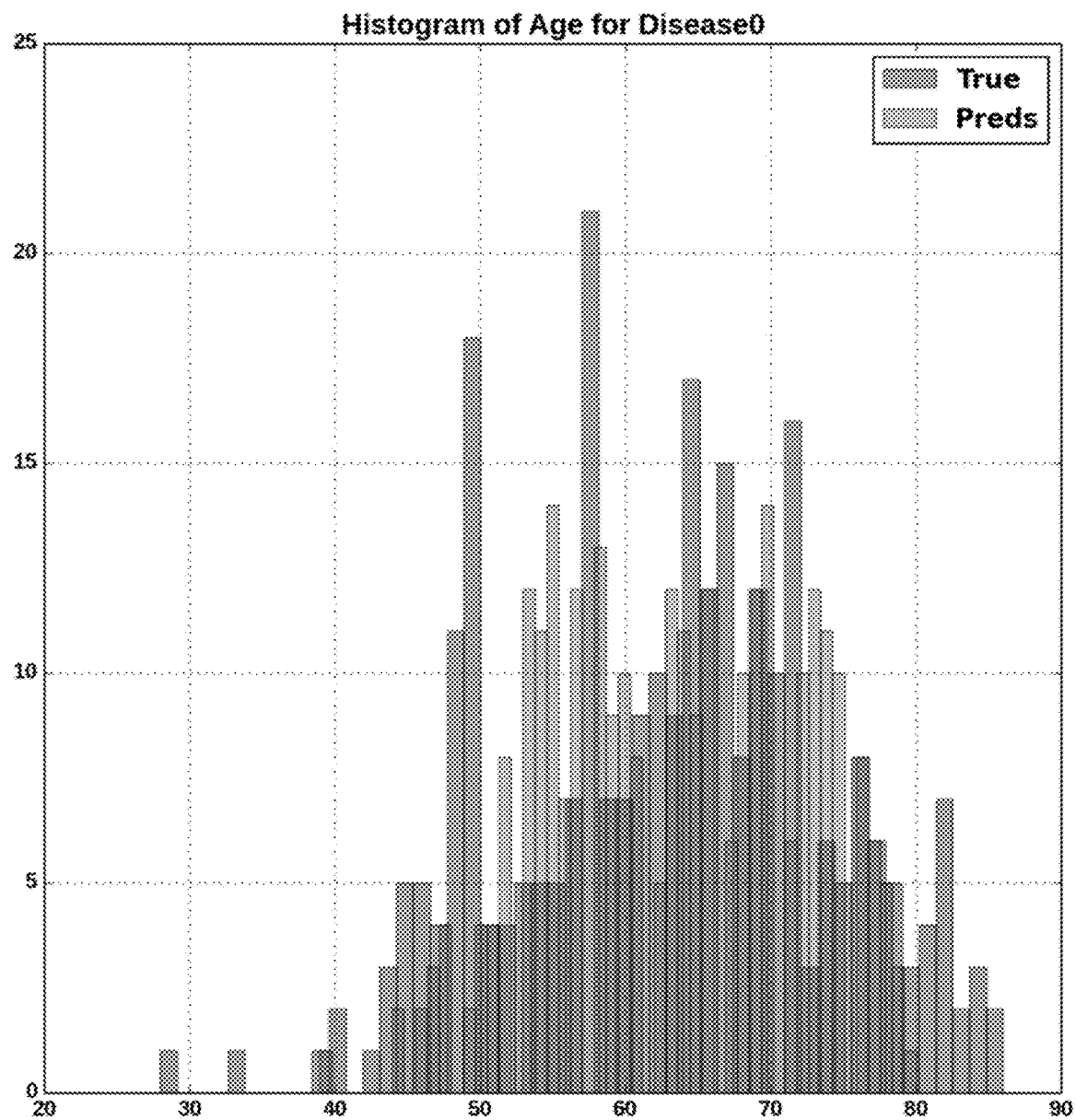
FIG. 9 illustrates distribution on number of samples by age for healthy individuals in the validation set.

FIG. 9 illustrates distribution on number of samples by age for healthy individuals in the validation set. Blue (darker) and green (lighter) values are actual chronological age and assigned biological ages, respectively. For relatively healthy people, not surprisingly, assigned biological is close to chronological age. During the training of the GA for the selection of the most important age-related genes, different derivative-based methods were applied for the initialization of the GA.

Figure 10:
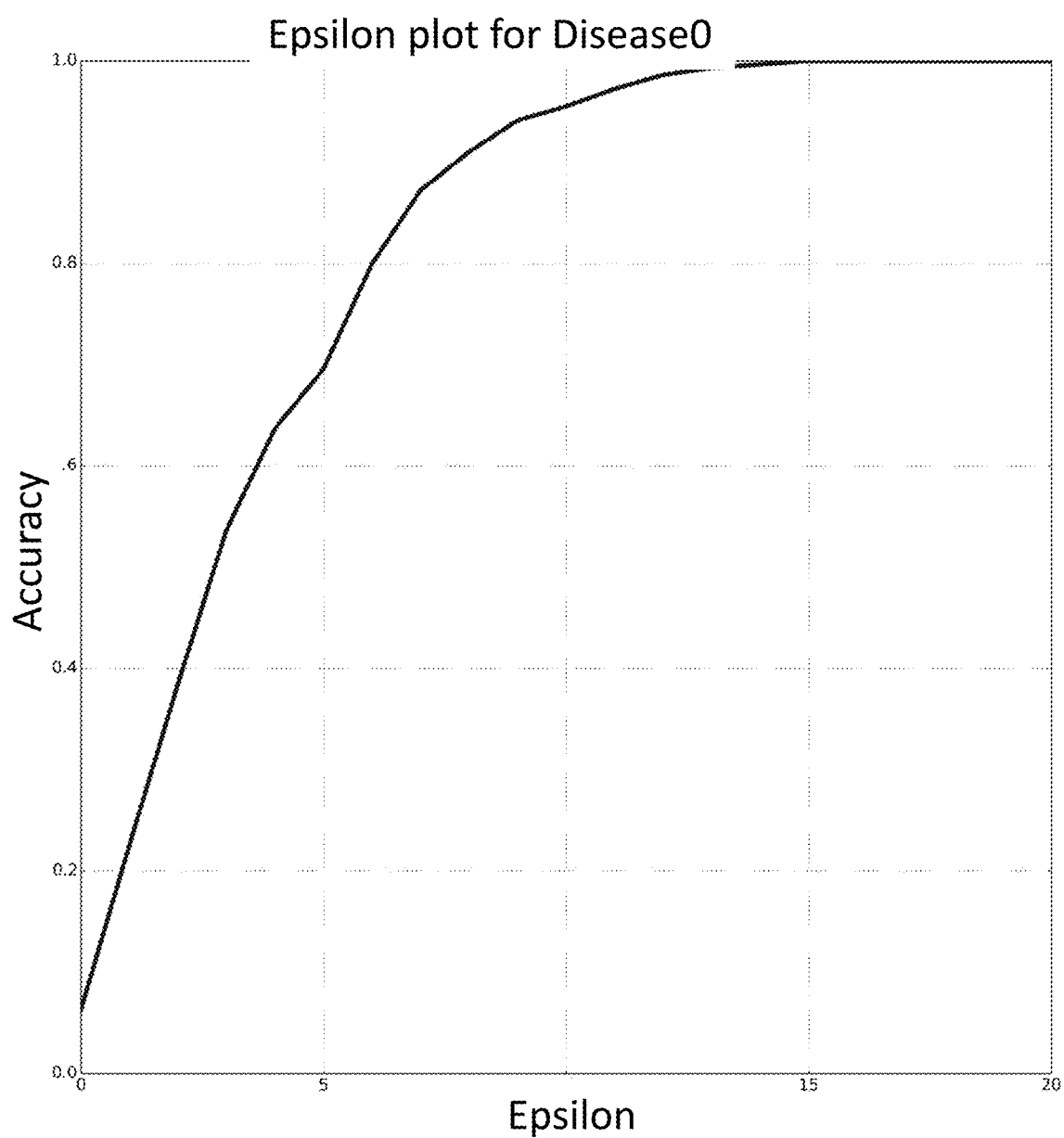
FIG. 10 illustrates an example epsilon-prediction accuracy for healthy individuals.

FIG. 10 illustrates an example epsilon-prediction accuracy for healthy individuals. The accuracy in function of the Epsilon is shown on the FIG. 10. The epsilon-prediction accuracy is defined as follows:

$$\varepsilon - \text{prediction} = \frac{\sum_{i=1}^{N} 1_A(f_i)}{N}$$

Where $f_i$ is the predicted value, $1_A$ is an indicator function with $A \in [y_i-\varepsilon; y_i+\varepsilon]$ For example, if epsilon=0 and yi=45, the DNN correctly recognizes this sample if the prediction of the sample belongs to the interval.

Figure 11:
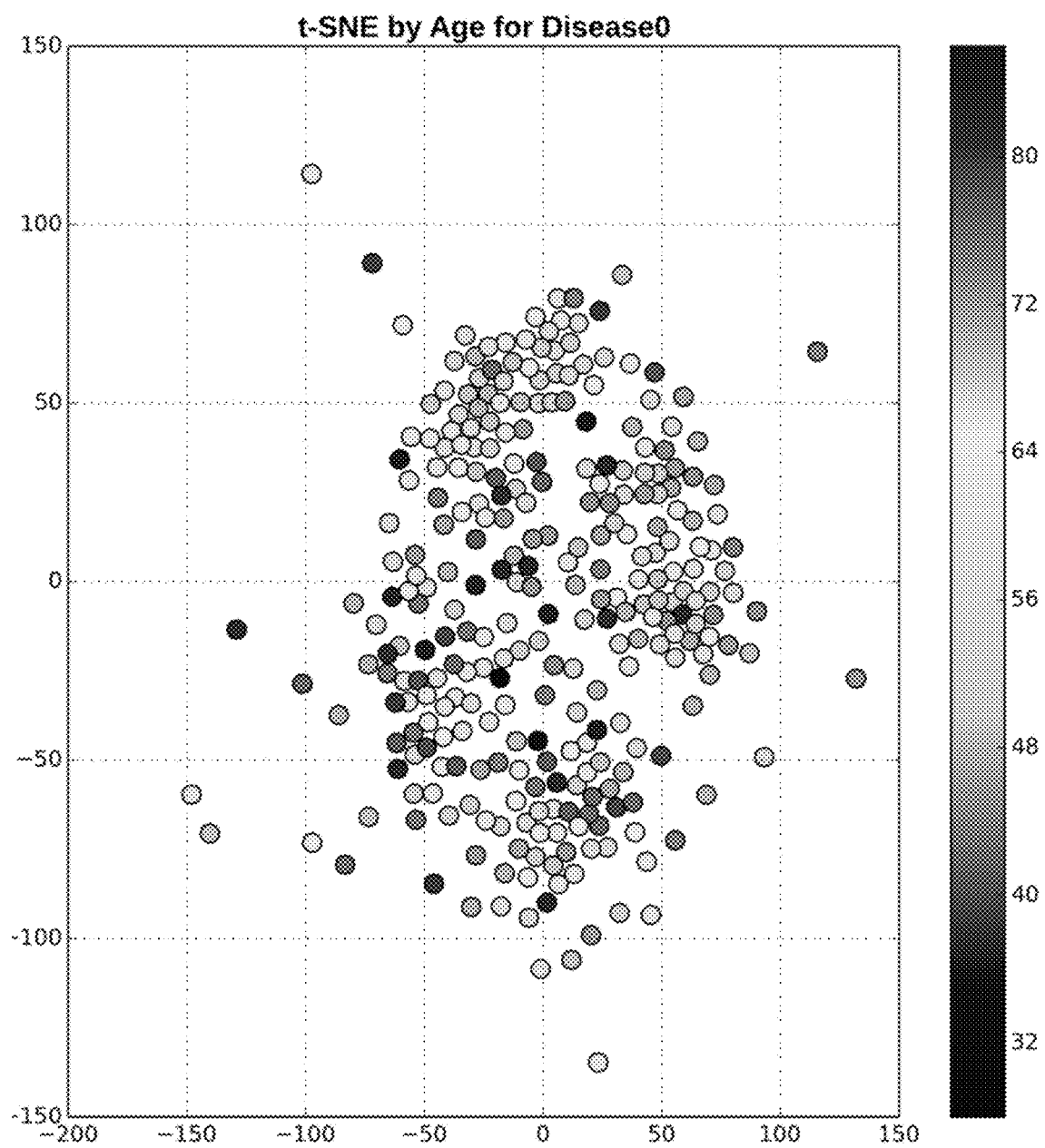
FIG. 11 is a histogram illustrates clustering using t-SNE clustering algorithm by age for healthy individuals.

FIG. 11 is a histogram illustrates clustering using t-SNE clustering algorithm by age for healthy individuals. Color bar indicates the age of the sample. For this particular example, there are no clearly defined clusters of healthy individuals by age.

Table A provides 49 genes that are determined to be significantly important, in a preferred embodiment, for age prediction grouped by disease and molecular function category.

TABLE A

| Category | List of genes in each category |
|---|---|
| Metabolism and energy homeostasis | ACACB, SCD, ALDOC, SMOX, AMACR, HTRA1, ARG1, HLCS, HSD3B7, PECI |
| Hypertension and hypoxia | PTGDS, HPGD, NT5E, TMSB4Y, ADORA2B, ACTN1, SNTB2. |
| Neuropathy | NETO2, GRM2, CACNA1I, NRCAM, CCT5, BAIAP2, QPRT, TMEM18, PPP1R9B, |
| Genomic stability | TOP1MT, PARP3, NOTCH1, TAF7, TINF2, CHTOP, CTBP1, CBX7, RRP1, RNF144, PNPT1, C16orf42 |
| Smooth muscle construction | ADORA2B, SOD1 |
| Age-related macular degeneration | HTRA1 |
| Tumor angiogenesis | CD248, VASH1, SERTAD3, TNFSF8, YWHAE, CRK, CBLL1, CDCA7L, E2F4 |
| Inflammation | AKIRIN2, DEFB123, PLXNC1, PSMD12; RELA |

Table B lists of 100 gene names and abbreviations, all human, used for transcriptome clock analysis in a preferred embodiment.

TABLE B

| Gene Name | Ensembl gene ID | David Gene Name | Species |
|---|---|---|---|
| ACACB | ENSG00000076555 | acetyl-CoA carboxylase beta(ACACB) | *Homo sapiens* |
| ADORA2B | ENSG00000170425 | adenosine A2b receptor(ADORA2B) | *Homo sapiens* |
| AKIRIN2 | ENSG00000135334 | akirin 2(AKIRIN2) | *Homo sapiens* |
| AMACR | ENSG0000242110 | alpha-methyl acyl-CoA racemase(AMACR) | *Homo sapiens* |
| ANKRD54 | ENSG00000100124 | ankyrin repeat domain 54(ANKRD54) | *Homo sapiens* |
| ARFGAP3 | ENSG00000242247 | ADP ribosylation factor GTPase activating protein 3(ARFGAP3) | *Homo sapiens* |
| ARHGAP26 | ENSG00000145819 | Rho GTPase activating protein 26(ARHGAP26) | *Homo sapiens* |
| BAIAP2 | ENSG00000175866 | BAI1 associated protein 2(BAIAP2) | *Homo sapiens* |
| BET1 | ENSG00000105829 | Bet1 golgi vesicular membrane trafficking protein(BET1) | *Homo sapiens* |
| BPNT1 | ENSG00000162813 | 3'(2'), 5'-bisphosphate nucleotidase 1(BPNT1) | *Homo sapiens* |
| C16orf42 | ENSG00000007520 | TSR3, Acp Transferase Ribosome Maturation Factor | *Homo sapiens* |
| C7orf48 | ENSG00000170222 | ADP-Ribose/CDP-Alcohol Diphosphatase, Manganese | *Homo sapiens* |
| C1orf77 | ENSG00000160679 | Chromatin Target Of PRMT1 | *Homo sapiens* |
| C9orf91 | ENSG00000157693 | Transmembrane Protein 268 | *Homo sapiens* |
| CACNA1I | ENSG00000100346 | calcium voltage-gated channel subunit alpha1 I(CACNA1I) | *Homo sapiens* |
| CBLL1 | ENSG00000105879 | Cbl proto-oncogene like 1(CBLL1) | *Homo sapiens* |
| CBX7 | ENSG00000100307 | chromobox 7(CBX7) | *Homo sapiens* |
| CCT5 | ENSG00000150753 | chaperonin containing TCP1 subunit 5(CCT5) | *Homo sapiens* |
| CD248 | ENSG00000174807 | CD248 molecule(CD248) | *Homo sapiens* |
| CDCA7L | ENSG00000164649 | cell division cycle associated 7 like(CDCA7L) | *Homo sapiens* |
| CDK6 | ENSG00000105810 | cyclin dependent kinase 6(CDK6) | *Homo sapiens* |
| CLDN14 | ENSG00000159261 | claudin 14(CLDN14) | *Homo sapiens* |
| CLIC3 | ENSG00000169583 | chloride intracellular channel 3(CLIC3) | *Homo sapiens* |
| COBRA1 | ENSG00000188986 | Negative Elongation Factor Complex Member B | *Homo sapiens* |
| CRK | ENSG00000167193 | CRK proto-oncogene, adaptor protein(CRK) | *Homo sapiens* |
| CTBP1 | ENSG00000159692 | C-terminal binding protein 1(CTBP1) | *Homo sapiens* |
| DAPP1 | ENSG00000070190 | dual adaptor of phosphotyrosine and 3-phosphoinositides 1(DAPP1) | *Homo sapiens* |
| DBNDD2 | ENSG00000244274 | dysbindin domain containing 2(DBNDD2) | *Homo sapiens* |
| DEFB123 | ENSG00000180424 | defensin beta 123(DEFB123) | *Homo sapiens* |
| DERPC | ENSG00000168802 | Chromosome Transmission Fidelity Factor 8 | *Homo sapiens* |
| DHTKD1 | ENSG00000181192 | dehydrogenase E1 and transketolase domain containing 1(DHTKD1) | *Homo sapiens* |
| E2F4 | ENSG00000205250 | E2F transcription factor 4(E2F4) | *Homo sapiens* |
| FANCL | ENSG00000115392 | Fanconi anemia complementation group L(FANCL) | *Homo sapiens* |
| FLJ10374 | ENSG00000105248 | coiled-coil domain containing 94 | *Homo sapiens* |
| FLJ43093 | ENSG00000255587 | RAB44, Member RAS Oncogene Family | *Homo sapiens* |
| FZD1 | ENSG00000157240 | frizzled class receptor 1(FZD1) | *Homo sapiens* |
| GALNS | ENSG00000141012 | galactosamine (N-acetyl)-6-sulfatase(GALNS) | *Homo sapiens* |
| GALNT6 | ENSG00000139629 | polypeptide N-acetylgalactosaminyltransferase 6(GALNT6) | *Homo sapiens* |
| GATAD2A | ENSG00000167491 | GATA zinc finger domain containing 2A(GATAD2A) | *Homo sapiens* |
| GLT1D1 | ENSG00000151948 | glycosyltransferase 1 domain containing 1(GLT1D1) | *Homo sapiens* |
| GPA33 | ENSG00000143167 | glycoprotein A33(GPA33) | *Homo sapiens* |
| GRM2 | ENSG00000164082 | glutamate metabotropic receptor 2(GRM2) | *Homo sapiens* |
| HSD3B7 | ENSG00000099377 | hydroxy-delta-5-steroid dehydrogenase, 3 beta- and steroid delta-isomerase 7(HSD3B7) | *Homo sapiens* |

TABLE B-continued

| Gene Name | Ensembl gene ID | David Gene Name | Species |
|---|---|---|---|
| LDOC1L | ENSG00000188636 | leucine zipper down-regulated in cancer 1 like(LDOC1L) | Homo sapiens |
| LIPN | ENSG00000204020 | lipase family member N(LIPN) | Homo sapiens |
| LMCD1 | ENSG00000071282 | LIM and cysteine rich domains 1(LMCD1) | Homo sapiens |
| LOC100130298 | ENSG00000258130 | hCG1816373-like(LOC100130298) | Homo sapiens |
| LOC285908 | ENSG00000179406 | Long Intergenic Non-Protein Coding RNA 174 | Homo sapiens |
| LOC613038 | ENSG00000258130 | SAGA complex associated factor 29 pseudogene(LOC613038) | Homo sapiens |
| LOC643905 | ENSG00000221961 | Proline Rich 21 | Homo sapiens |
| LOC652784 | NA | NA | Homo sapiens |
| LOC653884 | NA | serine/arginine-rich splicing factor 10-like | Homo sapiens |
| LOC729338 | ENSG00000224786 | Centrin 4, Pseudogene (CETN4P) | Homo sapiens |
| LOC731444 | NA | NA | Homo sapiens |
| LRP3 | ENSG00000130881 | LDL receptor related protein 3(LRP3) | Homo sapiens |
| MFNG | ENSG00000100060 | MFNG O-fucosylpeptide 3-beta-N-acetylglucosaminyltransferase (MFNG) | Homo sapiens |
| NETO2 | ENSG00000171208 | neuropilin and tolloid like 2(NETO2) | Homo sapiens |
| NRCAM | ENSG00000091129 | neuronal cell adhesion molecule(NRCAM) | Homo sapiens |
| NTSR2 | ENSG00000169006 | neurotensin receptor 2(NTSR2) | Homo sapiens |
| NUDT5 | ENSG00000165609 | nudix hydrolase 5(NUDT5) | Homo sapiens |
| PACSIN2 | ENSG00000100266 | protein kinase C and casein kinase substrate in neurons 2(PACSIN2) | Homo sapiens |
| PARP3 | ENSG00000041880 | poly(ADP-ribose) polymerase family member 3(PARP3) | Homo sapiens |
| PARP8 | ENSG00000151883 | poly(ADP-ribose) polymerase family member 8(PARP8) | Homo sapiens |
| PECI | ENSG00000198721 | Enoyl-CoA Delta Isomerase 2 | Homo sapiens |
| PLXNC1 | ENSG00000136040 | plexin C1(PLXNC1) | Homo sapiens |
| PNPT1 | ENSG00000138035 | polyribonucleotide nucleotidyltransferase 1(PNPT1) | Homo sapiens |
| PPP1R9B | ENSG00000108819 | protein phosphatase 1 regulatory subunit 9B(PPP1R9B) | Homo sapiens |
| PSMD12 | ENSG00000197170 | proteasome 26S subunit, non-ATPase 12(PSMD12) | Homo sapiens |
| QPRT | ENSG00000103485 | quinolinate phosphoribosyltransferase(QPRT) | Homo sapiens |
| RAB3D | ENSG00000105514 | RAB3D, member RAS oncogene family(RAB3D) | Homo sapiens |
| RELA | ENSG00000173039 | RELA proto-oncogene, NF-kB subunit(RELA) | Homo sapiens |
| RGMB | ENSG00000174136 | repulsive guidance molecule family member b(RGMB) | Homo sapiens |
| RNASET2 | ENSG00000026297 | ribonuclease T2(RNASET2) | Homo sapiens |
| RNF144 | ENSG00000151692 | Ring Finger Protein 144A | Homo sapiens |
| RRP1 | ENSG00000160214 | ribosomal RNA processing 1(RRP1) | Homo sapiens |
| S100A9 | ENSG00000163220 | S100 calcium binding protein A9(S100A9) | Homo sapiens |
| SERTAD3 | ENSG00000167565 | SERTA domain containing 3(SERTAD3) | Homo sapiens |
| SGPL1 | ENSG00000166224 | sphingosine-1-phosphate lyase 1(SGPL1) | Homo sapiens |
| SIGLEC7 | ENSG00000168995 | sialic acid binding Ig like lectin 7(SIGLEC7) | Homo sapiens |
| SLC25A19 | ENSG00000125454 | solute carrier family 25 member 19(SLC25A19) | Homo sapiens |
| SLC38A10 | ENSG00000157637 | solute carrier family 38 member 10(SLC38A10) | Homo sapiens |
| SOD1 | ENSG00000142168 | superoxide dismutase 1, soluble(SOD1) | Homo sapiens |
| SRPRB | ENSG00000144867 | SRP receptor beta subunit(SRPRB) | Homo sapiens |
| TAF7 | ENSG00000178913 | TATA-box binding protein associated factor 7(TAF7) | Homo sapiens |
| TCTN3 | ENSG00000119977 | tectonic family member 3(TCTN3) | Homo sapiens |
| TIGD7 | ENSG00000140993 | tigger transposable element derived 7(TIGD7) | Homo sapiens |
| TINF2 | ENSG00000092330 | TERF1 interacting nuclear factor 2(TINF2) | Homo sapiens |
| TMEM18 | ENSG00000151353 | transmembrane protein 18(TMEM18) | Homo sapiens |
| TMSB4Y | ENSG00000154620 | thymosin beta 4, Y-linked(TMSB4Y) | Homo sapiens |
| TNFSF8 | ENSG00000106952 | tumor necrosis factor superfamily member 8(TNFSF8) | Homo sapiens |
| TRIM7 | ENSG00000146054 | tripartite motif containing 7(TRIM7) | Homo sapiens |
| TSPAN10 | ENSG00000182612 | tetraspanin 10(TSPAN10) | Homo sapiens |
| VKORC1L1 | ENSG00000196715 | vitamin K epoxide reductase complex subunit 1 like 1(VKORC1L1) | Homo sapiens |
| VTI1B | ENSG00000100568 | vesicle transport through interaction with t-SNAREs 1B(VTI1B) | Homo sapiens |
| YWHAE | ENSG00000108953 | tyrosine 3-monooxygenase/tryptophan 5-monooxygenase activation protein epsilon(YWHAE) | Homo sapiens |
| ZNF259 | ENSG00000109917 | ZPR1 Zinc Finger | Homo sapiens |
| ZNF544 | ENSG00000198131 | zinc finger protein 544(ZNF544) | Homo sapiens |
| ZNF583 | ENSG00000198440 | zinc finger protein 583(ZNF583) | Homo sapiens |

TABLE B-continued

| Gene Name | Ensembl gene ID | David Gene Name | Species |
|---|---|---|---|
| ZNF697 | ENSG00000143067 | zinc finger protein 697(ZNF697) | Homo sapiens |
| ZNF763 | ENSG00000197054 | zinc finger protein 763(ZNF763) | Homo sapiens |

Under the pressure of environmental factors and hereditary characteristics, the rate of aging naturally varies between individuals. As a result, biological age as defined by biomarkers often differs between individuals of the same chronological age. Biomarkers of biological aging again are the objective physiological indicators of tissues and organ conditions that are used to assess personal aging rates. Aging is of course associated with health risks, inability to maintain homeostasis and eventual death prognosis of age-related diseases.

The biomarkers of biological aging as described herein can evaluate the effectiveness of anti-aging remedies. This is of importance as populations in developed nations throughout the world are rapidly aging, and the search and identification of efficient anti-aging interventions, has never been more essential.

Because aging is a complex multifactorial process with no single cause or treatment (Zhavoronkov 2011; Trindade, 2013) that affects most if not all tissues and organs of the body, the currently available biomarkers in the art do not accurately represent the health state of the entire organism or individual systems, and do not provide accurate and useful measures of biological age. Furthermore, several of them are not easily measured. Thus biomarkers based on not only quantifiable but also easily measurable characteristics are still required.

Usually, identifying and developing biomarkers is a multi-steps process that includes proof of concept, experimental validation and analytical performance validation. Nevertheless, alternative approaches based on in silico methods can also be used in order to improve and speed up the development and validation process of these biomarkers. The use of more effective computational approaches for the development of biomarker is favored by two technological trends. First of all, the accumulation of high-throughput data generated from different research areas such as proteomics, genomics, chemoproteomics and phenomics. The second technological trend is the progress made in computational sciences that, combined with increasingly powerful computational resources, allows the development of repurposing algorithms but also of software's for retrospective analysis as well as the maintenance of web-based databases which are required for the gathering and classification of the experimental data (Lavecchia, 2016). Using these computational resources, various techniques such as Machine Learning (ML) are routinely used in biomarker development.

Although Deep Learning (DL) methods were initially developed for dealing with task such as pattern, voice and image recognition (Oquab 2014), they can also be used to improve the efficiency of in silico techniques applied for biomarkers identification. DL-based methods are indeed able to overcome many current limitation of more traditional in silico techniques. For instance, for integrating biomedical data which are complex. The modern DL techniques include powerful approaches with deep architecture, called Deep Neural Networks (DNNs). Neural Networks are collections of neurons (also called units) connected in an acyclic graph. Neural Network models are often organized into distinct layers of neurons.

For most neural networks, the most common layer type is the fully-connected layer in which neurons between two adjacent layers are fully pairwise connected, but neurons within a single layer share no connections. One of the main features of DNN is that neurons are controlled by non-linear activation functions. This non-linearity combined with the deep architecture make possible more complex combinations of the input features leading ultimately to a wider understanding of the relationships between them and as a result to a more reliable final output. DNNs have already been applied for many types of data ranging from structural data to chemical descriptors or transcriptomics data (Mayr 2016, Wang 2014, Ma 2015). Because of this flexibility and adaptability of DNN for learning from large range of data, DNNs are now considered as an interesting computational approach for tackling many current biomedical related issues (Mamoshina 2016, Xu 2015, Hughes 2015).

Recently, Putin et al. (Putin, 2016) have published promising results demonstrating the capacity of DNN-based methods to accurately predict biological age and identify a set of the most relevant biomarkers for tracking physiological processes related to aging. In their study, the features, a set of 41 biomarkers for each sample, used as inputs for the DNN were extracted from tens of thousands of blood biochemistry samples from patients undergoing routine physical examinations. Although being highly variable in nature, blood biochemistry test is in practice very simple to perform and it is approved for clinical use and as a consequence, commonly used by Physicians. An effective DNN structure was obtained using 56177 samples for the training phase (fitting of hyperparameters) with the remaining 6242 samples used for validation. The interesting results obtained for predicting biological age show that DNN-based approach outperform many traditional machine learning methods including GBM (Gradient Boosting Machine), RF (Random Forests), DT (Decision Trees), LR (Linear Regression), kNN (k-Nearest Neighbors), ElasticNet, SVM (Support Vector Machines).

Furthermore, PFI (Permutation Features Importance) method was used to compute the relative importance of each biomarker used to estimate biological age. This information can be used in two ways. Firstly, as each biomarker aims at measuring a specific biological mechanism, this ranking can be exploited to optimize anti-aging strategies by targeting the most critical biological processes identified as playing a key role in the onset and propagation of aging. Secondly, this list can be used to reduce the number of initial inputs required to generate accurate prediction of biological age. Regarding this second point, the results presented in the study show that although each sample initially contains up to 46 biomarkers, the performance of DNNs remained remarkably stable with an input comprising only the 10 first markers with the highest PFI score. Thus, PFI provide a ranked list of biomarkers that can be used to select the most robust and reliable features for predicting age.

The growing body of evidence on experimental data on life extension of model organisms suggests the feasibility of finding interventions promoting human longevity (Moskalev A 2017). However, the restricted experimental possibilities of studying human aging and overall low translation rate from model organisms to the human clinic in other therapeutic areas (Mak, Evaniew, and Ghert 2014) complicates the search of desirable anti-aging therapies and only a few geroprotectors, anti-aging molecules, shown potential efficacy in humans (A. Aliper et al. 2016; I. Thomas and Gregg 2017; A. M. Aliper et al. 2015).

For the past several decades, research in understanding the molecular basis of human aging has progressed significantly. Changes in gene expression are associated with numerous biological processes, cellular responses and disease states most likely play the crucial role in aging process. (de Magalhães, Curado, and Church 2009).

Because biological aging is not a single signature, but highly specific in terms or organs, tissues, systems, and other granular aspects of the organism (including humans), an effective and useful biological clock must utilize many biomarkers from many tissues and organs. The following are some preferred examples.

Energy Metabolism:

Glycolysis, glucose oxidation, fatty acids oxidation are main sources of ATP generation, which is crucial for the viability of tissue with high-energy demand, such as muscle tissue, and especially cardiomyocytes. Aging process triggers abnormalities in metabolism and energy homeostasis (Ma and Li 2015), and aging biomarkers specific to energy metabolism are a subject of the present invention.

Hypertension and Hypoxia:

Prostaglandins are critical to regulate vasodilation and vasoconstriction and to maintain vascular homeostasis. Balance of vasodilating and vasoconstricting agents is important to maintain normal vascular function. Aging process shift the balance toward a pro-constrictive agents and hypertension, which is the common vascular complication in elderly (Pinto 2007).

No matter the particular biomarkers being assessed by a biological aging assessment compatible with the current invention, a preferred embodiment of the deep learning computational approach for both the current invention and biological aging assessment is as follows. Firstly, a specific type of DNN called Deep Feature Selection (DFS) is trained on blood gene expression samples using standard back-propagation algorithm. Secondly, the DFS model is applied to select a set of age-related genes using different DNN-based feature selection methods combined into one ensemble model via genetic algorithm.

During the first step, DFS model is trained, for example, on 4000 healthy human blood gene expression samples extracted from GEO (GSE33828). DFS (Li et al.) is type of neural network with several specific characteristics. Firstly, DFS adds a particularly hidden layer, called a weighted layer, which bridges one to one input features with neurons in the weighted layer. After that the neurons in the weighted layer are connected one to many with neurons in first normal hidden layer of deep feed forward multilayer neural network. Secondly, DFS introduces several regularization terms in the neural network loss function. An exemplary final loss function expression is as follows:

$$\min_\theta f(\theta) = l(\theta) + \lambda_1 \left( \frac{1-\lambda_2}{2} \|w\|_2^2 + \lambda_2 \|w\|_1 \right) + \alpha_1 \left( \frac{1-\alpha_2}{2} \sum_{k=1}^{K+1} \|W^{(k)}\|_F^2 + \alpha_2 \sum_{k=1}^{K+1} \|W^{(k)}\|_1 \right),$$

where $l(\theta)$ is the log-likelihood of data, $\lambda 1$, $\lambda 2$, $a1$ and $a2$ are regularization terms. K is the number of hidden layers. $\|w\|_2^2$ and $\|w\|_1$ stand for the l2 and l1 norm for weight in weighted layer, respectively. $\|*\|_F$ stands for the Frobenius norm and $\|*\|_1$ for the matrix norm. The last two terms are the ElasticNet-based terms that control smoothness/sparsity for weights of weighted layer. They reduce the model complexity and speed up the training. After DFS model was trained the absolute values of the weights in the weighted layer could be used as ranking list for the input features (genes).

During the second step, DNN-based feature selection methods are used to select age-related genes. Each method produces a ranked list of relative importance for each gene. In addition to the ranking of input features available with the DFS model itself, other methods have been applied. This includes the permutation feature importance (PFI) method as previously described in [Putin et al.], the heuristic variable selection (HVS) (Yacoub et al.) and methods based on output derivatives. The notable characteristic of these methods is that they can be applied to already trained DNNs. It is not necessary to iteratively retrain DNNs as required by the forward or backward feature selection methods.

Heuristic Variable Selection (Yacoub et al.) is a zero first order method designed for measuring the relative importance of input features of neural network. The method requires that the set of weight values and information related to the DNN structure as inputs. In a preferred embodiment, the relative importance of each given input feature is computed as follows:

$$S_i = \sum_{j \in H} \left( \frac{|w_{ji}|}{\sum_{i' \in I} |w_{ji'}|} \sum_{k \in O} \frac{|w_{kj}|}{\sum_{j' \in H} |w_{kj'}|} \right)$$

where I, H, O are the number of input, hidden and output layers, respectively. Note wji denotes the weight between neurons j and i. After the training of the DNN and the computation of S for each input feature i, the set of S values can be assembled as a ranked list.

There are various of first order methods to measure the relative importance of an input feature. These methods used either the derivative of the error or the output of the neural network with respect to this input feature to establish the ranked list. An interesting property of the derivative-based methods is that they can be applied to any type of differentiable h are specific to each derivative-based method. The procedure to compute the average relevance of the input feature and how the derivative term is included. Here we consider the long-studied derivative-based methods described in details in (Dorizzi et al.), (Ruck et al.), (Refenes et al.), (Czernichow et al.). In the following formulas, $$\frac{df\ j(x^l)}{dx_i}$$

means an output derivative of unit j of the network with respect to xi in xl point, Fj(xl) in is an output of the network with ul as input, N is the number of samples. If specified, M is a number of outputs of the network, var stands for the variance, $q_{95}$ or 95% percentile. In the table below the relative importance Si of an input feature i is presented by methods.

The biological aging assessment uses, as an example:

1) The model developed by Ruck et al., which is the following:

$$S_i = \sum_{l=1}^{N} \sum_{j=1}^{g} \left| \frac{\partial f_j}{\partial x_i}(x^l) \right|$$

(2) Refenes et al., have developed three different models:

$$S_i = \frac{1}{N} \frac{\text{var}(x_i)}{\text{var}(f(x)-y)} \sum_l \left( \frac{\partial f}{\partial x_i}(x^l) \right)^2$$

$$S_i = \frac{1}{N^{1/2}} \frac{\left( \sum_l \left( \frac{\partial f}{\partial x_i}(x^l) - \sum_j \frac{\partial f}{\partial x_i}(x^j) \right)^2 \right)^{1/2}}{\sum_l \frac{\partial f}{\partial x_i}(x^j)}$$

$$S_i = \frac{1}{N} \sum_l \left| \frac{\partial f}{\partial x_i}(x^l) \cdot \frac{x_i}{f(x^l)} \right|$$

3) The model of Dorizzi et al. takes the following form:

$$S_i = q_{95}\left( \left| \frac{\partial f}{\partial x_i}(x) \right| \right)$$

4) The model of Czernichow et al. is as follows:

$$S_i = \frac{\sum_{i=1}^{N'} \left( \frac{\partial f}{\partial x_i}(x^l) \right)^2}{\max_j \left( \sum_{i=1}^{N'} \left( \frac{\partial f}{\partial xj}(x^l) \right)^2 \right)}$$

The final list of ranked genes is obtained by combining the different lists described above using simple genetic algorithm (GA). In a preferred embodiment, the GA proceeds according to the following.

The initial population of genes is initialized by all feature ranking lists obtained by applying the aforementioned feature selection algorithms on both DNN and DFS models. On each iteration the GA performed 35 crossover operations between its populations and 15 mutation operations, during which random genes were injected in the training of GA. Thus at each iteration, 50 DNNs were trained. Convergence of the GA was reached after 50 epochs and final gene ranking list was obtained. The best DNN model in the GA got 0.79 of coefficient of determination and 4.2 mean absolute error on validation dataset. On FIG. 7, one can see the performance of the DNN for predicting the age of healthy individuals (#=0.79).

Cellular Life Span, Aging, Tissue-Specific Age Prediction, thus, biological aging assessment compatible with the current invention.

As discussed above, different cell and tissues exhibit different expression patterns, different aging patterns, and different life-spans. This substantial variation means that it is useful to have aging clocks that are specific to different cells, tissues, and organs (Seim, Ma, and Gladyshev 2016). In a preferred embodiment we utilize DNN-based predictors of age trained on 12 tissues and 4 tissue-specific DNN-based predictors of age trained on gene expression profiles of a mononuclear whole blood fraction.

Despite the fact that universal 12-tissues based predictor is trained at the data set with a larger sample size compared to 4 tissues specific deep aging clocks, its prediction performance is significantly worse (11.2 years for best network compared to 6.4, 8.2, 7.8 and 8.3 years for Blood, Brain, Liver and M. Blood-based predictors respectively).

In a preferred embodiment we utilize a DFS algorithm for feature ranking to identify the most important genes in age prediction on the universal 12-tissues based predictor of age as well the 4 tissues specific predictors of age.

In an implementation of the method a universal 12-tissues based predictor is trained on a data set with a larger sample size compared to 4 tissues specific deep aging clocks, its prediction performance is significantly worse (11.2 years for best network compared to 6.4, 8.2, 7.8 and 8.3 years for Blood, Brain, Liver and M. Blood based predictors, respectively).

Data from up to 51,139 samples profiled on a GLP570 microarray platform was used to train and test our DNNs. The GLP570 GEO accession numbers refers to data generated using the common Affymetrix Human Genome U133 Plus 2.0 Array, which covers approximately 47,000 transcripts, although only 12,328 or 12,428 transcripts were used in the study. Data was split into training and test sets with a 90:10 ratio with exact values shown in each results section.

Following on from the successful and highly accurate usage of our DNN to classify sex we then attempted to predict classify based on age of samples. As discussed previously we approached age prediction as a regression-based problem. In a preferred embodiment, 12,328 genes over a total of 20,766 samples were used, 18,261 samples were used to train and 2,505 samples used to test. Our DNN-based age predictor delivered a MAE of 11.46 years, a significant improvement over standard machine learning models, with k-NN coming closest to matching the DNN with a MAE of 14.973 years. A very small increase (0.085) in MAE was observed following DFS for the 1,000 most relevant genes suggesting that there was little extra training capacity in the DNN using selected gene expression dataset.

Since we saw a clear ability to distinguish tissues by our DNN we investigated if the MAE of the age predictor, would change when investigating tissue specific aging. In a preferred embodiment, 12, 428 genes were analyzed from 1,853 samples from whole blood (1,733 train, 120 test), 372 from brain (278 train, 49 test), 287 from liver (228 train, 47 test) and 267 mononuclear blood fractions (170 train, 97 test); again using a regression based model. Remarkably, in all cases a significant improvement over the MAE of our general DNN-based age predictor was observed, with whole blood performing especially well generating a MAE of 6.696. Further improvements were seen following DFS, with a particularly large decrease in MAE observed in brain samples (10.788 vs 8.209). In all instances the various DNN outperformed RF, k-NN and LR models often producing an MAE more than 50% smaller. In total, these observations suggest that the transcriptomic aging-clock is regulated in a tissue specific manner.

Multilayer (with 3 or 4 hidden layers) feed-forward neural networks with a standard backpropagation algorithm were used in a preferred embodiment. A Python implementation of the Keras library with Theano backend was used to build and train neural networks and Scikit-learn library to build and train random forest (RF), K-nearest neighbor (k-NN) and linear regression (LR) models. Grid search algorithm was used for hyperparameter optimization in order to achieve the greatest predictive accuracy.

After rounds of optimization, Adam optimizer with Nesterov momentum and learning rate of 0.01 was selected for all models. Rectified linear unit (ReLU) either exponential linear unit (ELU) were selected as activation functions. Mean absolute error (MAE) loss function was used in a regression task of age prediction. For regularization purposes models were trained with a dropout with 20-50% probability after each layer. Performance of the best DNNs were compared to best (with optimized hyperparameters) RF and k-NN algorithms where appropriate. For the purposes of this study we treated the prediction of human age as a regression based problem as previously discussed (Putin E 2017) therefore age related experiments are also compared against a LR model. All experiments were conducted with 5-fold cross validation by drugs on NVIDIA GTC Titan Pascal with 128 Gb of RAM.

Example 3

The first step of 5R strategy is rescuing pre-senescent cells in a particular tissue (including skin, liver and lungs). Pre-senescent phenotype is considered potentially reversible. Senoremediators are the compounds which can reverse the pre-senescent state in the tissue/organ.

Evidence indicates that BRAF (V600E) oncogene-induced senescence (OIS) can be reversed by activation of phosphatidylinositol 3-kinase (PI3K) or inhibition of PDH (Kaplon et al. 2013; Vredeveld et al. 2012).

Combined inhibition of both mTORC1 and mTORC2 also may provide a promising strategy to reverse the development of senescence-associated features in near-senescent cells (Walters, Deneka-Hannemann, and Cox 2016).

In order to rescue the cells demonstrating pre-senescent phenotype the specific set of possible interventions shall be applied. These interventions include the treatment with the one senoremediator compound or a combination of the senoremediator compounds from the list below.

Activators of PI3K: Insulin receptor substrate (Tyr608) peptide, the sequence is established and known in the art, is from insulin receptor substrate-1 (IRS-1) inclusive of Tyr608 (mouse)-Tyr612 (human). It contains the insulin receptor tyrosine kinase substrate motif YMXM (Tyr-Met-X-Met). This peptide has been used as a substrate for purified insulin receptor (Km=90 µM) and other tyrosine kinases in phosphocellulose binding assays. The tyrosine phosphorylated version of this peptide binds to phosphatidylinositol 3-kinase (PI 3-kinase) SH2 domain and activates the enzyme.

740 Y-P: cell-permeable phosphopeptide activator of PI3K. The PDGFR 740Y-P peptide stimulates a mitogenic response in muscle cells. The ability of the 740Y-P peptide to stimulate mitogenesis is highly specific and not a general feature of a cell permeable SH2 domain binding peptides. See ncbi.nlm.nih dot gov/pubmed/9790922.

mTORC1, mTORC2 inhibitors: sapanisertib (Wise-Draper et al. 2017; Moore et al. 2018), dactolisib (Wise-Draper et al. 2017).

Inhibitors of PDH: GSK2334470 (GlaxoSmithKline), MP7 (Merck). (Emmanouilidi and Falasca 2017).

Compounds found based on transcriptional signature analysis according to the procedure described in example 1: Withaferin A, Lavendustin A, Sulforaphane.

Senoremediator compounds can be administered orally, by injection, sublingually, buccally, rectally, vaginally, cutaneously, transdermally, ocularly, oticly or nasally or other method.

Example 4

This step is performed to eliminate the cells that, already entered the irreversible senescent state. Senescent cells lose their function and possess a constant danger to the surrounding cells as described above. Elimination of such cells may prevent surrounding cells to enter the senescent phenotype by positive loop and restore the normal tissue functioning. In order to eliminate the cells demonstrating senescent phenotype the specific set of possible interventions shall be applied. These interventions include the treatment with the one senolytic compound or a combination of the senolytic compounds from the list below.

Combination of dasatinib plus quercetin. As it was shown in (Xu et al. 2018) combination of dasatinib plus quercetin of intermittent oral administration to both senescent cell—transplanted young mice and naturally aged mice alleviated physical dysfunction and increased post-treatment survival by 36% while reducing mortality hazard to 65%.

The following compounds have been found based on transcriptional signature analysis according to the procedure described in Example 1.

Flavopiridol, a flavonoid derived from an indigenous plant from India, demonstrated potent and specific in vitro inhibition of all cdks tested (cdks 1, 2, 4 and 7) with clear block in cell cycle progression at the G1/S and G2/M boundaries. Preclinical studies demonstrated the capacity of flavopiridol to induce programmed cell death, promote differentiation, inhibit angiogenic processes and modulate transcriptional events (Senderowicz 1999).

Linifanib, an orally bioavailable, small-molecule receptor tyrosine kinase (RTK) inhibitor with potential antineoplastic activity. Linifanib inhibits members of the vascular endothelial growth factor (VEGF) and platelet-derived growth factor (PDGF) receptor families; it exhibits much less activity against unrelated RTKs, soluble tyrosine kinases, or serine/threonine kinases. This agent does not have a general antiproliferative effect due to its high dose requirement. However, linifanib may exhibit potent antiproliferative and apoptotic effects on tumor cells whose proliferation is dependent on mutant kinases, such as fms-related tyrosine kinase receptor-3 (FLT3) ("NCI Drug Dictionary" n.d.).

Argatroban, is an anticoagulant that is a small molecule direct thrombin inhibitor. ("Argatroban" n.d.).

Withaferin A, which is widely researched for its anti-inflammatory, cardioactive and central nervous system effects. (Mohan et al. 2004)

Senolytic compounds can be administered orally, by injection, sublingually (e.g., argatroban), buccally, rectally, vaginally, cutaneously, transdermally, ocularly, oticly or nasally or other method.

Example 5

The replenishment step leads to the general rejuvenation of the cells in the population, but on the other hand, to the reduction in the total cell count. This necessitate the further replenish step needed for repopulation of the tissue with functional cells. Therefore the pool of the cells in a particular tissue should be activated in order to replenish the tissue. The possible interventions needed to achieve that goal include the treatment with the one specific compound or a combination of the compounds from the list below.

It has been shown that senescent cells have been successfully dedifferentiated into pluripotent stem cells (Lapasset et al. 2011).

Transcription factors to turn cells into pluripotent: OSKM gene set (oct4, sox2, klf-4, myc), NANOG, Lin28 can be used in vitro to make patient-specific pluripotent stem cells/different progenitors.

Importantly the compounds should stimulate the proliferation of the stem cells, but on the other hand prevent the unwanted effects related to the possible uncontrolled proliferation and subsequent malignant transformation. The compounds should be administered orally, by injection, sublingually, buccally, rectally, vaginally, cutaneously, transdermally, ocularly, oticly or nasally or other method.

Example 6

The reinforcement step is required to prevent the further potential degradation of the tissue (or organ). It may include the treatment with the one specific compound or a combination of the compounds from the list below. These compounds should demonstrate one of the following activities: immunomodulation in order to prevent possible malignant transformation and the accumulation of the senescent cells, cytoprotection in order to retain the functional state of the tissue, stimulation of the macrophages in order to achieve the specific state of senophagy (ability to specifically engulf and digest senescent cells).

Sorafenib inhibits tumor-cell proliferation and angiogenesis by blocking both the intracellular Raf kinase pathway and extracellular VEGFRs and PDGFR-β associated kinases. (Abou-Alfa et al. 2017). Sorafenib has also been reported to have immunomodulatory effects in addition to enhancing the tyrosine kinase inhibition of cancer proliferation and angiogenesis. (Houben et al. 2009).

Tucaresol, an orally bioavailable immunopotentiatory drug, has been shown to enhance T-helper-cell activity, with the induction of increased IL-2 and IFN-γ levels in mice and humans (Rhodes et al. 1995).

Naturally occurring flavonoids discussed in the present article have optimal immunomodulation to prevent immune-mediated disorders through management of Th1/Th2 cytokine balance. (Gandhi et al. 2018).

Prevention of bleomycin-induced pulmonary fibrosis by IVIG (intravenous immunoglobulin has been demonstrated by reduced expression of collagen-I protein in the affected lungs. (Molina et al. 2006).

Cell therapy with adipose tissue-derived stem cells (ASCs). The immunomodulatory and therapeutic effects of ASCs were confirmed in the mouse model both in vitro and in vivo. (Yoshizumi et al. 2017).

Antigen independent immunomodulatory agents (like methotrexate, tacrolimus, and curcumin) delivered via transdermal route for immunomodulation.

The compounds should be administered orally, by injection, sublingually, buccally, rectally, vaginally, cutaneously, transdermally, ocularly, oticly or nasally or other method.

The steps may be carried out in any order or repeated. A database which contains the full list is in (Aliper, Belikov, et al. 2016). This data can be stored on a memory device in a computing system of the invention.

The stem cells may be mesenchymal, epithelial stem cells, induced-pluripotent stem cells or a combination. The method may further include applying a reinforcement drug treatment protocol to the patient, using, immunomodulation, cytoprotection, or stimulation of macrophages.

TABLE C

Example list of small molecule molecules and short peptides for the reinforcement step.

| Name | Formula |
|---|---|
| Insulin receptor substrate (Tyr608) peptide | enzolifesciences.com/bml-p320/irs-l-tyr608-peptide/ |
| 740 Y-P | rndsystems.com/products/740-y-p_1983 |
| Sapanisertib | 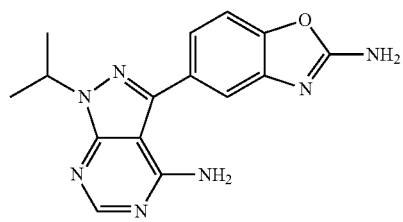 [SMILES: CC(C)n1nc(-c2ccc3oc(N)nc3c2)c2c(N)ncnc21] |

TABLE C-continued
Example list of small molecule molecules and short peptides for the reinforcement step.
| Name | Formula |
|---|---|
| Dactolisib | 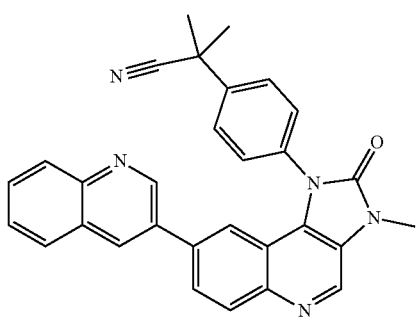 [SMILES: Cn1c(=O)n(-c2ccc(C(C)(C)C#N)cc2)c2c3cc(-c4cnc5ccccc5c4)ccc3ncc21] |
| GSK2334470 | 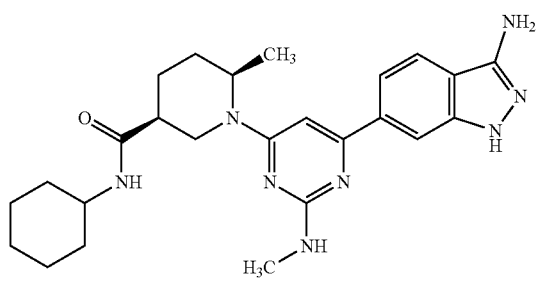 [SMILES: CNc1nc(-c2ccc3c(N)n[nH]c3c2)cc(N2C[C@@H](C(=O)NC3CCCCC3)CC[C@H]2C)n1] |
| MP7 | 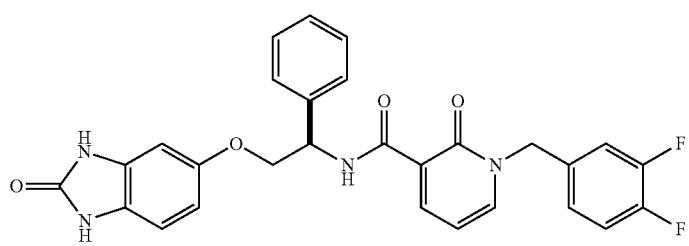 [SMILES: O=C(N[C@@H](COc1ccc2[nH]c(=O)[nH]c2c1)c1ccccc1)c1cccn(Cc2ccc(F)c(F)c2)c1=O] |
| Dasantinib | 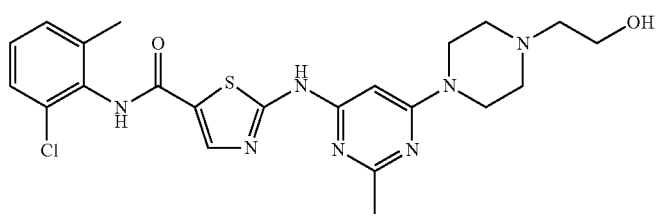 [SMILES: Cc1nc(Nc2ncc(C(=O)Nc3c(C)cccc3Cl)s2)cc(N2CCN(CCO)CC2)n1] |
| Quercetin | 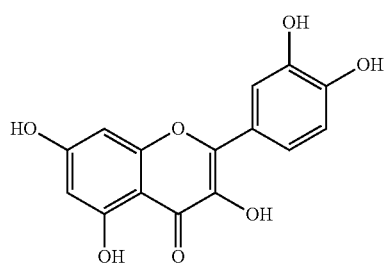 [SMILES: O=c1c(O)c(-c2ccc(O)c(O)c2)oc2cc(O)cc(O)c12] |

TABLE C-continued
Example list of small molecule molecules and short peptides for the reinforcement step.
| Name | Formula |
|---|---|
| Flavopiridol | 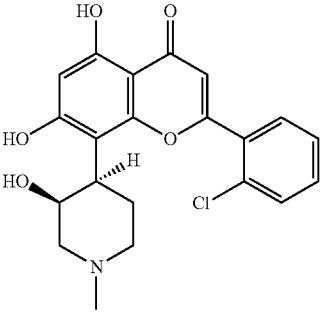 [SMILES: CN1CC[C@H](c2c(O)cc(O)c3c(=O)cc(-c4ccccc4Cl)oc23)[C@H](O)C1] |
| Linifanib | 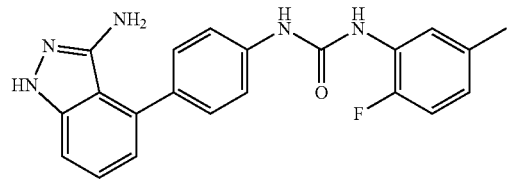 [SMILES: Cc1ccc(F)c(NC(=O)Nc2ccc(-c3cccc4[nH]nc(N)c34)cc2)c1] |
| Argatroban | 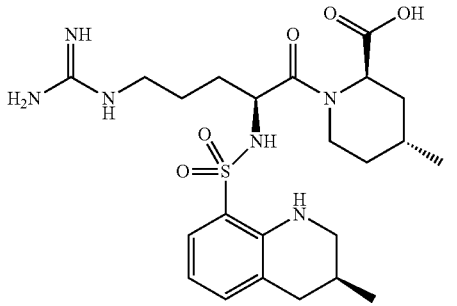 [SMILES: C[C@@H]1CNc2c(cccc2S(=O)(=O)N[C@@H](CCCNC(=N)N)C(=O)N2CC[C@@H](C)C[C@@H]2C(=O)O)C1] |
| Sorafenib | 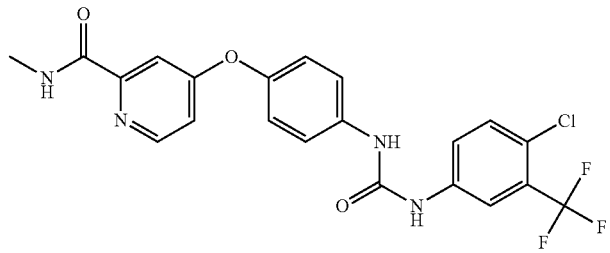 [SMILES: CNC(=O)c1cc(Oc2ccc(NC(=O)Nc3ccc(Cl)c(C(F)(F)F)c3)cc2)ccn1] |
| Tucaresol | 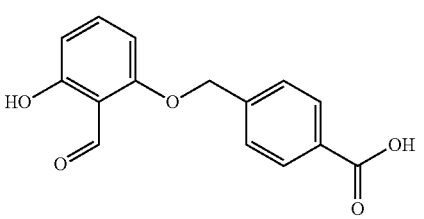 [SMILES: O=Cc1c(O)cccc1OCc1ccc(C(=O)O)cc1] |
| Methotrexate | 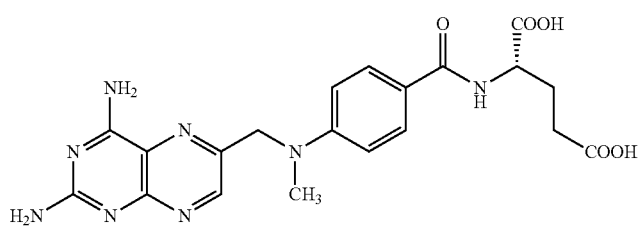 [SMILES: CN(Cc1cnc2nc(N)nc(N)c2n1)c1ccc(C(=O)N[C@@H](CCC(=O)O)C(=O)O)cc1] |

TABLE C-continued

Example list of small molecule molecules and short peptides for the reinforcement step.

| Name | Formula |
|---|---|
| Tacrolimus | 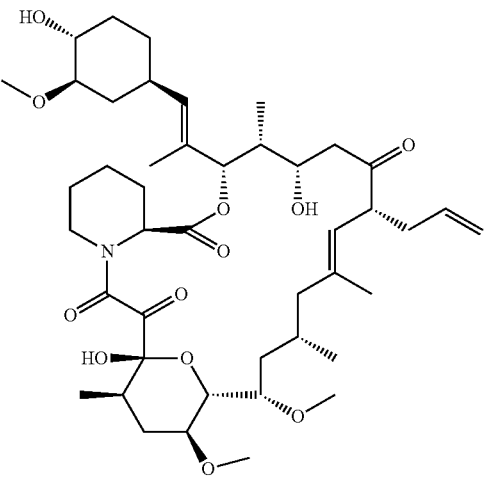 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC] |
| Curcumin | 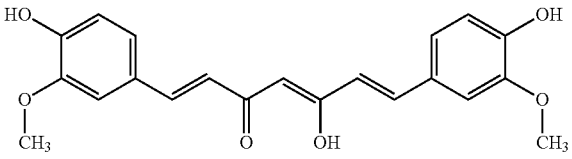 [SMILES: COc1cc(/C=C/C(=O)/C=C(O)/C=C/c2ccc(O)c(OC)c2)ccc1O] |
| Sulforaphane | 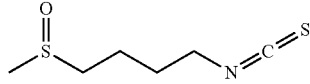 |
| Withaferin A | 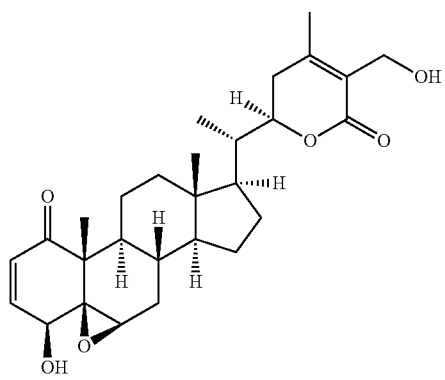 |
| Lavendustin A | 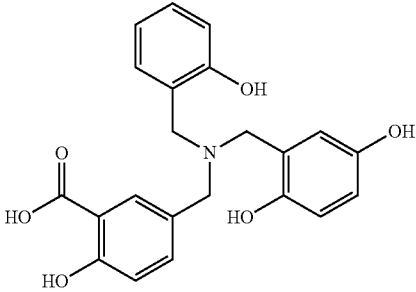 [SMILES: O=C(O)c1cc(CN(Cc2ccccc2O)Cc2cc(O)ccc2O)ccc1O] |

For these and other processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Unless specifically stated otherwise, as apparent from the following discussions, it is appreciated that throughout the specification discussions utilizing terms such as "processing", "computing", "calculating", "determining", "deriving", "generating" or the like, refer to the action and/or processes of a computer or computing system, or processor or similar electronic computing device, that manipulate and/or transform data represented as physical, such as electronic, quantities within the computing system's registers and/or memories into other data, similarly represented as physical quantities within the computing system's memories, registers or other such information storage, transmission or display devices.

It is noteworthy that any hardware platform suitable for performing the processing described herein is suitable for use with the systems and methods provided herein. Computer-readable storage media refer to any medium or media that participate in providing instructions to a central processing unit (CPU), a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD-ROM disk, digital video disk (DVD), any other optical storage medium, RAM, PROM, EPROM, a FLASHEPROM, any other memory chip or cartridge.

Computer program code for carrying out operations for aspects of the present technology may be written in any combination of one or more programming languages, including an object oriented programming language such as Python, Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be coupled with the user's computer through any type of network, including a local area network (LAN) or a wide area network (WAN), or the connection may be made to an external computer (for example, through the Internet using an Internet Service Provider).

Figure 12:
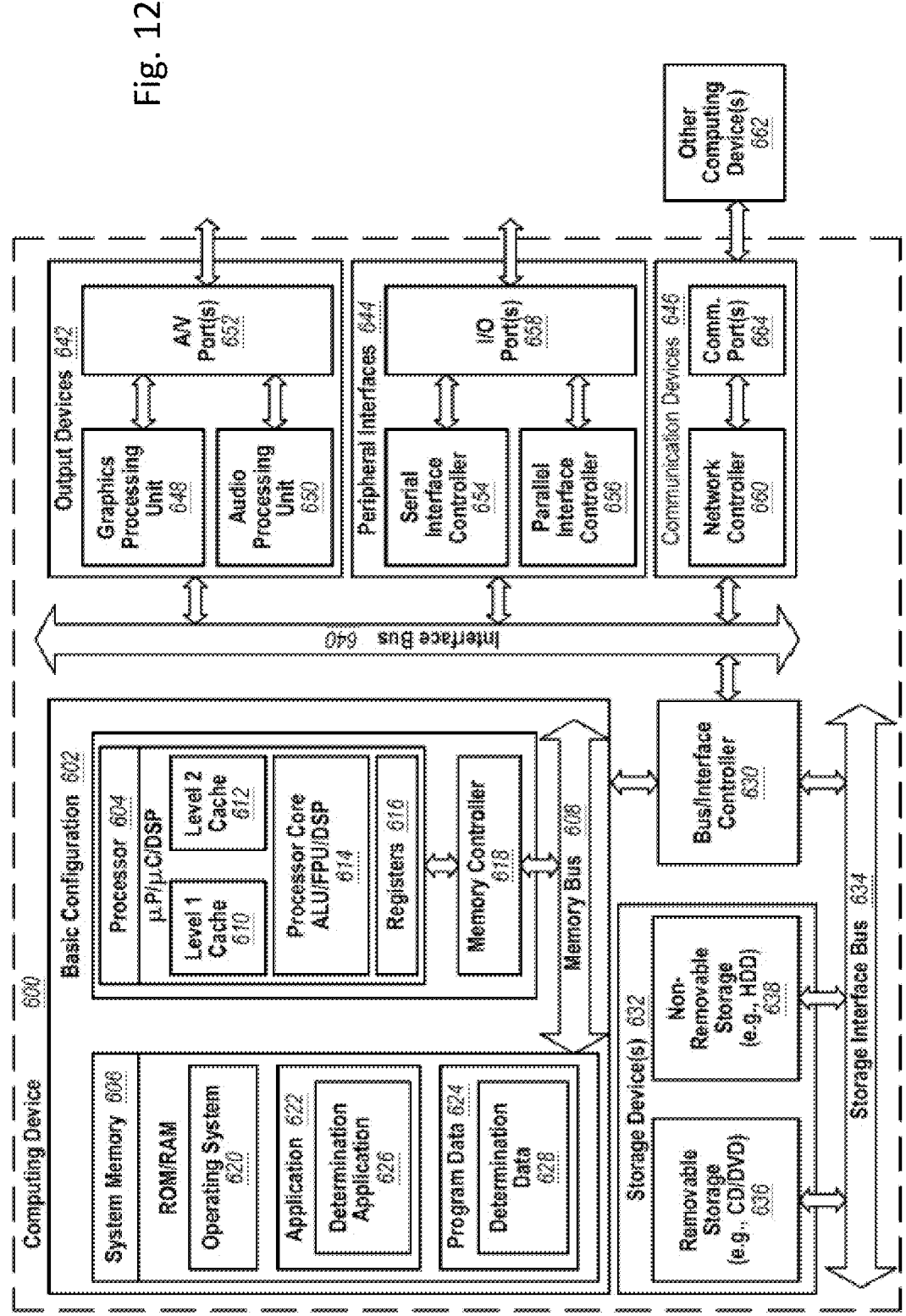
FIG. 12 shows an example computing device 600 (e.g., a computer) that may be arranged in some embodiments to perform the methods (or portions thereof) described herein.

FIG. 12 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (μP), a microcontroller (μC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

Definitions

A "biopsy" is a medical test involving extraction of sample cells or tissues for examination, and can be analyzed chemically. When only a sample of tissue is removed with preservation of the histological architecture of the tissue's cells, the procedure is called an incisional biopsy or core biopsy. When a sample of tissue or fluid is removed with a needle in such a way that cells are removed without preserving the histological architecture of the tissue cells, the procedure is called a needle aspiration biopsy.

"Senescence" is biological aging, that is, the gradual deterioration of function and ability in almost all life forms, mostly after maturation and in particular multi-cellular life. Senescence increases mortality. Senescence refer to cellular senescence, tissue senescence, organ senescence, and senescence of the whole organism. Cellular senescence largely underlies organismal senescence. The boundary between disease and senescence as organisms, tissues, and cells, may have characteristics of both, as disease and senescence are often associated with each other.

"Cellular senescence" is not the aging of an individual cell, but instead, the state (gene expression) of a cell with respect to the senescence of its tissue or organism, in comparison to a less senescent tissue or organism. Cell senescence may partly be the result of telomere shortening cells, which may trigger a DNA damage response. Cells can also be induced to senesce via DNA damage in response to elevated reactive oxygen species, activation of oncogenes, cell-to-cell fusion, and other causes. As such, cellular senescence represents a change in "cell state" rather than a cell becoming "aged" The number of senescent cells in tissues rises substantially during normal aging. Cells may also experience "replicative senescence", in which they can no longer divide. There is a "senescence associated secretory phenotype" (SASP) associated with senescent cells, which is associated with, for example, an increase in inflammatory cytokines, growth factors, and proteases. Cellular senescence contributes to age-related diseases, such as atherosclerosis.

"Fibrosis" is the accumulation of excess fibrous connective cells or other similarly stiff, structural cells, called "fibrotic cells" in an organ or tissue. Such fibrosis can be a normal, functional part of the reparative process (such as scarring) but can also be pathological. Excess and unnecessary fibrosis is associated with senescence, typically decrease flexibility and other function of a tissue or organ. Fibrotic cells generally have an excess of extracellular matrix proteins which contribute to their stiffness.

A "senolytic" is a drug of other treatment that can selectively induce death of senescent cells.

A "senoremediator" is a drug of other treatment that can restore or increase the number of presenescent or nonsenescent cells.

"Machine learning" (ML) is a subfield of computer science that gives computers the ability to learn without being explicitly programmed. Machine learning platforms include, but are not limited to naïve bayes classifiers, support vector machines, decision trees, and neural networks.

"Artificial neural networks", also called "ANNs" or just "neural networks", are based on a large collection of connected simple units called artificial neurons loosely analogous to axons in a biological brain. If the combined incoming signals are strong enough, the neuron becomes activated and the signal travels to other neurons connected to it. The activation function of such neurons is often, though not always, represented as a sigmoid function.

"Deep learning" (DL) (also known as deep structured learning, hierarchical learning or deep machine learning) is the study of artificial neural networks that contain more than one hidden layer of neurons. Such a neural network is called a "deep neural network". A "convolutional neural network" is a type of neural network in which the connectivity pattern is inspired by the organization of the animal visual cortex.

"Principal component analysis" (PCA) is a statistical procedure that uses an orthogonal transformation to convert a set of observations of variables into a set of values of linearly uncorrelated variables called principal components. The transformation is defined in such a way that the first principal component has the largest possible variance and each succeeding component in turn has the highest variance possible under the constraint that it is orthogonal to the preceding components.

"Generative adversarial networks" (GANs) are neural networks that are trained in an adversarial manner to generate data mimicking some distribution. A discriminative model is a model that discriminates between two (or more) different classes of data, for example a convolutional neural network that is trained to output 1 given an image of a human face and 0 otherwise. A generative model by contrast generates new data which fits the distribution of the training data. GANs are well known in the art, as described, for example, in (2) Goodfellow et. al., "Generative Adversarial Networks", arXiv:1406.2661v1, 2014.

An "autoencoder" is a neural network architecture generally used for unsupervised learning of efficient coding. An autoencoder learn representations (encodings) for a set of data, often for the purpose of dimensionality reduction. An "adversarial autoencoder" (AAE), is an autoencoder that uses generative adversarial networks (GAN) to perform variational inference by matching the aggregated posterior of the hidden code vector of the autoencoder with an arbitrary prior distribution. AAEs are well known in the art, as described, for example, in (3) Makhzani et. al., "Adversarial Autoencoders", arXiv:1511.05644v2, 2015. Application of AAEs to new molecule development such as drugs is also well-known in the art, as described, for example, in (4) Kadurin, et. al., "The cornucopia of meaningful leads: Applying deep adversarial autoencoders for new molecule development in oncology", Oncotarget, 2017, Vol. 8, (No. 7), pp: 10883-10890.

All references recited herein and/or recited in the provisional application 62/536,658 filed Jul. 25, 2017 and/or 62/547,061 filed Aug. 17 2017 are incorporated herein by specific reference in their entirety.

The following References are background literature for operation of the technology described herein, and are incorporated herein by specific reference.

Abou-Alfa, Ghassan K., Jean-Frederic Blanc, Steven Miles, Tom Ganten, Jorg Trojan, Jonathan Cebon, Andre K. Liem, et al. 2017. "Phase II Study of First-Line Trebananib Plus Sorafenib in Patients with Advanced Hepatocellular Carcinoma." The Oncologist 22 (7): 780-e65.

Acosta, Juan Carlos, Ana Banito, Torsten Wuestefeld, Athena Georgilis, Peggy Janich, Jennifer P. Morton, Dimitris Athineos, et al. 2013. "A Complex Secretory Program Orchestrated by the Inflammasome Controls Paracrine Senescence." Nature Cell Biology 15 (8): 978-90.

Aliper, Alexander, Aleksey V. Belikov, Andrew Garazha, Leslie Jellen, Artem Artemov, Maria Suntsova, Alena Ivanova, et al. 2016. "In Search for Geroprotectors: In Silico Screening and in Vitro Validation of Signalome-Level Mimetics of Young Healthy State." Aging 8 (9): 2127-52.

Aliper, Alexander, Sergey Plis, Artem Artemov, Alvaro Ulloa, Polina Mamoshina, and Alex Zhavoronkov. 2016. "Deep Learning Applications for Predicting Pharmacological Properties of Drugs and Drug Repurposing Using Transcriptomic Data." Molecular Pharmaceutics 13 (7): 2524-30.

"Argatroban." n.d. Accessed Jul. 18, 2018. drugbank dot ca/drugs/DB00278.

Arnold, John, and Joanne Silvester. 2005. Work Psychology: Understanding Human Behaviour in the Workplace. Pearson Education.

Baar, Marjolein P., Renata M. C. Brandt, Diana A. Putavet, Julian D. D. Klein, Kasper W. J. Derks, Benjamin R. M. Bourgeois, Sarah Stryeck, et al. 2017. "Targeted Apoptosis of Senescent Cells Restores Tissue Homeostasis in Response to Chemotoxicity and Aging." Cell 169 (1): 132-47.e16.

Baker, Darren J., Robbyn L. Weaver, and Jan M. van Deursen. 2013. "p21 Both Attenuates and Drives Senescence and Aging in BubR1 Progeroid Mice." Cell Reports 3 (4): 1164-74.

Campisi, Judith. 2005. "Senescent Cells, Tumor Suppression, and Organismal Aging: Good Citizens, Bad Neighbors." Cell 120 (4): 513-22.2011.

"Cellular Senescence: Putting the Paradoxes in Perspective." Current Opinion in Genetics & Development 21 (1): 107-12. 2013.

"Aging, Cellular Senescence, and Cancer." Annual Review of Physiology 75: 685-705. Campisi, Judith, and Fabrizio d'Adda di Fagagna. 2007.

"Cellular Senescence: When Bad Things Happen to Good Cells." Nature Reviews. Molecular Cell Biology 8 (9): 729-40.

Chilosi, Marco, Angelo Carloni, Andrea Rossi, and Venerino Poletti. 2013. "Premature Lung Aging and Cellular Senescence in the Pathogenesis of Idiopathic Pulmonary Fibrosis and COPD/emphysema." Translational Research: The Journal of Laboratory and Clinical Medicine 162 (3): 156-73.

Chilosi, Marco, Alberto Zamò, Claudio Doglioni, Daniela Reghellin, Maurizio Lestani, Licia Montagna, Serena Pedron, et al. 2006. "Migratory Marker Expression in Fibroblast Foci of Idiopathic Pulmonary Fibrosis." Respiratory Research 7 (1). doi dot org/10.1186/1465-9921-7-95.

Cohen-Naftaly, Michal, and Scott L. Friedman. 2011. "Current Status of Novel Antifibrotic Therapies in Patients with Chronic Liver Disease." Therapeutic Advances in Gastroenterology 4 (6): 391-417.

Coppé, Jean-Philippe, Christopher K. Patil, Francis Rodier, Yu Sun, Denise P. Munoz, Joshua Goldstein, Peter S. Nelson, Pierre-Yves Desprez, and Judith Campisi. 2008. "Senescence-Associated Secretory Phenotypes Reveal Cell-Nonautonomous Functions of Oncogenic RAS and the p53 Tumor Suppressor." PLoS Biology 6 (12): 2853-68.

De Cecco, Marco, Steven W. Criscione, Edward J. Peckham, Sara Hillenmeyer, Eliza A. Hamm, Jayameenakshi Manivannan, Abigail L. Peterson, Jill A. Kreiling, Nicola Neretti, and John M. Sedivy. 2013. "Genomes of Replicatively Senescent Cells Undergo Global Epigenetic Changes Leading to Gene Silencing and Activation of Transposable Elements." Aging Cell 12 (2): 247-56.

Demaria, Marco, Naoko Ohtani, Sameh A. Youssef, Francis Rodier, Wendy Toussaint, James R. Mitchell, Remi-Martin Laberge, et al. 2014. "An Essential Role for Senescent Cells in Optimal Wound Healing through Secretion of PDGF-AA." Developmental Cell 31 (6): 722-33.

Deursen, Jan M. van. 2014. "The Role of Senescent Cells in Ageing." Nature 509 (7501): 439-46.

DiLoreto, R., and C. T. Murphy. 2015. "The Cell Biology of Aging." Molecular Biology of the Cell 26 (25): 4524-31.

Emmanouilidi, Aikaterini, and Marco Falasca. 2017. "Targeting PDK1 for Chemosensitization of Cancer Cells." Cancers 9 (10). doi dot org/10.3390/cancers9100140.

Freund, Adam, Arturo V. Orjalo, Pierre-Yves Desprez, and Judith Campisi. 2010. "Inflammatory Networks during Cellular Senescence: Causes and Consequences." Trends in Molecular Medicine 16 (5): 238-46.

Gandhi, Gopalsamy Rajiv, Maria Terezinha Santos, Rajiv Gandhi Sathiyabama, Jullyana de Souza Siqueira Quintans, Ana Mara de Oliveira e Silva, Adriano Antunes de Souza Araújo, Narendra Narain, Lucindo José Quintans Júnior, and Ricardo Queiroz Gurgel. 2018. "Flavonoids as Th1/Th2 Cytokines Immunomodulators: A Systematic Review of Studies on Animal Models." Phytomedicine: International Journal of Phytotherapy and Phytopharmacology 44: 74-84.

"Global Strategy for the Diagnosis, Management, and Prevention of Chronic Obstructive Pulmonary Disease: GOLD Executive Summary Updated 2003." 2004. COPD: Journal of Chronic Obstructive Pulmonary Disease 1 (1): 105-41.

Hernandez-Gea, Virginia, and Scott L. Friedman. 2011. "Pathogenesis of Liver Fibrosis." Annual Review of Pathology: Mechanisms of Disease 6 (1): 425-56.

Houben, Roland, Heike Voigt, Christiane Noelke, Valeska Hofmeister, Juergen C. Becker, and David Schrama. 2009. "MAPK-Independent Impairment of T-Cell Responses by the Multikinase Inhibitor Sorafenib." Molecular Cancer Therapeutics 8 (2): 433-40.

Ivanov, Andre, Jeff Pawlikowski, Indrani Manoharan, John van Tuyn, David M. Nelson, Taranjit Singh Rai, Parisha P. Shah, et al. 2013. "Lysosome-Mediated Processing of Chromatin in Senescence." The Journal of Cell Biology 202 (1): 129-43.

Jun, Joon-Il, and Lester F. Lau. 2010. "The Matricellular Protein CCN1 Induces Fibroblast Senescence and Restricts Fibrosis in Cutaneous Wound Healing." Nature Cell Biology 12 (7): 676-85.

Kadurin, Artur, Alexander Aliper, Andrey Kazennov, Polina Mamoshina, Quentin Vanhaelen, Kuzma Khrabrov, and Alex Zhavoronkov. 2017. "The Cornucopia of Meaningful Leads: Applying Deep Adversarial Autoencoders for New Molecule Development in Oncology." Oncotarget 8 (7): 10883-90.

Kaplon, Joanna, Liang Zheng, Katrin Meissl, Barbara Chaneton, Vitaly A. Selivanov, Gillian Mackay, Sjoerd H. van der Burg, et al. 2013. "A Key Role for Mitochondrial Gatekeeper Pyruvate Dehydrogenase in Oncogene-Induced Senescence." Nature 498 (7452): 109-12.

Kim, William Y., and Norman E. Sharpless. 2006. "The Regulation of INK4/ARF in Cancer and Aging." Cell 127 (2): 265-75.

Krimpenfort, Paul, and Anton Berns. 2017. "Rejuvenation by Therapeutic Elimination of Senescent Cells." Cell 169 (1): 3-5.

Krishnamurthy, Janakiraman, Matthew R. Ramsey, Keith L. Ligon, Chad Torrice, Angela Koh, Susan Bonner-Weir, and Norman E. Sharpless. 2006. "p16INK4a Induces an Age-Dependent Decline in Islet Regenerative Potential." Nature 443 (7110): 453-57.

Krizhanovsky, Valery, Monica Yon, Ross A. Dickins, Stephen Hearn, Janelle Simon, Cornelius Miething, Herman Yee, Lars Zender, and Scott W. Lowe. 2008. "Senescence of Activated Stellate Cells Limits Liver Fibrosis." Cell 134 (4): 657-67.

Kuwano, K., R. Kunitake, M. Kawasaki, Y. Nomoto, N. Hagimoto, Y. Nakanishi, and N. Hara. 1996. "P21Waf1/Cip1/Sdi1 and p53 Expression in Association with DNA Strand Breaks in Idiopathic Pulmonary Fibrosis." American Journal of Respiratory and Critical Care Medicine 154 (2 Pt 1): 477-83.

Laberge, Remi-Martin, Pierre Awad, Judith Campisi, and Pierre-Yves Desprez. 2012. "Epithelial-Mesenchymal Transition Induced by Senescent Fibroblasts." Cancer Microenvironment: Official Journal of the International Cancer Microenvironment Society 5 (1): 39-44.

Lapasset, Laure, Ollivier Milhavet, Alexandre Prieur, Emilie Besnard, Amelie Babled, Nafissa Aït-Hamou, Julia Leschik, et al. 2011. "Rejuvenating Senescent and Centenarian Human Cells by Reprogramming through the Pluripotent State." Genes & Development 25 (21): 2248-53.

Lomas, Nicola J., Keira L. Watts, Khondoker M. Akram, Nicholas R. Forsyth, and Monica A. Spiteri. 2012. "Idiopathic Pulmonary Fibrosis: Immunohistochemical Analysis Provides Fresh Insights into Lung Tissue Remodelling with Implications for Novel Prognostic Markers." International Journal of Clinical and Experimental Pathology 5 (1): 58-71.

Malavolta, Marco, Elisa Pierpaoli, Robertina Giacconi, Laura Costarelli, Francesco Piacenza, Andrea Basso, Maurizio Cardelli, and Mauro Provinciali. 2016. "Pleiotropic Effects of Tocotrienols and Quercetin on Cellular Senescence: Introducing the Perspective of Senolytic Effects of Phytochemicals." Current Drug Targets 17 (4): 447-59. The senolytics include tocotrienols (T3s) and quercetin (QUE).

Mallette, Frédérick A., and Gerardo Ferbeyre. 2007. "The DNA Damage Signaling Pathway Connects Oncogenic Stress to Cellular Senescence." Cell Cycle 6 (15): 1831-36.

Minagawa, S., J. Araya, T. Numata, S. Nojiri, H. Hara, Y. Yumino, M. Kawaishi, et al. 2010. "Accelerated Epithelial Cell Senescence in IPF and the Inhibitory Role of SIRT6 in TGF-Induced Senescence of Human Bronchial Epithelial Cells." AJP: Lung Cellular and Molecular Physiology 300 (3): L391-401.

Miotto, Riccardo, Li Li, Brian A. Kidd, and Joel T. Dudley. 2016. "Deep Patient: An Unsupervised Representation to Predict the Future of Patients from the Electronic Health Records." Scientific Reports 6 (May): 26094.

Molina, Vered, Saleem Haj-Yahia, Inna Solodeev, Yair Levy, Miri Blank, and Yehuda Shoenfeld. 2006. "Immunomodulation of Experimental Pulmonary Fibrosis by Intravenous Immunoglobulin (IVIG)." Autoimmunity 39 (8): 711-17.

Moore, Kathleen N., Todd M. Bauer, Gerald S. Falchook, Swapan Chowdhury, Chirag Patel, Rachel Neuwirth, Aaron Enke, Fabian Zohren, and Manish R. Patel. 2018. "Phase I Study of the Investigational Oral mTORC1/2 Inhibitor Sapanisertib (TAK-228): Tolerability and Food Effects of a Milled Formulation in Patients with Advanced Solid Tumours." ESMO Open 3 (2): e000291.

Muñoz-Espin, Daniel, Marta Cañamero, Antonio Maraver, Gonzalo Gomez-Lopez, Julio Contreras, Silvia Murillo-Cuesta, Alfonso Rodriguez-Baeza, et al. 2013. "Programmed Cell Senescence during Mammalian Embryonic Development." Cell 155 (5): 1104-18.

"NCI Drug Dictionary." n.d. National Cancer Institute. Accessed Jul. 18, 2018. cancer dot gov/publications/dictionaries/cancer-drug.

Nelson, Glyn, James Wordsworth, Chunfang Wang, Diana Jurk, Conor Lawless, Carmen Martin-Ruiz, and Thomas von Zglinicki. 2012. "A Senescent Cell Bystander Effect: Senescence-Induced Senescence." Aging Cell 11 (2): 345-49.

Nikolich-Zugich, Janko. 2008. "Ageing and Life-Long Maintenance of T-Cell Subsets in the Face of Latent Persistent Infections." Nature Reviews. Immunology 8 (7): 512-22.

Noble, Paul W., Carlo Albera, Williamson Z. Bradford, Ulrich Costabel, Marilyn K. Glassberg, David Kardatzke, Talmadge E. King Jr, et al. 2011. "Pirfenidone in Patients with Idiopathic Pulmonary Fibrosis (CAPACITY): Two Randomised Trials." The Lancet 377 (9779): 1760-69.

Ohtani, Naoko, Kimi Yamakoshi, Akiko Takahashi, and Eiji Hara. 2004. "The p16INK4a-RB Pathway: Molecular Link between Cellular Senescence and Tumor Suppression." The Journal of Medical Investigation: JMI 51 (3,4): 146-53.

Ozerov, Ivan V., Ksenia V. Lezhnina, Evgeny Izumchenko, Artem V. Artemov, Sergey Medintsev, Quentin Vanhaelen, Alexander Aliper, et al. 2016. "In Silico Pathway Activation Network Decomposition Analysis (iPANDA) as a Method for Biomarker Development." Nature Communications 7 (November): 13427.

Parrinello, Simona, Jean-Philippe Coppe, Ana Krtolica, and Judith Campisi. 2005. "Stromal-Epithelial Interactions in Aging and Cancer: Senescent Fibroblasts Alter Epithelial Cell Differentiation." Journal of Cell Science 118 (Pt 3): 485-96.

Putin, Evgeny, Polina Mamoshina, Alexander Aliper, Mikhail Korzinkin, Alexey Moskalev, Alexey Kolosov, Alexander Ostrovskiy, Charles Cantor, Jan Vijg, and Alex Zhavoronkov. 2016. "Deep Biomarkers of Human Aging: Application of Deep Neural Networks to Biomarker Development." Aging 8 (5): 1021-33.

Raghu, Ganesh, Bram Rochwerg, Yuan Zhang, Carlos A. Cuello Garcia, Arata Azuma, Juergen Behr, Jan L. Brozek, et al. 2015. "An Official ATS/ERS/JRS/ALAT Clinical Practice Guideline: Treatment of Idiopathic Pulmonary Fibrosis. An Update of the 2011 Clinical Practice Guideline." American Journal of Respiratory and Critical Care Medicine 192 (2): e3-19.

Rhodes, J., H. Chen, S. R. Hall, J. E. Beesley, D. C. Jenkins, P. Collins, and B. Zheng. 1995. "Therapeutic Potentiation of the Immune System by Costimulatory Schiff-Base-Forming Drugs." Nature 377 (6544): 71-75.

Seki, Ekihiro, and Robert F. Schwabe. 2015. "Hepatic Inflammation and Fibrosis: Functional Links and Key Pathways." Hepatology 61 (3): 1066-79.

Senderowicz, A. M. 1999. "Flavopiridol: The First Cyclin-Dependent Kinase Inhibitor in Human Clinical Trials." Investigational New Drugs 17 (3): 313-20.

Storer, Mekayla, Alba Mas, Alexandre Robert-Moreno, Matteo Pecoraro, M. Carmen Ortells, Valeria Di Giacomo, Reut Yosef, et al. 2013. "Senescence Is a Developmental Mechanism That Contributes to Embryonic Growth and Patterning." Cell 155 (5): 1119-30.

Takeuchi, Shinji, Akiko Takahashi, Noriko Motoi, Shin Yoshimoto, Tomoko Tajima, Kimi Yamakoshi, Atsushi Hirao, et al. 2010. "Intrinsic Cooperation between p16INK4a and p21Waf1/Cip1 in the Onset of Cellular Senescence and Tumor Suppression in Vivo." Cancer Research 70 (22): 9381-90.

Vredeveld, Liesbeth C. W., Patricia A. Possik, Marjon A. Smit, Katrin Meissl, Chrysiis Michaloglou, Hugo M. Horlings, Abderrahim Ajouaou, et al. 2012. "Abrogation of BRAFV600E-Induced Senescence by PI3K Pathway Activation Contributes to Melanomagenesis." Genes & Development 26 (10): 1055-69.

Walters, Hannah E., Sylwia Deneka-Hannemann, and Lynne S. Cox. 2016. "Reversal of Phenotypes of Cellular Senescence by Pan-mTOR Inhibition." Aging 8 (2): 231-44.

Wang, Jianrong, Glenn J. Geesman, Sirkka Liisa Hostikka, Michelle Atallah, Benjamin Blackwell, Elbert Lee, Peter J. Cook, et al. 2011. "Inhibition of Activated Pericentromeric SINE/Alu Repeat Transcription in Senescent Human Adult Stem Cells Reinstates Self-Renewal." Cell Cycle 10 (17): 3016-30.

Wise-Draper, Trisha M., Ganesh Moorthy, Mohamad A. Salkeni, Nagla Abdel Karim, Hala Elnakat Thomas, Carol A. Mercer, M. Shalaan Beg, et al. 2017. "A Phase Ib Study of the Dual PI3K/mTOR Inhibitor Dactolisib (BEZ235) Combined with Everolimus in Patients with Advanced Solid Malignancies." Targeted Oncology 12 (3): 323-32.

Xu, Ming, Tamar Pirtskhalava, Joshua N. Farr, Bettina M. Weigand, Allyson K. Palmer, Megan M. Weivoda, Christina L. Inman, et al. 2018. "Senolytics Improve Physical Function and Increase Lifespan in Old Age." Nature Medicine, July. doi dot org/10.1038/s41591-018-0092-9. The senolytics include mix of dasatinib plus quercetin.

Yoshizumi, Yasuma, Hiroshi Yukawa, Ryoji Iwaki, Sanae Fujinaka, Ayano Kanou, Yuki Kanou, Tatsuya Yamada, et al. 2017. "Immunomodulatory Effects of Adipose Tissue-Derived Stem Cells on Concanavalin A-Induced Acute Liver Injury in Mice." Cell Medicine 9 (1-2): 21-33.

The invention claimed is:

1. A method of treating senescence in a subject, the method comprising:
    (a) applying a senoremediation drug treatment protocol to the subject in order to rescue one or more first cells in the subject, wherein the senoremediation drug treatment includes administering to the subject at least one senoremediation drug in an amount sufficient to rescue the one or more first cells in the subject, wherein the senoremediation drug increases an amount of the one or more first cells that are presenescent cells that are healthy;
    (b) applying a senolytic drug treatment protocol to the subject in order to remove one or more second cells in the subject, wherein the senolytic drug treatment includes administering to the subject at least one senolytic drug in an amount sufficient to kill the one or more second cells in the subject, wherein the senolytic drug decreases an amount of the one or more second cells that are senescent cells that are unhealthy;
    (c) introducing stem cells into a tissue and/or organ of the subject in order to rejuvenate one or more tissue cells in the tissue and/or one or more organ cells in the organ; and
    (d) carrying out a reinforcement step that includes one or more actions that inhibit further senescence or degradation of the tissue or organ, wherein the one or more actions include administering to the subject at least one reinforcement drug in an amount sufficient to inhibit senescence or degradation of the tissue or organ, wherein the reinforcement drug is selected from an immunomodulation drug, a cytoprotection drug, or macrophage stimulating drug.

2. The method of claim 1, wherein the first cells that are rescued are characterized as pre-senescent cells.

3. The method of claim 1, wherein the second cells that are removed are characterized as senescent cells.

4. The method of claim 1, further comprising repeating at least one of (a) (b) (c) or (d) at least once.

5. The method of claim 1, wherein the stem cells are mesenchymal or epithelial stem cells or both.

6. The method of claim 1, wherein the reinforcement drug includes at least one of:
    Insulin receptor substrate (Tyr608) peptide; 740 Y-P; Sapanisertib; Dactolisib; GSK2334470; MP7; Dasantinib; Quercitin; Flavopiridol; Linifanib; Argatroban; Sorafenib; Tucaresol; Methotrexate; Tacrolimus; Curcumin; Withaferin A; Sulphoraphane; Lavendustin naturally occurring flavonoids; or intravenous immunoglobulin.

7. The method of claim 1, wherein the senoremediation drug is selected from the group consisting of nicotinamide mononucleotide, Withaferin A, Lavendustin, and Sulforaphane.

8. The method of claim 1, wherein the senolytic drug is selected from the group consisting of navitoclax, tocotrienols, quercetin, Withaferin A, Argatroban, Flavopiridol, Linifanib, dasatinib, and quercetin.

* * * * *